(12) United States Patent
Koganov

(10) Patent No.: US 8,318,220 B2
(45) Date of Patent: Nov. 27, 2012

(54) **BIOACTIVE COMPOSITIONS FROM *THEACEA* PLANTS AND PROCESSES FOR THEIR PRODUCTION AND USE**

(75) Inventor: Michael Koganov, White Plains, NY (US)

(73) Assignee: Akzo Nobel Surface Chemistry LLC, Chicago, IL (US)

( * ) Notice: Subject to any disclaimer, the term of this patent is extended or adjusted under 35 U.S.C. 154(b) by 0 days.

(21) Appl. No.: 13/279,928

(22) Filed: Oct. 24, 2011

(65) Prior Publication Data

US 2012/0041059 A1 Feb. 16, 2012

Related U.S. Application Data

(62) Division of application No. 12/335,534, filed on Dec. 15, 2008, now Pat. No. 8,043,635, which is a division of application No. 11/033,925, filed on Jan. 12, 2005, now Pat. No. 7,473,435.

(60) Provisional application No. 60/535,861, filed on Jan. 12, 2004.

(51) Int. Cl.
*A61K 36/82* (2006.01)

(52) U.S. Cl. ........................................ 424/729

(58) Field of Classification Search .............. None
See application file for complete search history.

(56) References Cited

U.S. PATENT DOCUMENTS

| | | | |
|---|---|---|---|
| 2,559,459 A | 7/1951 | Peebles et al. | |
| 3,684,520 A | 8/1972 | Bickoff et al. | |
| 3,775,133 A | 11/1973 | Batley, Jr. | |
| 3,799,806 A | 3/1974 | Madsen | |
| 3,821,346 A | 6/1974 | Batley, Jr. | |
| 3,823,128 A | 7/1974 | Bickoff et al. | |
| 3,849,391 A | 11/1974 | Egger et al. | |
| 3,959,246 A | 5/1976 | Bickoff et al. | |
| 3,993,794 A | 11/1976 | Bernardin | |
| 4,006,078 A | 2/1977 | Bickoff et al. | |
| 4,066,633 A | 1/1978 | Gastineau et al. | |
| 4,072,666 A | 2/1978 | Horisberger et al. | |
| 4,077,950 A | 3/1978 | White | |
| 4,130,553 A | 12/1978 | Batley, Jr. | |
| 4,208,323 A | 6/1980 | Murray et al. | |
| 4,233,210 A | 11/1980 | Koch | |
| 4,234,620 A | 11/1980 | Howard et al. | |
| 4,250,197 A | 2/1981 | Koch | |
| 4,333,871 A | 6/1982 | DeJong | |
| 4,334,024 A | 6/1982 | Johal | |
| 4,347,324 A | 8/1982 | Wildman et al. | |
| 4,359,530 A | 11/1982 | Brown | |
| 4,421,682 A | 12/1983 | Edwards et al. | |
| 4,551,341 A | 11/1985 | Blanie et al. | |
| 4,559,230 A | 12/1985 | David et al. | |
| 4,588,691 A | 5/1986 | Johal | |
| 4,897,345 A | 1/1990 | Harris et al. | |
| 5,043,427 A | 8/1991 | Leberre et al. | |
| 5,096,719 A | 3/1992 | Gresch | |
| 5,433,968 A | 7/1995 | Zarraga et al. | |
| 5,530,103 A | 6/1996 | Livey et al. | |
| 5,616,357 A | 4/1997 | Hartmann | |
| 5,723,149 A | 3/1998 | Bonte et al. | |
| 5,762,994 A | 6/1998 | Juillerat et al. | |
| 5,777,080 A | 7/1998 | Boatright | |
| 5,798,446 A | 8/1998 | Neumuller | |
| 5,882,664 A | 3/1999 | Soma et al. | |
| 5,989,557 A | 11/1999 | Bombardelli et al. | |
| 5,994,508 A | 11/1999 | Bryan et al. | |
| 6,013,771 A | 1/2000 | Shen et al. | |
| 6,037,456 A | 3/2000 | Garger et al. | |
| 6,060,061 A | 5/2000 | Breton | |
| 6,068,862 A | 5/2000 | Ishihara et al. | |
| 6,107,468 A | 8/2000 | Boatright | |
| 6,139,825 A | 10/2000 | Reinhard et al. | |
| 6,147,054 A | 11/2000 | De Paoli Ambrosi | |
| 6,610,749 B2 | 8/2003 | Liao et al. | |
| 6,616,952 B1 | 9/2003 | Berquist | |
| 2003/0113797 A1 | 6/2003 | Jia et al. | |

FOREIGN PATENT DOCUMENTS

| | | | |
|---|---|---|---|
| CN | 1039525 A | 2/1990 | |
| CN | 1144652 A | 3/1997 | |
| GB | 2 054 343 A | 2/1981 | |
| JP | 57-146715 A | 9/1982 | |
| JP | 05-229921 A | 9/1993 | |
| JP | 09202726 A | 8/1997 | |
| JP | 11-001686 A | 1/1999 | |
| KR | 2001112817 A | 12/2001 | |
| WO | 01/72319 A1 | 10/2001 | |

OTHER PUBLICATIONS

Katiyar et al. Polyphenolic Antioxidant (−) Epigallocatechin-3-Gallate From Green Tea Reduces UVB-V Induced Inflammatory Responses and Infiltration of Leukocytes in Human Skin. Phytochemistry and Photobiology. 1999.69 (2) 148-153.*

Supplementary European Search Report issued in European Patent Application No. 05711431.6 (based on PCT/US2005/001132), dated Jul. 9, 2009.

Okai et al., "Potent Suppressive Activity of Nonpolyphenolic Fraction of Green Tea (*Camellia sinensis*) Against Genotoxin-Induced *umu* C Gene Expression in *Salmonella typhimurium* (TA 1535/pSK 1002), Tumor Promoter-Dependent Ornithine Decarboxylase Induction of BALB/c 3T3 Fibroblast Cells, and Chemically Induced Mouse Skin Tumorigenesis," *Teratogenesis, Carcinogenesis, and Mutagenesis*, 17(6):305-312 (1997).

(Continued)

*Primary Examiner* — Melenie McCormick

(74) *Attorney, Agent, or Firm* — Heslin Rothenberg Farley & Mesiti P.C.; Andrew K. Gonsalves

(57) ABSTRACT

The present invention relates to isolated bioactive compositions containing bioactive fractions derived from Theacea plants. The present invention also relates to bioactive topical formulations containing the bioactive compositions. The present invention further relates to methods of using the bioactive compositions of the present invention, including, for example, methods for inhibiting inflammatory activity in skin tissue of a mammal, for protecting skin tissue of a mammal from ultraviolet light-induced damage, and for normalizing skin disorders in skin tissue of a mammal. The present invention also relates to methods for isolating bioactive fractions derived from cell juice or a cell walls component a Theacea plant.

12 Claims, 40 Drawing Sheets

OTHER PUBLICATIONS

Matsui et al., "Fatty Acid Hydroperoxide Cleaving Enzyme, Hydroperoxide Lyase, From Tea Leaves," *Phytochemistry*, 30(7):2109-2113 (1991).

Gensler et al., "Prevention of Photocarcinogensis by Topical Administration of Pure Epigallocatechin Gallate Isolated From Green Tea," *Nutrition and Cancer*, 26(3):325-335 (1996).

Zhao et al., "Photoprotective Effect of Black Tea Extracts Against UVB-Induced Phototoxicity in Skin," *Photochemistry and Photobiology*, 70(4):637-644 (1999).

Vayalil et al., "Treatment of Green Tea Polyphenols in Hydrophilic Cream Prevents UVB-Induced Oxidation of Lipids and Proteins, Depletion of Antioxidant Enzymes and Phosphorylation of MAPK Proteins in SKH-1 Hairless Mouse Skin," *Carcinogenesis*, 24(5):927-936 (2003).

Huang et al., "Effects of Tea, Decaffeinated Tea, and Caffeine on UVB Light-Induced Complete Carcinogenesis in SKH-1 Mice: Demonstration of Caffeine as a Biologically Important Constituent of Tea," *Cancer Research*, 57(13):2623-2629 (1997).

Bray, "Green Crop Fractionation: Product Improvement by Juice Purification," *Progress in Leaf Protein Research*, 129-142 (1984).

Byers, "Extracted Leaf Proteins: Their Amino Acid Composition and Nutritional Quality," *Leaf Protein Concentrates*, 5:135-175 (Telek and Graham eds. 1983).

Carroad et al., "Optimization of Cell Disruption for Alfalfa Leaf Protein Concentration (Pro-Xan) Production," *Journal of Food Science*, 46:383-386 (1981).

Clifford et al., "Nucleic Acid Content and Nutritional Value of Green and White Leaf Proteins of Alfalfa," *Nutrition Reports International*, 15(5):511-518 (1977).

Hanczakowski et al., "Composition and Nutritive Value of Native and Modified Green Fraction of Leaf Protein Lucerne (*Medicago sativa*)," *Journal of Science Food and Agriculture*, 56(4):495-501 (1991).

He et al., "The Comparison on Extraction Methods of Leaf Protein," *Journal of Plant Resources and Environment*, 8(2):63-64 (1999) (English Abstract).

Hughes et al., "The Subcellular Distribution of Tocopherols in the Green Leaves of *Pisum sativum*," *Biochemical Journal*, 124(2):9P-10P (1971).

Jwanny et al., "Protein Production for Human Use From Sugarbeet: Byproducts," *Bioresource Technology*, 43:67-70 (1993).

Koch, "The Vepex Process," *Leaf Protein Concentrates*, 22:601-632 (Telek and Graham eds. 1983).

Kohler et al., "LPC for Feeds and Foods: the Pro-Xan Process," *Leaf Protein Concentrates*, 18:508-524 (Telek and Graham eds. 1983).

Lundborg, "Fractionation of Leaf Proteins by Differential Centrifugation and Gel Filtration," *Physiol. Plant*, 48(1):175-185 (1980).

Ostrowski-Meissner, "Protein Concentrates from Pasture Herbage and Their Fractionation into Feed- and Food-Grade Products," *Leaf Protein Concentrates*, 15:437-466 (Telek and Graham eds. 1983).

Ostrowski-Meissner, "Protein Extraction from Grasslands," *Leaf Protein Concentrates*, 1:9-51 (Telek and Grahm eds. 1983).

Ostrowski-Meissner, "Quantities and Quality of Protein Extracted from Pasture Herbage Using Heat Precipitation or Ultrafiltration Procedures," *Journal of the Science of Food and Agriculture*, 31:177-187 (1980).

Reddy et al., "Green Crop Fractionation: The Distribution of Crop Nutrients in Fractionation Products," *Acta Botanica Indica* 16(1):51-56 (1988).

Solinski, "The Precipitation of Protein Coagulates from Vegetable Juices," *Pr. Nauk. Akad, Ekon. im. Oskara Langego Wroclawiu*, 199:91-123 (1982) (English Abstract).

Walk et al., "Purification and Characterization of Chloroplast Carbonate Dehydratase from Leaves of *Lactuca sativa*," *Hoppe-Seyler's Z. Physiol. Chem.* 356(11):1733-1741 (1975) (English Abstract).

Woodham, "The Nutritional Evaluation of Leaf Protein Concentrates," *Leaf Protein Concentrates* 14:415-433 (Telek and Graham eds. 1983).

Camellia, retrieved from the internet, http://en.wikipedia.org/wiki/Camellia. Retrieved on Dec. 1, 2010, 1 page.

Sakata et al., "Cyanidin 3-Galactoside, a New Anthocyanin from *Camellia japonica* subsp. *rusticana* (Honda) Kitamura and Its Occurrence in the Garden Forms of *Camellia* of Japanese Origin," *J Japan. Soc. Hort. Sci.*, 55(1):82-88 (1986).

Dvorakova et al., "Pharmacokinetics of the Green Tea Derivative EGCG by the Topical Route of Administration in Mouse and Human Skin," *Cancer Chermother Pharamacol.*, 43:331-335 (1999).

Katiyar et al., "Polyphenolic Antioxidant (−) Epigallocatechin-3-Gallate from Green Tea Reduces UVB-Induced Inflammatory Responses and Infiltration of Leukocytes in Human Skin," *Phytochemistry and Photobiology*, 69(2):148-153 (1999).

Tedeshi et al., "Anti-inflammatory action of EGCG, The Main Component of Green Tea, Through STAT-1 Inhibition," *Ann. N. Y. Acad. Sci.*, 973:435-437 (2002).

Lu et al., Topical Applications of Caffeine or (1)-Epigallocatechin Gallate (EGCG) Inhibit Carcinogenisis and Selectively Increase Apoptosis in UVB-Induced Skin Tumors in Mice, *PNAS*, 12455-12460 (2002).

"Epidermoid cyst," retrieved from the internet, http://en.wikipedia.org/wiki/Epidermoid_cyst. Retrieved on Mar. 22, 2010. pp. 1-2.

"Sun Can Harm You Most During Middle Part of the Day," *The Spectator*, p. K 03 (Jul. 6, 2002).

Kinjo et al., "Activity-Guided Fractionation of Green Tea Extract with Antiproliferative Activity Against Human Stomach Cancer Cells," *Biol. Pharm. Bull.*, 25(9):1238-1240 (2002).

"MTT assay," retrieved from the internet, http://en.wikipedia.org/wiki/MTT_assay. Retrieved on Mar. 22, 2010, pp. 1-2.

"Theacea," retrieved from the internet, http://en.wikipedia.org/wiki/Theaceae. Retrieved on Mar. 25, 2010, pp. 1-2.

WebMD. Retrieved from the internet, http://www.webmd.com/melanoma-skin-cancer-guide/protecting-you-skin-from-ultraviolet-radiation-and-skin-cancer. Retrieved on Mar. 22, 2010, pp. 1-4.

Merk. "Skin Disorders," retrieved from the internet, http:www///merk.com/mmhe/sec18.html. Retrieved on Mar. 22, 2010, pp. 1-2.

\* cited by examiner

UV/VIS Spectra of Extract of Cell Walls Fraction and Conventional Teas (Dilution 1:1000)

——— Black Tea Extract
·········· White Tea Extract
— — — Cell Walls Fraction Extract Absorbance Spectra of Extracts of Cell Walls Fraction and Conventional Teas Applied on Vitro-Skin®
(Dry Matter Levels are Equalized)

——— White Tea Extract
·········· Black Tea Extract
– – – Cell Walls Fraction Extract

BIOACTIVE COMPOSITIONS FROM THEACEA PLANTS AND PROCESSES FOR THEIR PRODUCTION AND USE

This application is a divisional of U.S. patent application Ser. No. 12/335,534, filed Dec. 15, 2008, issued as U.S. Pat. No. 8,043,635 on Oct. 25, 2011, which is a divisional of U.S. patent application Ser. No. 11/033,925, filed Jan. 12, 2005, issued as U.S. Pat. No. 7,473,435 on Jan. 6, 2009, which claims the priority benefit of U.S. Provisional Patent Application Ser. No. 60/535,861, filed Jan. 12, 2004, the disclosures of which are hereby incorporated herein by reference in their entirety.

FIELD OF THE INVENTION

The present invention relates to bioactive compositions, processes for their production from Theacea plants, and uses of these compositions.

BACKGROUND OF THE INVENTION

The Theacea (tea plants) family includes trees or shrubs comprising about 40 genera and 600 species. *Camellia sinensis* occupies a unique position in the Theacea family, because this particular species of plant is predominantly used as a single raw material source to produce all three basic kinds of tea: green tea, oolong tea, and black tea (collectively referred to herein as the "tea plant"). According to some sources, there is a fourth type of tea, i.e., the so-called "white tea," which is produced exclusively from the buds or tips of the tea plant.

The three basic forms of tea are determined by the degree of processing, which involves the identical tender young tea leaves. The leaves are plucked, sorted, cleaned, and variously oxidized before steaming or drying. The term "fermentation" is frequently used to describe the processing of tea, but the term "oxidation" is a much more accurate description of the chemical transformations which take place.

Although there are some variations in the processing, it is generally agreed that green tea has the lowest degree of oxidation and that black tea has the highest. Oolong tea is considered to be partially oxidized, and thus occupies the place between green and black tea. With respect to processing, there is very little difference (or no difference at all) between green and white tea.

Green tea is made from fresh leaves that are steamed and wilted, and then immediately dried. Black tea is made from leaves that are wilted and crushed in rollers, then allowed to oxidize for several hours before they are dried. Oolong tea comes from leaves that are only partially oxidized before drying.

Worldwide, tea is the second (after water) most commonly consumed liquid, and is the sixth (after water, soft drinks, coffee, beer, and milk) most commonly consumed liquid in the United States. Tea consumption continues to increase worldwide, especially due to the growing public awareness concerning health benefits of this liquid. There is a growing number of publications suggesting anti-angiogenic, anti-bacterial, anti-cancerogenic, anti-inflammatory, anti-mutagenic, anti-oxidant, anti-septic, and detoxifying properties of teas and their ingredients. The list of tea benefits also includes reduction of the risk of rheumatoid arthritis, lowering cholesterol levels, and anti-diabetic properties. Not all of these benefits have been proven to be statistically significant. Nevertheless, the very broad spectrum of tea benefits reflects the unique composition of the very powerful biologically active substances, which exist in fresh plant leaves and survive conventional tea processing.

In particular, fresh leaves of *Camellia sinensis* have been reported to contain 22.2% polyphenols, 17.2% protein, 4.3% caffeine, 27.0% crude fiber, 0.5% starch, 3.5% reducing sugars, 6.5% pectins, 2.0% ether extract, and 5.6% ash (Duke, J. A., *Handbook of Energy Crops* (1983), see www.hort.purdue.edu/newcrop/duke_energy/Camellia_sinensis.html). Per 100 g, the leaf is reported to contain 8.0 g $H_2O$, 24.5 g protein, 2.8 g fat, 58.8 g total carbohydrate, 8.7 g fiber, 5.9 g ash, 327 mg Ca, 313 mg P, 24.3 mg Fe, 50 mg Na, 2700 µg β-carotene equivalent, 0.07 mg thiamine, 0.8 mg riboflavin, 7.6 mg niacin, and 9 mg ascorbic acid. Another report tallies 8.0 g $H_2O$, 28.3 g protein, 4.8 g fat, 53.6 g total carbohydrate, 9.6 g fiber, 5.6 g ash, 245 mg Ca, 415 mg P, 18.9 mg Fe, 60 mg Na, 8400 µg β-carotene equivalent, 0.38 mg thiamine, 1.24 mg riboflavin, 4.6 mg niacin, and 230 mg ascorbic acid. Yet another gives 8.1 g $H_2O$, 24.1 g protein, 3.5 g fat, 59.0 g total carbohydrate, 9.7 g fiber, 5.3 g ash, 320 mg Ca, 185 mg P, 31.6 mg Fe, 8400 µg β-carotene equivalent, 0.07 mg thiamine, 0.79 mg riboflavin, 7.3 mg niacin, and 85 mg ascorbic acid (J. A. Duke and A. A. Atchley, "Proximate Analysis," In: Christie, B. R. (ed.), *The Handbook of Plant Science in Agriculture*, CRC Press, Inc., Boca Raton, Fla. (1984)).

Leaves also contain carotene, riboflavin, nicotinic acid, pantothenic acid, and ascorbic acid. Caffeine and tannin are among the more active constituents (Council for Scientific and Industrial Research, 1948-1976). Ascorbic acid, present in the fresh leaf, is destroyed in making black tea. Malic and oxatic acids occur, along with kaempferol, quercitrin, theophylline, theobromine, xanthine, hypoxanthine, adenine, gums, dextrins, and inositol. Chief components of the volatile oil (0.007-0.014% fresh weight of leaves) are hexenal, hexenol, and lower aldehydes, butyraldehyde, isobuteraldehyde, isovaleraldehyde, as well as n-hexyl, benzyl and phenylethyl alcohols, phenols, cresol, hexoic acid, n-octyl alcohol, geraniol, linalool, acetophenone, benzyl alcohol, and citral.

It was found that the fresh tea leaf has an unusually high level of flavanol group of polyphenols (catechins), which may reach up to 30% of leaf dry matter. Catechins include predominantly (−)-epicatechin, (−)-epicatechin gallate, (−)-epigallocatechin and (−)-epigallocatechin gallate. Additionally there are unique to tea 3-galloylquinic acid (theogallin) and unique amino acid theanine (5-N-ethylglutamine) (Duke, J. A., *Handbook of Energy Crops* (1983), see www.hort.purdue.edu/newcrop/duke_energy/Camellia_sinensis.html).

Tea leaves contain high levels of polyphenol-oxidase and peroxidase. The first enzyme catalyzes the aerobic oxidation of the catechins and this process is initiated when the integrity of the leaf cell structure is disrupted. Phenol-oxidase is responsible for generation of bisflavanols, theaflavins, epitheaflavic acids, and thearubigens, which constitute the largest mass of the extractable matter in black tea. Most of these compounds readily form complexes with caffeine, which has significant level (2-4% of dry matter) in fresh leaves. Peroxidase plays important role in generation of the above complexes with proanthocyanidins. The catechin quinones also initiate the formation of many of the hundreds of volatile compounds found in the black tea aroma fraction. Additionally, the transformation of relatively soluble glycosides to lower solubility aglycones takes place.

All complex cascades of the above processes are initiated by disruption of the leaf cell structure and are intensified with the time of oxidation. As result, the composition of black tea, which is usually processed with intensive rolling or cutting and relatively long time oxidation, is much more different than that of the fresh leaf. Although green tea (and white tea) is processed with minimum oxidation, and its composition more similar to that of fresh leaves, there are non-enzymatic and enzymatically catalyzed changes, which occur extremely rapidly following plucking, and new volatile substances that are produced during the drying stage. Thus, even relatively gentle green tea processing initiates certain departure from original fresh plant composition and can diminish the therapeutic value and other potential benefits of fresh tea plant leaves.

Numerous recent studies clearly demonstrate that therapeutic benefits of tea are decreased in the following sequence: white tea>green tea>oolong tea>black tea. Thus, exploration of fresh tea plants may prevent the degradation of specific activities, which are observed as a result of conventional tea processing. Fresh, tender *Camellia* leaves contain approximately 80% water. Swelling and dehydration of the cells is prevented by the cells' rigid cell walls. The disruption of the cell wall structure triggers the dehydration of fresh plant tissue followed by the sequence of unwanted physico-chemical and biochemical processes: osmotic shock, decompartmentalization and disruption of enzymes, hydrolysis and oxidation, polymerization of phenols, transformation of glycosides to aglycones, generation of products of Maillard reaction, isomerization, and microbial contamination. Therefore, fresh *Camellia* contains very broad spectrum of biologically active substances and only part of them became available during conventional extraction processes. Thus, only cell walls, catabolites, and stable metabolites can be extracted with boiled water to obtain tea drink or for extraction with different solvents to obtain limited parts of biologically active components (predominantly polyphenols and flavonoids).

In light of the potential of fresh tea leaves as sources of valuable therapeutic and other potentially beneficial bioactive compositions, exploration of fresh tea plants is needed to determine how to maximize their therapeutic and other potentially beneficial bioactive properties.

SUMMARY OF THE INVENTION

The present invention relates to a bioactive composition. In one embodiment, the bioactive composition includes an isolated bioactive fraction derived from a Theacea plant. Suitable bioactive fractions can include, without limitation, a cell walls fraction, a cell walls fraction extract, a membrane fraction, a membrane fraction extract, a cytoplasm fraction, a cytoplasm fraction extract, a cell juice serum, and/or combinations thereof.

The present invention also relates to a bioactive topical formulation suitable for topical application to a mammal. In one embodiment, the bioactive topical formulation includes a topically effective amount of the bioactive composition of the present invention. The bioactive topical formulation can further include a topically acceptable carrier.

The present invention also relates to a method for inhibiting inflammatory activity in skin tissue of a mammal. This method involves providing the bioactive composition according to the present invention. The method further involves applying the bioactive composition to the skin tissue in an amount effective to inhibit inflammatory activity in the skin tissue.

The present invention also relates to a method of protecting skin tissue of a mammal from ultraviolet light-induced damage. This method involves providing the bioactive composition of the present invention. The method further involves applying the bioactive composition to the skin tissue in an amount effective to reduce ultraviolet light-induced damage of the skin tissue and to prevent oxidative damage of the skin tissue.

The present invention also relates to a method for normalizing skin disorders in skin tissue of a mammal. This method involves providing the bioactive composition of the present invention. The method further involves applying the bioactive composition to the skin tissue in an amount effective to normalize a cell disorder in the skin tissue.

The present invention also relates to a method for isolating a bioactive fraction derived from cell juice of a Theacea plant. This method involves providing a Theacea plant. The Theacea plant is then separated into cell juice and a cell walls component. The cell juice is then treated under conditions effective to yield a bioactive fraction. Suitable bioactive fractions include, without limitation, a membrane fraction, a membrane fraction extract, a cytoplasm fraction, a cytoplasm fraction extract, and/or a cell juice serum. The bioactive fraction is then isolated from the treated cell juice. The present invention further relates to an isolated bioactive composition produced by this method.

The present invention also relates to a method for isolating a bioactive fraction derived from a cell walls component of a Theacea plant. This method involves providing a Theacea plant. The Theacea plant is then separated into cell juice and a cell walls component. The cell walls component is treated under conditions effective to yield a bioactive fraction. The bioactive fraction is then isolated from the treated cell walls component. The present invention further relates to an isolated bioactive fraction produced by this method.

The present invention is useful in addressing the deficiencies of conventional tea processing methods, particularly the inability of conventional tea processing to preserve a broad spectrum of potent bioactive compositions. As provided by the present invention, processing of fresh *Camellia* biomass without fermentation and excessive heat treatment can yield more powerful and diversified bioactive compositions than products of conventional tea processing.

DETAILED DESCRIPTION OF THE INVENTION

Figure 1:
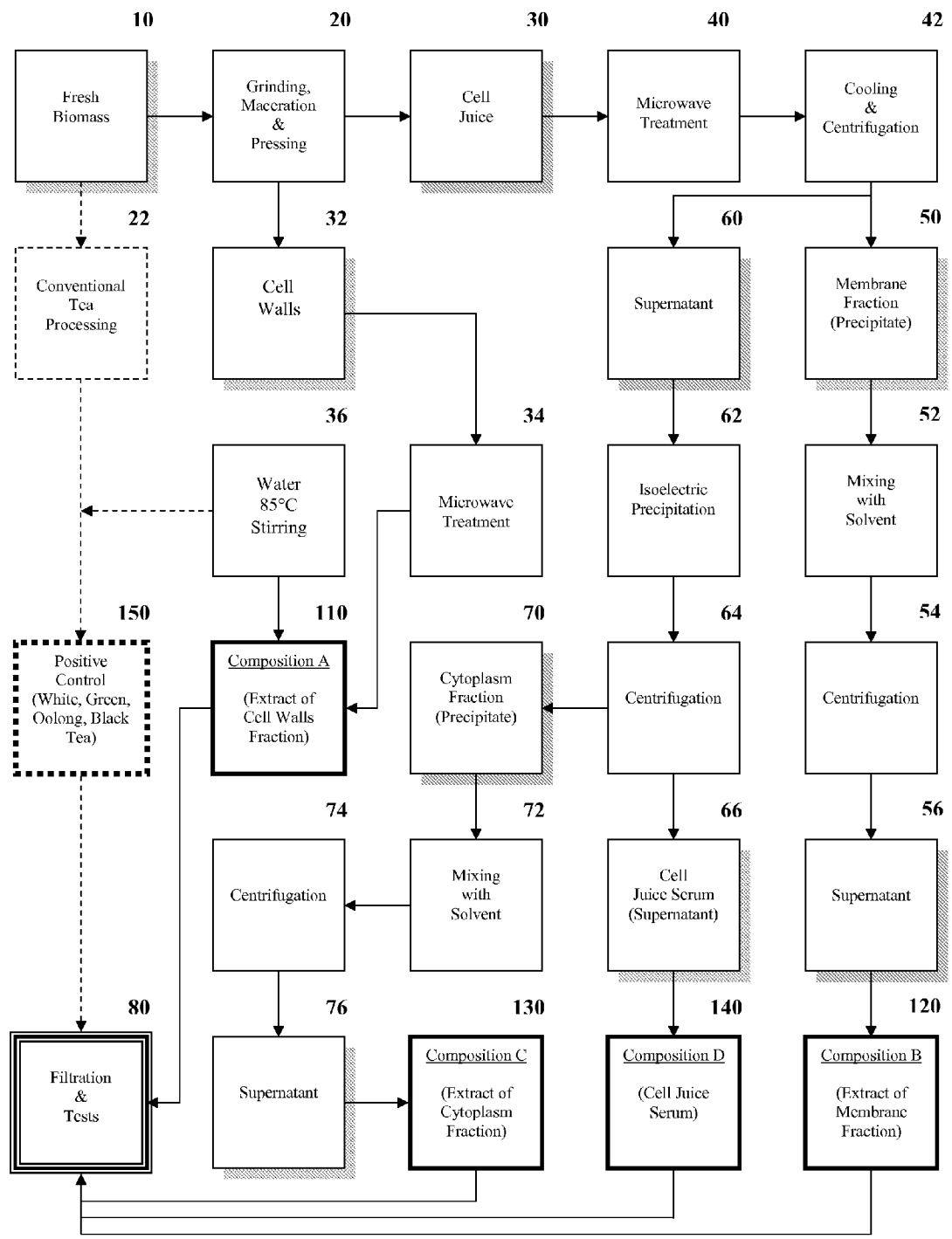
FIG. 1 is a schematic drawing demonstrating one embodiment of the process for preparing the bioactive compositions of the present invention.

The present invention relates to a bioactive composition. In one embodiment, the bioactive composition includes an isolated bioactive fraction derived from a Theacea plant. As used herein, the term "isolated bioactive fraction" is meant to include fractions that are isolated from a Theacea plant (e.g., fresh biomass of a Theacea plant) that has not undergone any conventional tea processing (e.g., heat treatment, oxidation, fermentation, drying). Suitable isolated bioactive fractions can include, without limitation, a cell walls fraction, a cell walls fraction extract, a membrane fraction, a membrane fraction extract, a cytoplasm fraction, a cytoplasm fraction extract, a cell juice serum, and/or combinations thereof.

The bioactive compositions and bioactive fractions of the present invention can have various catechin profiles and total catechin content amounts, as defined below, and as determined using conventional catechin diagnostic methods well known in the art. As used herein, the term "catechin" generally refers to all catechins, including, but not limited to, the following specific types of catechins: (i) (−)-epigallocatechin (see CAS No. 970-74-1, which is hereby incorporated by reference in its entirety); (ii) (+)-catechin (see CAS No. 7295-85-4, which is hereby incorporated by reference in its entirety); (iii) (−)-epicatechin (see CAS No. 490-46-0, which is hereby incorporated by reference in its entirety); (iv) (−)- epigallocatechin gallate (see CAS No. 989-51-5, which is hereby incorporated by reference in its entirety); (v) (−)-gallocatechin gallate (see CAS No. 4233-96-9, which is hereby incorporated by reference in its entirety); and (vi) (−)-epicatechin gallate (see CAS No. 1257-08-5, which is hereby incorporated by reference in its entirety). "Total catechin content" (as used herein) refers to the combined content level of all catechins contained in a particular bioactive composition or bioactive fraction of the present invention, and is not meant to be limited to the content levels of just the specific types of catechins listed herein above. As used herein, the term "catechin content profile" is used to describe the amounts of selected catechins contained in a particular bioactive composition or bioactive fraction of the present invention.

In one embodiment of the bioactive composition of the present invention, the bioactive fraction can be a cell walls fraction.

In one embodiment of the bioactive composition of the present invention, the bioactive fraction can be a cell walls fraction extract. In a specific embodiment of the present invention, the cell walls fraction extract can have a total catechin content of between about 2.1 and about 4.5 milligrams per gram of dry matter, particularly between about 2.6 and about 4.0 milligrams per gram of dry matter, and more particularly between about 3.0 and about 3.6 milligrams per gram of dry matter. In another specific embodiment, the cell walls fraction extract can have a catechin content profile as follows: (i) between about 2.0 and about 3.0 milligrams of (+)-catechin per gram of dry matter of the cell walls fraction extract; (ii) between about 0.005 and about 0.02 milligrams of (−)-epicatechin per gram of dry matter of the cell walls fraction extract; (iii) between about 0.005 and about 0.02 milligrams of (−)-epigallocatechin gallate per gram of dry matter of the cell walls fraction extract; and (iv) between about 0.003 and about 0.01 milligrams of (−)-epicatechin gallate per gram of dry matter of the cell walls fraction extract. More particularly, the cell walls fraction extract can have a catechin content profile as follows: (i) between about 2.2 and about 2.7 milligrams of (+)-catechin per gram of dry matter of the cell walls fraction extract; (ii) between about 0.01 and about 0.015 milligrams of (−)-epicatechin per gram of dry matter of the cell walls fraction extract; (iii) between about 0.01 and about 0.015 milligrams of (−)-epigallocatechin gallate per gram of dry matter of the cell walls fraction extract; and (iv) between about 0.005 and about 0.007 milligrams of (−)-epicatechin gallate per gram of dry matter of the cell walls fraction extract.

In one embodiment of the bioactive composition of the present invention, the bioactive fraction can be a membrane fraction.

In one embodiment of the bioactive composition of the present invention, the bioactive fraction can be a membrane fraction extract. In a specific embodiment of the present invention, the membrane fraction extract can have a total catechin content of between about 15.0 and about 30.5 milligrams per gram of dry matter, particularly between about 18.0 and about 27.5 milligrams per gram of dry matter, and more particularly between about 21.0 and about 24.5 milligrams per gram of dry matter. In another specific embodiment, the membrane fraction extract can have a catechin content profile as follows: (i) between about 1.7 and about 3.3 milligrams of (−)-epigallocatechin per gram of dry matter of the membrane fraction extract; (ii) between about 6.1 and about 10.2 milligrams of (+)-catechin per gram of dry matter of the membrane fraction extract; (iii) between about 0.3 and about 1.1 milligrams of (−)-epicatechin per gram of dry matter of the membrane fraction extract; (iv) between about 6.2 and about 12.5 milligrams of (−)-epigallocatechin gallate per gram of dry matter of the membrane fraction extract; (v) between about 0.007 and about 0.03 milligrams of (−)-gallocatechin gallate per gram of dry matter of the membrane fraction extract; and (vi) between about 1.3 and about 3.3 milligrams of (−)-epicatechin gallate per gram of dry matter of the membrane fraction extract. More particularly, the membrane fraction extract can have a catechin content profile as follows: (i) between about 2.0 and about 3.0 milligrams of (−)-epigallocatechin per gram of dry matter of the membrane fraction extract; (ii) between about 7.0 and about 9.0 milligrams of (+)-catechin per gram of dry matter of the membrane fraction extract; (iii) between about 0.5 and about 0.9 milligrams of (−)-epicatechin per gram of dry matter of the membrane fraction extract; (iv) between about 8.0 and about 10.0 milligrams of (−)-epigallocatechin gallate per gram of dry matter of the membrane fraction extract; (v) between about 0.01 and about 0.02 milligrams of (−)-gallocatechin gallate per gram of dry matter of the membrane fraction extract; and (vi) between about 1.8 and about 2.8 milligrams of (−)-epicatechin gallate per gram of dry matter of the membrane fraction extract.

In one embodiment of the bioactive composition of the present invention, the bioactive fraction can be a cytoplasm fraction.

In one embodiment of the bioactive composition of the present invention, the bioactive fraction can be a cytoplasm fraction extract.

In one embodiment of the bioactive composition of the present invention, the bioactive fraction can be a cell juice serum. In a specific embodiment, the cell juice serum can have a total catechin content of between about 8.0 and about 20.0 milligrams per gram of dry matter, particularly between about 10.0 and about 18.0 milligrams per gram of dry matter, and more particularly between about 12.0 and about 16.0 milligrams per gram of dry matter. In another specific embodiment, the cell juice serum can have a catechin content profile as follows: (i) between about 2.1 and about 4.4 milligrams of (−)-epigallocatechin per gram of dry matter of the cell juice serum; (ii) between about 4.2 and about 8.6 milligrams of (+)-catechin per gram of dry matter of the cell juice serum; (iii) between about 0.2 and about 2.0 milligrams of (−)-epicatechin per gram of dry matter of the cell juice serum; (iv) between about 1.2 and about 3.2 milligrams of (−)-epigallocatechin gallate per gram of dry matter of the cell juice serum; (v) between about 0.01 and about 0.1 milligrams of (−)-gallocatechin gallate per gram of dry matter of the cell juice serum; and (vi) between about 0.2 and about 1.3 milligrams of (−)-epicatechin gallate per gram of dry matter of the cell juice serum. More particularly, the cell juice serum can have a catechin content profile as follows: (i) between about 3.0 and about 3.5 milligrams of (−)-epigallocatechin per gram of dry matter of the cell juice serum; (ii) between about 5.0 and about 7.0 milligrams of (+)-catechin per gram of dry matter of the cell juice serum; (iii) between about 0.7 and about 1.5 milligrams of (−)-epicatechin per gram of dry matter of the cell juice serum; (iv) between about 1.7 and about 2.7 milligrams of (−)-epigallocatechin gallate per gram of dry matter of the cell juice serum; (v) between about 0.03 and about 0.07 milligrams of (−)-gallocatechin gallate per gram of dry matter of the cell juice serum; and (vi) between about 0.5 and about 1.0 milligrams of (−)-epicatechin gallate per gram of dry matter of the cell juice serum.

In one embodiment, fresh biomass of Theacea plants can be used to isolate the bioactive compositions of the present invention. The fresh biomass can be taken from Theacea plants that are of the *Camellia* and/or *Eurya* genera. Suitable species of the *Camellia* genus for use in the present invention can include, without limitation, *Camellia sinensis, Camellia japonica, Camellia reticulate*, and *Camellia sasanqua*. Suitable species of the *Eurya* genus for use in the present invention can include, without limitation, *Eurya sandwicensis*.

The bioactive composition of the present invention can further include a stabilizing agent. Suitable stabilizing agents are those that are commonly used in the art. Particular suitable stabilizing agents can include, without limitation, an emulsifier, a preservative, an anti-oxidant, a polymer matrix, and/or mixtures thereof.

In one aspect of the present invention, the bioactive fraction can have modulatory activity on at least one mammal cell function. Such modulatory activity can include, for example, cell growth inhibition activity, cell growth stimulation activity, enzyme secretion activity, enzyme inhibition activity, anti-oxidant activity, UV-protection activity, anti-inflammatory activity, wound healing activity, and/or combinations of these activities. With respect to cell growth inhibition activity, such activity can involve growth inhibition of cancer cells. Suitable cancer cells that can be inhibited to grow by the bioactive fractions of the present invention can include, without limitation, breast cancer cells and/or colon cancer cells. The described cell growth inhibition activity can also include growth inhibition of leukemia cells. Suitable leukemia cells that can be inhibited to grow by the bioactive fractions of the present invention can include, without limitation, monocytic leukemia cells.

In another embodiment, the bioactive composition can be effective in inhibiting unwanted hyper-proliferation or hypo-proliferation of skin cells and/or inhibiting unwanted uncoordinated enzyme activities or enzyme secretion processes in the skin cells.

In another embodiment, the bioactive composition of the present invention can further include a delivery system for systemic or topical administration that are commonly used in the art.

The present invention also relates to a bioactive topical formulation suitable for topical application to a mammal. In one embodiment, the bioactive topical formulation includes a topically effective amount of the bioactive composition of the present invention. The bioactive topical formulation can further include a topically acceptable carrier. Suitable topically acceptable carriers can include, without limitation, a hydrophilic cream base, a hydrophilic lotion base, a hydrophilic surfactant base, a hydrophilic gel base, a hydrophilic solution base, a hydrophobic cream base, a hydrophobic lotion base, a hydrophobic surfactant base, a hydrophobic gel base, and/or a hydrophobic solution base. In one embodiment, the bioactive composition can be present in an amount ranging from between about 0.001 percent and about 90 percent of the total weight of the bioactive topical formulation.

The present invention also relates to a method for inhibiting inflammatory activity in skin tissue of a mammal. This method involves providing the bioactive composition according to the present invention. The method further involves applying the bioactive composition to the skin tissue in an amount effective to inhibit inflammatory activity in the skin tissue. In one embodiment of this method, the bioactive composition can further include a stabilizing agent (suitable examples of which are as described herein). In another embodiment of this method, the bioactive composition can further include a topically acceptable carrier (suitable examples of which are as described herein).

The present invention also relates to a method of protecting skin tissue of a mammal from ultraviolet light-induced damage. This method involves providing the bioactive composition of the present invention. The method further involves applying the bioactive composition to the skin tissue in an amount effective to reduce ultraviolet light-induced damage of the skin tissue and to prevent oxidative damage of the skin tissue. In one embodiment, the method is useful in protecting skin tissue from ultraviolet light-induced damage caused by ultraviolet light in a range of between about 320 and about 400 nanometers. In another embodiment of this method, the bioactive composition can further include a stabilizing agent (suitable examples of which are as described herein). In another embodiment of this method, the bioactive composition can further include a topically acceptable carrier (suitable examples of which are as described herein).

The present invention also relates to a method for normalizing skin disorders in skin tissue of a mammal. This method involves providing the bioactive composition of the present invention. The method further involves applying the bioactive composition to the skin tissue in an amount effective to normalize a cell disorder in the skin tissue. In one embodiment of this method, the bioactive composition can further include a stabilizing agent (suitable examples of which are as described herein). In another embodiment of this method, the bioactive composition can further include a topically acceptable carrier (suitable examples of which are as described herein).

The present invention also relates to a method for isolating a bioactive fraction derived from cell juice of a Theacea plant. This method involves providing a Theacea plant (e.g., in the form of fresh biomass). Suitable Theacea plants for use in this method are as described herein, supra. The Theacea plant (e.g., fresh biomass) is then separated into cell juice and a cell walls component. The cell juice is then treated under conditions effective to yield a bioactive fraction. Suitable bioactive fractions include, without limitation, a membrane fraction, a membrane fraction extract, a cytoplasm fraction, a cytoplasm fraction extract, and/or a cell juice serum. The bioactive fraction is then isolated from the treated cell juice. In one embodiment, the various suitable bioactive fractions produced by this method are as described herein. The present invention further relates to an isolated bioactive composition produced by this method.

The present invention also relates to a method for isolating a bioactive fraction derived from a cell walls component of a Theacea plant. This method involves providing a Theacea plant (e.g., in the form of fresh biomass). The Theacea plant (e.g., fresh biomass) is then separated into cell juice and a cell walls component. The cell walls component is treated under conditions effective to yield a bioactive fraction. The bioactive fraction is then isolated from the treated cell walls component. In one embodiment, the various suitable bioactive fractions produced by this method are as described herein. The present invention further relates to an isolated bioactive fraction produced by this method.

By way of example, the overall process for preparing the bioactive fractions of the present invention (as described herein above) is schematically shown in FIG. 1. Details of the processing steps are further described in the Examples (infra). As depicted in FIG. 1, fresh biomass 10 (e.g., fresh plant biomass) of Theacea plants is subjected to grinding, maceration, and pressing 20 under conditions effective to destroy rigid cell walls, and thereby to yield plant cell juice 30 and cell walls 32. The fresh biomass 10 is also used for conventional tea processing 22 to produce positive control 150 for comparative testing and evaluation. Cell juice 30 is subjected to coagulation 40 (e.g., microwave treatment) to achieve quantitative coagulation of membrane fraction components of fresh plant biomass 10. Coagulation 40 is sufficient to enable subsequent separation of the coagulated membrane fraction from other non-coagulated components of cell juice 30. As shown in FIG. 1, one embodiment of such separation is achieved by cooling and centrifugation 42 to yield membrane fraction (precipitate) 50 and supernatant 60, which is free from specific chloroplast membrane components such as chlorophyll and phospholipids.

To produce the cell walls fraction extract (i.e., Composition A 110), cell walls 32 are subjected to drying 34 (e.g., several subsequent microwave treatments) and then mixing the dried material with water 36 under conditions commonly used to prepare conventional teas (e.g., mixing in water at 85° C.).

To produce the membrane fraction extract (i.e., Composition B 120), membrane fraction 50 is subjected to mixing with solvent 52 and then centrifugation 54 to yield supernatant 56 and Composition B 120.

To produce the cytoplasm fraction extract (i.e., Composition C 130), supernatant 60 is subjected to coagulation 62 (e.g., isoelectric precipitation) and centrifugation 64 to yield cytoplasm fraction (precipitate) 70 containing most of the soluble cytoplasm proteins. Cytoplasm fraction (precipitate) 70 is then subjected to mixing with solvent 72, followed by centrifugation 74 to yield supernatant 76 and then Composition C 130.

To produce cell juice serum (i.e., Composition D 140), supernatant 60 is subjected coagulation 62 (e.g., isoelectric precipitation) and centrifugation 64 to yield cell juice serum (supernatant) 66 and then Composition D 140.

Conventional tea processing 22 of fresh biomass 10 is used to produce, for example, positive control 150 (of various teas, including, for example, white, green, oolong, and black teas).

Composition A 110, Composition B 120, Composition C 130, Composition D 140, and positive control 150 can then be used for filtration and tests 80.

The present invention also relates to a device for selectively dispersing into a liquid low molecular weight and reduced, non-oxidized components of a bioactive composition. In one embodiment, the device includes a bioactive composition of the present invention. The bioactive composition can be enclosed in a filtering pouch. A suitable filtering pouch can be one that is effective in selectively dispersing into a liquid the low molecular weight and reduced, non-oxidized components of the bioactive composition. In one embodiment, the pouch includes a selective membrane that allows dispersal of the low molecular weight and reduced, non-oxidized components of bioactive compositions from within the pouch into the liquid, but where the membrane inhibits dispersal of high molecular weight and oxidized components from within the pouch into the liquid. As used herein, the term "low molecular weight and reduced, non-oxidized components" include components of the bioactive composition of the present invention that are less than or equal to about 5,000 Daltons. In one embodiment of this method, the bioactive composition can further include a stabilizing agent (suitable examples of which are as described herein). In another embodiment of this method, the bioactive composition can further include a topically acceptable carrier (suitable examples of which are as described herein).

The present invention also relates to a method of making a therapeutic beverage containing low molecular weight and reduced, non-oxidized bioactive compositions. This method involves providing a device produced according to the method of the present invention. The device is contacted with a liquid under conditions effective to cause the low molecular weight and reduced, non-oxidized components of the bioactive compositions to disperse into the liquid. In one embodiment of this method, the bioactive composition can further include a stabilizing agent (suitable examples of which are as described herein). In another embodiment of this method, the bioactive composition can further include a topically acceptable carrier (suitable examples of which are as described herein). A suitable liquid for use in this method can include, without limitation, water. The water can be hot or cold. The present invention further relates to a therapeutic beverage produced according to this method.

EXAMPLES

Example 1

Preparation of Bioactive Compositions Derived from *Camellia sinensis* Plants

A schematic of one embodiment of the method of preparing the bioactive compositions of the present invention is shown in FIG. 1. Below is a description of relevant aspects of one embodiment of the method of the present invention.

Biomass Preparation. Sufficient amounts of fresh *Camellia* (*Camellia sinensis*) plant biomass (only top tender young leaf tissue with buds) were harvested to yield approximately 100 kg of dry matter. The level of dry matter in the fresh biomass was calculated to be 21.70%, requiring harvesting of approximately 461 kg of fresh plant biomass to yield 100 kg of dry matter. Care was taken to preserve the inherent moisture content of the plant biomass and to avoid wilting due to moisture loss. The harvesting was conducted in such a manner as to avoid or minimize chopping, mashing, and crushing of the collected biomass to avoid the disruption of the leaf cell structure, which triggers the endogenous enzymatic reactions catalized by phenol-oxidase and peroxidase. Because these reactions are intensified with the time of oxidation, all steps were completed in the shortest possible period of time. For example, the harvested biomass was delivered for processing not more than 10 minutes after cutting. This was done to minimize exposure of the plant biomass to sun, high temperature, and other negative environmental factors. A washing step was performed to remove soil particles and other debris from the plants prior to further processing. This washing was accomplished by washing the harvested plants for $\leq 5$ minutes in $\leq 1$ kg/cm$^2$ water pressure. The residual water wash did not contain any green or brown pigments, indicating proper water pressure and washing duration. The excess water was removed from the washed plant biomass.

Grinding, Maceration, and Pressing of Plant Biomass. After harvesting, collecting, and washing the plant biomass, the plants then underwent grinding, maceration, and pressing to extract the intracellular content (i.e., the plant cell juice) and to separate it from the fiber-enriched cell walls fraction (cell walls fraction). A hammer mill (Model VS 35, Vincent Corporation, FL) having 10 HP engine and set of screens was used to grind the biomass to yield plant tissue particles of suitably small size in a shortest amount of time and without significant increase of biomass temperature. The hammer mill was set to produce the maximum size of macerated plant particles of $\leq 0.5$ centimeters during $\leq 10$ seconds of treatment. The biomass temperature was increased only $\leq 5°$ C. A horizontal continuous screw press (Compact Press "CP-6", Vincent Corporation, FL) was immediately used to extract the plant cell juice from the plant. The pressure on the cone of the screw press was maintained at a level of 24 kg/cm$^2$, with a screw speed of 12 rpm and only a temperature increase of $\leq 5°$ C. This treatment yielded the 185 kg of cell walls fraction having dry matter level 41.39% and 276 kg of plant cell juice having dry mater level 8.49%.

Preparation of Cell Walls Fraction Extract (Composition A). The aliquot of cell walls fraction having initial dry matter level 41.39% was dried in microwave hood combination (Model GH9115XE, Whirlpool) during 30 sec and then cooled during 30 sec. This treatment was repeated several times till dry matter level in cell walls fraction reached 96.52%. The 66.01 of deionized water having temperature 85° C. were added to 4.0 kg of dry cell walls fraction and steer with high agitation for 5 min. These conditions are in agreement with tea preparation procedure, which is described in D'Amelio, F. S., *Botanicals. A Phytocosmetic Desk Reference*, Boca Raton, London, New York, Washington, D.C.: CRC Press, p. 361 (1999), which is hereby incorporated by reference in its entirety (see also the discussions at www.leaftea.com; www.divinitea.com; www.equatorcoffee.com, which are hereby incorporated herein in their entirety). The mixture was filtered through 4-layers of nylon fabric and then through the filter having 0.8 µm porous. The pH of obtained cell walls extract was equal 5.24 and dry matter level was equal 0.84%. This extract was further used for tests of its activities.

Separation of the Membrane Fraction from the Cell Juice. The initial plant cell juice having dry matter level 8.49% contained small fiber particles, which were removed by filtration through four layers of nylon fabric or by using low-speed centrifugation biomass. The filtered plant cell juice was exposed to microwave treatment using a temperature probe control. This treatment continued until the temperature of the cell juice reached 60° C. Once coagulation was induced, the treated cell juice was immediately cooled to 40° C. Separation of the membrane fraction from the coagulated cell juice was achieved using centrifugation at greater than or equal to 3,000 g for greater than or equal to 20 minutes. This yielded a membrane fraction (precipitate) and a cell juice supernatant, which contained a cytoplasm fraction and a cell serum fraction (i.e., low molecular weight soluble components). The membrane fraction having dry mater level 32.89% was used in preparing the extract of membrane-derived bioactive composition. The cell juice supernatant was used for further processing to yield cytoplasm fraction and cell juice serum.

Preparation of the Membrane Fraction Extract (Composition B). One part of membrane fraction (10.0 kg) and two parts of Dimethyl Sulfoxide—(20.0 kg) were mixed at room temperature for 1 hour with permanent stirring. Then material was centrifuged at greater than or equal to 4,000 g for greater than or equal to 45 minutes. The precipitate was discarded and supernatant was filtered through the filter having 0.8 µm porous. This filtrate having dry meter level 6.83%—membrane fraction extract (composition B) was used for further tests of its activities.

Separation of the Cytoplasm Fraction from the Cell Juice Supernatant. In order to separate out the cytoplasm fraction, the cell juice supernatant was subjected to isoelectric precipitation. Precipitation of the cytoplasm fraction was induced using a titration method utilizing 5.0 N Hydrochloric Acid (HCl) to bring the pH of the cell juice supernatant to 4.0. The separation of precipitated cytoplasm fraction having dry matter level 14.5% from supernatant was achieved by centrifugation at greater than or equal to 3,000 g for greater than or equal to 20 minutes.

Preparation of the Extract of Cytoplasm Fraction (Composition C). One part of cytoplasm fraction (10.0 kg) and two parts of Dimethyl Sulfoxide—(20.0 kg) were mixed at room temperature for 1 hour with permanent stirring. Then material was centrifuged at greater than or equal to 4,000 g for greater than or equal to 45 minutes. The precipitate was discarded and supernatant was filtered through the filter having 0.8 µm porous. This filtrate having dry meter level 3.50%—extract of cytoplasm fraction (composition C) can be used for further tests of its activities.

Preparation of Cell Juice Serum (Composition D). After separation of cytoplasm fraction the supernatant contained suspended particles. In order to separate out these particles, the supernatant was centrifuged at greater than or equal to 7,500 g for greater than or equal to 30 minutes. The transparent supernatant—cell juice serum was filtered through the filter having 0.8 µm porous. This filtrate (composition D) having dry matter level 5.69% was used for further tests of its activities.

Preparation of Conventional Tea Extracts—Controls. The same lot of fresh *Camellia* leaves, which was used to preparation of compositions A, B, C and D was used to produce conventional white and black tea.

The following procedure was used to produce white tea. The fresh biomass contained 21.70% dry matter was placed for 20 sec in boiling water to inactivate endogenous enzymes—phenol-oxidase and peroxidase. During this procedure the leaves were kept in the nylon screen bag. Then treated leaves were dried in microwave during 30 sec and then cooled during 30 sec. This treatment was repeated several times until dry matter level in biomass reached 93.74%. Then 66.01 of deionized water having temperature 85° C. were added to 4.0 kg of dry leaves and steer with high agitation for 5 min. These conditions are in agreement with tea preparation procedure, which is described in D'Amelio, F. S., *Botanicals. A Phytocosmetic Desk Reference*, Boca Raton, London, New York, Washington, D.C.: CRC Press, p. 361(1999), which is hereby incorporated by reference in its entirety (see also the discussions at www.leaftea.com; www.divinitea.com; and www.equatorcoffee.com, which are hereby incorporated by reference in their entirety). The mixture was filtered through 4-layers of nylon fabric and filtered through the filter having 0.8 µm porous. The pH of obtained cell walls fraction extract was equal 5.52 and dry matter level was equal 1.10%. This extract was further used for tests of its activities.

The following procedure was used to produce black tea. The fresh biomass contained 21.70% dry matter was kept at 25° C. with periodical (1 hour "on" and 1 hour "off") aeration until dry matter level reached 35%. Then leaves were ground (crushed) to the particles having size 2-3 mm. This procedure leads to increase of biomass temperature to approximately 30° C. The ground biomass was placed in the form of layer (2" high) on plastic conveyor belt for fermentation (oxidation) during 90 min at 25° C. The fermented biomass, which acquired the brown color was dried at 130° C. for 30 min to reach the dry matter level 97.5%. Then 66.01 of deionized water having temperature 85° C. were added to 4.0 kg of dry leaves and steer with high agitation for 5 min. These conditions are in agreement with tea preparation procedure which is described in D'Amelio, F. S., *Botanicals. A Phytocosmetic Desk Reference*, Boca Raton, London, New York, Washington, D.C.: CRC Press, p. 361 (1999), which is hereby incorporated by reference in its entirety (see the discussions at www.leaftea.com; www.divinitea.com; www.equatorcoffee.com, which are hereby incorporated by reference in their entirety). The mixture was filtered through 4-layers of nylon fabric and filtered through the filter having 0.8 µm porous. The pH of obtained cell walls fraction extract was equal 4.96 and dry matter level was equal 1.38%. This extract was further used for tests of its activities.

Example 2

Distribution of Dry Matter Regarding Preparation of Bioactive Compositions from *Camellia sinensis, Camellia japonica, Camellia reticulate, Camellia sasanqua*, and *Eurya sandwicensis*

Various fractions collected during the production of bioactive compositions were analyzed and compared for dry matter distribution. Table 1 shows the distribution of 100 kg dry mater among products of fractionation of tea plants. It was determined that the process of the present invention permits extracted yield conversion into plant cell juices in the range of from about 20 to 30% of initial biomass dry matter. The yield of membrane fractions' dry matter was in the range from 5% to 10% of initial biomass dry matter and from 25% to 35% of cell juice dry matter. Table 1 shows that the yields of cytoplasm fractions dry matter did not exceed 1.0% of initial biomasses dry matter and subsequently 2.5% of cell juice supernatant dry matter. Most of cell juice supernatant dry matter was concentrated in cell juice serum. The cell walls fraction, membrane fraction and cytoplasm fraction were used as the sources for preparation of their extracts, which are categorized as bioactive compositions. The cell juice serum was directly used "as is" as subsequent bioactive composition having no exogenous solvents.

TABLE 1

Distribution of 100 kg Dry Matter Among Products of Fractionation of Fresh Biomass

| Product | Plant Source *Camellia sinensis* |
| --- | --- |
| Initial Biomass | 100.0 |
| Cell Walls Fraction | 76.6 |
| Cell Juice | 23.4 |
| Membrane Fraction | 6.5 |
| Cytoplasm Fraction | 0.6 |
| Cell Juice Serum | 16.3 |

It should be noted that the three selected materials are the most diversified representation of all functional structures, which exists in fresh plant tissue. Only soluble cell juice serum has physico-chemical properties, which allows the direct administration to the commonly used in vitro testing systems. The cell walls fraction, membrane fraction and cytoplasm fraction were used as raw materials for extraction with solvents. Because cell walls fraction is structurally similar to conventional tea plant products, this fraction was extracted with water to provide the best comparison with conventional teas. The membrane fraction was extracted with Dimethyl Sulfoxide, which facilitates the effective solubilization of both hydrophobic and hydrophilic components integrated in chloroplast and mitochondria structures. The cytoplasm fraction was extracted with water. The cell juice serum was used "as is."

Table 2 shows the yield of all four tested bioactive compositions: cell walls fraction extract (composition A), membrane fraction extracts (composition B), extract of cytoplasm fraction (composition C), cell juice serum (composition D) and controls—white tea extract or black tea extract from 100 kg of initial biomass dry mater.

TABLE 2

Yield of Bioactive Compositions from 100 kg of Initial Biomass

| Product | Plant Source *Camellia sinensis* |
| --- | --- |
| Initial Biomass | 100.0 |
| Composition A (Cell Walls Fraction Extract) | 14.35 |
| Composition B (Membrane Fraction Extract) | 2.37 |
| Composition C (Cytoplasm Fraction Extract) | 0.2 |
| Composition D (Cell Juice Serum) | 16.3 |
| Control (Extract of White Tea or Black Tea) | 15.14 ... 19.36 |

Table 2 shows that the total yield of bioactive compositions A, B, C and D from 100 kg of dry matter of *Camellia sinensis* equals 33.3%, which very significantly exceeds the yield of conventional tea process—15.14 ... 19.36%.

Example 3

Comparison of Composition A (Cell Walls Fraction Extract) and Conventional Tea Extracts Various parameters of bioactive composition A and conventional white and black tea extracts obtained from the same batch of fresh *Camellia sinensis* were measured and subsequent results of these are presented in Table 3 (The used experimental methods are described in Examples 9 and 20, and in the U.S. Patent Application Publication No. 2003/0175235, which is hereby incorporated by reference in its entirety).

TABLE 3

Various Parameters of Bioactive Composition A and Extracts of White and Black Teas.

| Parameter | Extract of Cell Walls Fraction (Composition A) | Controls Extract of White Tea | Extract of Black Tea |
| --- | --- | --- | --- |
| Dry Matter, % | 0.84 | 1.10 | 1.38 |
| pH | 5.24 | 5.52 | 4.96 |
| Conductivity, mS/cm | 1.57 | 2.23 | 5.32 |
| Total Dissolved Solids, g/L | 0.78 | 1.23 | 2.71 |
| Redox Potential, mV | 123 | 159 | 188 |
| Area under the Spectra Curve (ASC) 200-450 nm, Abs · nm | 5.727 | 6.604 | 4.616 |
| ASC: Dry Matter | 6.818 | 6.004 | 3.345 |
| Superoxide Scavenging Activity ($ICR_{50}$), µg DM/ml | 26.3 | 114.5 | 227.1 |
| Color (1 ... 10 scale) | 9.6 | 4.7 | 7.5 |
| Flavor (1 ... 10 scale) | 9.3 | 6.1 | 6.6 |
| Mouthfeel (1 ... 10 scale) | 9.4 | 6.5 | 5.3 |

Table 3 shows that cell walls fraction extract has lower levels of dry matter, electrolytes and dissolved solids compare to conventional white and black tea extracts. The UV/VIS spectral data show that cell walls fraction extract has the highest specific value of the area under the spectra curve, i.e. this particular *Camellia* product (composition A) has the highest level of optically active constituents per unit of dry matter. Additionally, the cell walls fraction extract has the lower amount of redox potential, which indicates that this composition is less oxidized then conventional white and black tea extracts. The cell walls fraction extract demonstrated superoxide scavenging activity, resulting in 50% inhibition of cytochrome c reduction ($ICR_{50}$) at a much lower concentration then white and black tea extracts. A Qualitative Descriptive Analysis ("QDA") test method was selected to systematically characterize and quantify teas based on color, flavor, and mouthfeel, which govern acceptability of tea beverages. The QDA method employs a trained panel of expert tasters to quantify the above attributes of tea beverages relative to defined reference standards. The comparative evaluation of the color, flavor and mouthfeel of teas demonstrated that cell walls fraction extract significantly exceed the same characteristics of conventional teas.

Thus, cell walls fraction, which was obtained from fresh *Camellia* biomass without any fermentation (oxidation) and heat treatment, is distinct from all other teas (Wilson et al., eds., *Tea: Cultivation to Consumption*, London: Chapman Hall (1992), which is hereby incorporated by reference in its entirety). Additionally, the key *Camellia* enzymes (phenoloxidase and peroxidase) always remain within conventional teas. Instead, the present invention includes separation of fresh *Camellia* leaves to cell walls fraction and cell juice, which is enriched by these enzymes and thus cell walls fraction does not contain endogenous phenol-oxidase and peroxidase. Therefore, cell walls fraction must be categorized as a new tea category having fundamental differences compared with white, green, oolong, and black teas. This novel cell walls fraction tea can be used in either loose or bag form or other manifestations to prepare a broad spectrum of drinks, beverages, and additives to nutriceutical and functional food products.

Example 4

Preparation of Bioactive Compositions for Different Applications

All bioactive compositions can be used as solutions, suspensions, dispersions, pastes or dried powders incorporated into a variety of formulations for systemic or topical administrations. The solubilized forms of compositions can be filtrated through filters having the 0.2 μm porous to completely remove non-completely solubilized small particles and endogenous microorganisms. The dry matter level in bioactive compositions before and after sterilized filtration is presented in Table 4.

TABLE 4

Level of Dry Matter in Bioactive Compositions Before (numerator) and After (denominator) Sterilized Filtration

| Product | Plant Source *Camellia sinensis* |
|---|---|
| Composition A | 0.84 |
| (Extract of Cell Walls Fraction) | 0.72 |
| Composition B | 6.83 |
| (Extract of Membrane Fraction) | 6.12 |
| Composition D | 5.69 |
| (Cell Juice Serum) | 5.59 |
| Control | 1.10 |
| (Extract of White Tea) | 1.03 |

Table 4 shows that dry matter levels in all bioactive compositions were decreased after sterilizing filtration. However this decrease did not lead to any loss or significant reduction of their biological activities and was in the range 2-14%. Therefore major part of compositions is presented by soluble bioactive ingredients.

Fresh *Camellia* leaves contain relatively low molecular weight (reduced, non-oxidized) ingredients. As a result of oxidation and polymerization processes in the manufacturing of conventional teas the above potent ingredients are transformed into the parts of high molecular weight substances having relatively low activity.

The bioactive compositions of the present invention are obtained without fermentation (oxidation) and excessive heat treatment. This in turn prevents the irreversible loses of fresh plant activities, which can be delivered with maximum potency using, for example, novel tea bag or analogous delivery systems. Instead of conventional paper tea bags, which allow all soluble tea ingredients to move through large pores to the surrounding water, the novel tea bag is made from semi-permeable membrane. This bag contains bioactive composition inside and allows only ingredients having molecular weight below certain membrane cut off (for example, 5,000 Dalton) to penetrate to the surrounding water phase. The ingredients having higher molecular weight remain inside the bag and thus are not included in the beverage.

Therefore, the cut off of ingredients having molecular weight above a certain level allows the production of a beverage having no oxidized ingredients because all oxidized ingredients of bioactive compositions having molecular weight above a certain level remain inside the bag. The novel tea bag design can be based on pyramidal tea bag construction, which utilizes dialysis membrane tube. The design of novel tea bag can also include thin plastic frame having bioactive composition inside and two transparent surfaces built from semi-permeable membrane. The selection of particular membrane cut off value is determined by the type of bioactive composition, but in general higher cut off enabling release into surrounding water phase of a higher percent of composition's dry matter lower amount of the redox potential is preferable.

Example 5

Preparation of Topical Ingredient SF Derived from Cell Juice Serum

Cell juice serum (composition D) cannot be used as an active ingredient of topical products due to the lack of stability and deterioration of color and odor. The described procedure allows for the refinement of cell juice serum fraction to yield a stable and active topical ingredient SF (this procedure is similar to previously described in U.S. Patent Application Publication No. 2003/0175235, which is hereby incorporated by reference in its entirety). The refinement of the cell juice serum involved the following steps: heat treatment, cooling, filtration, and stabilization. Refinement was performed immediately after separation of the cell juice serum from the cytoplasm fraction as described in Example 1. The cell juice serum was exposed to microwave treatment using a temperature probe control. This treatment continued until the temperature of the cell juice serum reached 99° C. (90° C. was required as was previously described in U.S. Patent Application Publication No. 2003/0175235, which is hereby incorporated by reference in its entirety). Once coagulation was induced the treated cell juice serum was immediately cooled to 10° C. The coagulated cell juice serum was vacuum filtrated through filter having porous 0.8 μm (double layers of Whatman No. 2 filters were used in U.S. Patent Application Publication No. 2003/0175235, which is hereby incorporated by reference in its entirety). The precipitate was discarded and the resulting cell juice serum filtrate was used for further processing (i.e., stabilization). Stabilization of the cell juice serum filtrate was achieved by adding preservatives (no exogenous anti-oxidant was required as was previously described in U.S. Patent Application Publication No. 2003/0175235, which is hereby incorporated by reference in its entirety) and incubating the mixture until complete solubilization was achieved. The preservatives used included the following: 0.1% potassium sorbate, 0.1% sodium benzoate, 0.1% sodium methyl paraben, and 0.1% citric acid. This preparation resulted in the production of 16.3 kg of dry matter yield (or approximately 286 Liters) of the topical ingredient SF, which was used for characterization of its physico-chemical and bioactive qualities. The recommended storage conditions for topical ingredient SF include storage in a closed container protected from light at a temperature of between 15° C. and 25° C.

Example 6

Product Specifications of Topical Ingredient SF Derived from Cell Juice Serum Fraction Topical Ingredient SF was prepared according to the process described above in Example 5. Analyses of topical ingredient SF were conducted to determine its various physico-chemical, microbial, cytotoxicity, and bioactivity characteristics, as described below. Topical ingredient SF is a clear liquid, which has a light-yellow-brown color and a light-characteristic odor. No solvent (i.e. glycol, oil, or water) was added to the carrier medium. Table 5 summarizes the Physical and Chemical data of topical ingredient SF.

TABLE 5

Physical and Chemical Parameters of Topical Ingredient SF

| Parameter | Method | Results |
|---|---|---|
| Solid Content, % | See Example 20, "Method 1" | 5.04 |
| Specific Gravity, g/cm$^3$ | USP <841> | 1.015 |
| Color | Gardner Scale | 5-6 |
| Refractive Index | USP <831> | 1.312 |
| PH | USP <791> | 4.0 |
| Redox Potential, mV | See reference [1] | 75 |
| Conductivity, S/m | See reference [2] | 1.02 |

References: [1] Handbook of Chemistry and Physics, 80$^{th}$ Edition, CRC Press, 1999-2000, 5-90; [2] Handbook of Chemistry and Physics, 80$^{th}$ Edition, CRC Press, 1999-2000, 8-21, which are hereby incorporated by reference in their entirety.

Table 6 describes the UV-Spectra data regarding topical ingredient SF.

TABLE 6

UV-Spectra of Topical Ingredient SF (1:500 Dilution)

| Peak | Parameter | Method | Results |
|---|---|---|---|
| #1 | Start, nm | USP <197> | 450 |
|  | Apex, nm | " | 266.5 |
|  | End, nm | " | 247 |
|  | Height, Abs | " | 0.231 |
|  | Area, Abs x nm | " | 13.676 |
| #2 | Start, nm | USP <197> | 247 |
|  | Apex, nm | " | 204 |
|  | End, nm | " | 200 |
|  | Height, Abs | " | 1.396 |
|  | Area, Abs x nm | " | 32.413 |

The microbial analysis conducted in accordance with the following procedure (USP <61>) demonstrated that topical ingredient SF contains less then 100 colony forming units per gram of sample and has no pathogens (E. coli, Candida albicans, Pseudomonas sp. and Staphylococcus aureus). This data demonstrates that topical ingredient SF satisfies the industry requirements for ingredients of topical products.

Topical ingredient SF was determined to be stable (i.e., maintaining physical and chemical integrity) for at least 12-18 months while stored at a temperature of between 15 and 25° C. in a closed container protected from light. Topical ingredient SF is a biodegradable product. In a controlled clinical evaluation, topical ingredient demonstrated the biological activities, which are summarized in Table 7.

TABLE 7

Biological Activities of Topical Ingredient SF

| Activity | Method | µg DM/ml |
|---|---|---|
| Superoxide Scavenging Activity (ICR$_{50}$) | See Example 20, "Method 7" | 69.5 |
| Elastase Inhibitory (IC$_{50}$) | See Example 20, "Method 5" | 32.3 |
| MMP-9 Inhibitory (IC$_{50}$) | See Example 20, "Method 6" | 14.6 |
| Trypsin Inhibitory (IC$_{50}$) | See reference [1] | 7.8 |

Reference: [1] Cannel et al., Planta Medica 54: 10-14 (1988), which is hereby incorporated by reference in its entirety.

Table 7 shown that topical ingredient SF demonstrated superoxide scavenging ability. In a controlled clinical evaluation, topical ingredient SF demonstrated a 50% inhibition of cytochrome c reduction (ICR$_{50}$) at a concentration 69.5 µg dry matter per ml. The ICR$_{50}$ of positive control (rosmarinic acid)=26.5 µg/ml. In addition to anti-oxidant properties, topical ingredient SF demonstrated antiproteolytic activities against peptide hydrolases, for example elastase, gelatinase B or so-called matrix metalloproteinase 9 (MMP-9), and trypsin. Among these enzymes the unique position belongs to elastase and MMP-9, which act synergistically and play an extremely important role in skin inflammation. It should be noted, that both MMP-9 and elastase are secreted by white blood cells (neutrophils) and these enzymes are the key enzymes in the final pathway leading to inflammation. It is generally agreed that if preparation can inhibit both enzymes (elastase and MMP-9), such preparation is considered to be very effective to treat inflammatory processes.

It should be noted that skin aging processes, sunburns, formation of wounds and scars have the very same inflammation mechanism, which involves both MMP-9 and elastase. Thus, topical ingredient SF capable of inhibiting both of the above enzymes has very wide spectrum of applications, among which are inflammatory injury because the following reasons:

a. These two enzymes can synergize to degrade all the components of extracellular matrix of human tissue;
b. Elastase can inactivate the body's own inhibitory defense against MMP-9; and
c. MMP-9 can inactivate the body's own inhibitory defense against elastase.

The combination of anti-inflammatory and anti-oxidant properties of topical ingredient SF suggests that this hydrophilic preparation based on bioactive composition D is capable to act systemically on very fundamental skin disorder problems.

Example 7

Preparation of Topical Ingredient MF Derived from Membrane Fraction

The freshly obtained membrane fraction is a paste having intensive color and specific odor. This fraction is represented predominantly by chloroplasts and its composition includes predominantly phospholipids, membrane proteins, chlorophyll, and carotenoids. The drying of membrane fraction results in irreversible loses of many valuable properties required for the exploration of membrane fraction as a topical ingredient. Without drying, the unstable membrane fraction is quickly transformed into the dark color un-dispersible and insoluble conglomerates having a strong and non-characteristic odor. As result, such material cannot be used as a topical ingredient. The procedure described below allows for transformation of freshly obtained membrane fractions into stable and active topical ingredients (this procedure is similar to previously described in the U.S. Patent Application Publication No. 2003/0175235, which is hereby incorporated by reference in its entirety).

Immediately after separation of the membrane fraction from cell juice according to the process described above in Example 1, the membrane fraction was stabilized and incorporated into a polymer matrix. To prepare approximately 100 grams of topical ingredient MF the cell membrane fraction was stabilized by mixing it with non-ionic emulsifier Polysorbate 80 (Tween 80) and antioxidants (Tenox 4). Specifically, 20 grams of fresh membrane fraction was mixed vigorously with 3.5 grams of Tween 80 and 0.1 gram of Tenox 4 (solution of Butylated Hydroxyanisole and Butylated Hydroxytoluene in oil) until homogeneous, while avoiding aeration during mixing.

Once stabilized, the membrane fraction was incorporated into a polymer matrix (i.e., a dispersion of polymeric emulsifier, acrylates/C10-C30 acrylate crosspolymer). The polymer matrix was prepared by dispersing 0.9 grams of Pemulen TR-2 in 69.2 grams of warm deionized water and mixing until uniform using moderate agitation, while avoiding aeration. In parallel, 5 grams of Glycerin and 1.0 gram of Phenonip (mixture of Phenoxyethanol (and) Methylparaben (and) Butylparaben (and) Ethylparaben (and) Propylparaben) were combined in a separate vessel and mixed until uniform. With moderate agitation, the phases containing Pemulen and Glycerin with Phenonip were combined and mixed until uniform. To incorporate the membrane fraction into the polymer matrix, the phase containing the membrane fraction, Tween 80, and Tenox 4 was added to the phase containing the Pemulen, Glycerin, and Phenonip, and then mixed with vigorous agitation while avoiding aeration. Stabilization of the membrane fraction mixture was achieved by neutralizing it with 18% aqueous solution of sodium hydroxide (NaOH) and mixed vigorously to produce a uniform system having a pH of 5.0±0.4. This preparation, which started from 100 kg of fresh *Camellia* biomass (approximately 461 kg of fresh leaves having 21.7% dry matter), resulted in the production of 11.85 kg of Dry Matter yield (or approximately 172 liters) of topical ingredient MF, which was used for characterization of its physico-chemical and bioactive qualities. The recommended storage conditions for topical ingredient MF include storage in a closed container protected from light at a temperature between 2 and 8° C.

Example 8

Product Specifications of Topical Ingredient MF Derived from Membrane Fraction

Topical ingredient MF was prepared according to the process described above in Example 7. Analyses of topical ingredient MF were conducted to determine its various physico-chemical, microbial, cytotoxicity, and bioactivity characteristics, as described below. Topical ingredient MF is an opaque gel, which has a green-brown color and light-characteristic odor. Topical ingredient MF was formulated utilizing the natural cell juice constituents gelled with a polymer to assure the highest level of purity uniformity, compatibility, stability, safety and efficacy.

Table 8 describes the physical and chemical data of topical ingredient MF.

TABLE 8

Physical and Chemical Parameters of Topical Ingredient MF

| Parameter | Method | Results |
|---|---|---|
| Non-Volatile Residue (NVR), % | See Example 20, "Method 2" | 6.9 |
| Specific Gravity, g/cm$^3$ | USP <841> | 1.035 |
| Viscosity, cps | USP<911> | 18,700 |
| pH | USP <791> | 4.6 |
| Total Carotenoids, % NVR | See Example 20, "Method 4" | 0.36 |
| Lutein, % NVR | See Example 20, "Method 4" | 0.34 |

Table 9 summarizes the L*a*b* values data regarding topical ingredient MF.

TABLE 9

L*a*b* Values of Topical Ingredient MF

| Parameter | Method | Results |
|---|---|---|
| L* | See Example 20, "Method 3" | 30.27 |
| a* | " | 27.36 |
| b* | " | 42.56 |

Microbial analyses demonstrated that topical ingredient MF satisfies the industry requirements for topical ingredients with regard to CFUs and absence of pathogens (USP <61>).

Topical ingredient MF was determined to be stable (i.e., maintaining physical and chemical integrity) for at least 12-18 months while stored at a temperature of between 2 and 8° C. in a closed container protected from light. Topical ingredient MF is a biodegradable product. In a controlled clinical evaluation, topical ingredient MF demonstrates elastase inhibitory activity and trypsin inhibitory activity. Table 10 summarizes certain bioactivity results for topical ingredient MF.

TABLE 10

Bioactivity Results of Topical Ingredient MF

| Activity | Method | IC$_{50}$ (µg/ml) |
|---|---|---|
| Elastase Inhibitory (IC$_{50}$) | See Example 20, "Method 5" | 12.3 |
| MMP-9 Inhibitory (IC$_{50}$) | See Example 20, "Method 6" | 5.6 |
| Trypsin Inhibitory (IC$_{50}$) | See reference [1] | 3.8 |

Reference: [1] Cannel et al., *Planta Medica* 54: 10-14 (1988), which is hereby incorporated by reference in its entirety.

Table 10 shown that topical ingredient MF demonstrated properties similar to topical ingredient SF (see Example 6). Although topical ingredient MF has no superoxide scavenging activity, it demonstrates higher specific enzyme inhibition activities than topical ingredient SF. Thus topical ingredient MF, which is based on bioactive composition B, should be considered as a potent multiphase anti-inflammatory ingredient having broad applications for treatment of skin disorders.

Example 9

Spectral Analyses of the Bioactive Compositions Derived from *Camellia sinensis* Plants Introduction to Spectral Analyses. Ultraviolet (UV) radiation has damaging effects on human skin. Short-term effects include tanning and sunburn, while the long-term effects of cumulative UV exposure include photoaging of the skin and increased risk of skin cancer. Ultraviolet skin injury is mediated by oxidative damage, and a number of plant extracts with antioxidant activity are showing promise as protective agents: grape seed extract (Carini et al., "Protective Effect of Procyanidines from *Vitis vinifera* Seeds on UV-Induced Photodamage: In vitro and In vivo Studies," *Proceedings of the 19th IFSCC Congress* 3:55-63 (1996), which is hereby incorporated by reference in its entirety), lycopene (Di Mascio et al., "Lycopene as the Most Efficient Biological Carotenoid Singlet Oxygen Quencher," *Archives of Biochemistry and Biophysics* 274:532-8 (1989); and Ribaya-Mercado et al., "Skin Lycopene is Destroyed Preferentially Over β-Carotene During Ultraviolet Irradiation in Humans," *Journal of Nutrition* 125:1854-9 (1995), which are hereby incorporated by reference in their entirety), silymarin (Morazzoni et al., "*Silybum marianum* (*Carduus marianus*)," *Fitoterapia* 66:3-42 (1995); Katiyar et al., "Protective Effects of Silymarin Against Photocarcinogenesis in a Mouse Skin Model," *Journal of the National Cancer Institute* 89:556-66 (1997), which are hereby incorporated by reference in their entirety), and especially green tea extract which has higher efficacy compared with extracts produced from other plant sources (Katiyar et al., "Protection Against Ultraviolet-B Radiation-Induced Local and Systemic Suppression of Contact Hypersensitivity and Edema Responses in C3H/HeN Mice by Green Tea Polyphenols," *Photochemistry and Photobiology* 62:855-61 (1995); Ruch et al., "Prevention of Cytotoxicity and Inhibition of Intercellular Communication by Antioxidant Catechins Isolated from Chinese Green Tea," *Carcinogenesis* 10:1003-8 (1989); Wang et al., "Protection Against Ultraviolet B Radiation-Induced Photocarcinogenesis in Hairless Mice by Green Tea Polyphenols," *Carcinogenesis* 12:1527-30 (1991), which is hereby incorporated by reference in its entirety).

It was found that the leaves of the tea plant (*Camellia sinensis*) have a high content of polyphenols with antioxidant activity including (−)-epicatechin, (−)-epicatechin-3-gallate, (−)-epigallocatechin, and (−) epigallocatechin-3-gallate. Green tea extract has shown an antioxidant activity against hydrogen peroxide and the superoxide radicals and prevention of oxidative cytotoxicity. The extract can also prevent the inhibition of intercellular communication, a possible mechanism of tumor promotion. There is a close association between UV-induced immune suppression and the development of skin cancer, and green tea extract has been found to protect against inflammation and immune suppression caused by UV-B radiation. Green tea extract given orally in drinking water or applied topically protects against UV-B-induced skin carcinogenesis in animal models. These results indicate that green tea extract taken orally may help to prevent skin cancer.

Although the UV protection properties of *Camellia* products have been established, the greater potential of tea plant as a source for effective protection of the skin against sun damage has not fully explored due to the limitations of conventional technology, which is driven towards focusing on a limited to relatively narrow band of active ingredients: predominately cathechins Comparative UV protection properties studies described herein between "novel" and "conventional" *Camellia* products have now demonstrated that the technology of "fresh *Camellia* fractionation" is capable of yielding more potent products. The comparison was made by utilizing the methods commonly used to determine spectral properties of solutions and in-vitro sun protection factor (SPF).

Methodology A: UV/VIS Spectra. UV/VIS spectra of *Camellia* products in 200-450 nm region were obtained using pharmacopoeia compliant Spectrophotometer Ultrospec 4300 Pro (Amersham Biosciences Ltd., Buckinghamshire, England). The spectral parameters of diluted in distilled water *Camellia* products were determined according to the procedure described in USP <197>.

Methodology B: Absorbance Spectra. Absorbance spectra of *Camellia* products in 250-450 nm region were obtained using UV-1000S Transmittance Analyzer (Labsphere, Inc., North Sutton, N.H.) and Vitro-Skin® testing substrate (IMS Testing Group, Milford, Conn.), which mimics the surface properties of human skin. It contains both optimized protein and lipid components and is designed to have topography, pH, critical surface tension and ionic strength similar to human skin.

The *Camellia* samples were uniformly spread on a surface of pre-hydrated substrate (application dose=2.0 μl/sq. cm). After 15 min after application the initial absorbance spectra were taken via five (5) replications. Then the substrates with applied products were irradiated by broad-spectrum solar light simulator (Model 16S-300 Single Port, Solar Light Company, Inc., Philadelphia, Pa.) equipped with 300-Watt xenon lamp. The dose control system PMA 2100-DCS allowed precision control of the dose delivered to a sample.

Immediately after irradiation (irradiation dose=60 Joules/sq. cm) absorbance spectra from the same spot were taken in (5) five replications. The absorbance spectra of samples before and after irradiation were used for statistical analysis.

Samples. The following bioactive compositions, which were prepared according to the process described above in Example 1 were evaluated: composition A (cell walls fraction extract having 0.84% dry matter), composition B (membrane fraction extract having 6.83% dry matter), composition D (cell juice serum having 5.69% dry matter). Extract of conventional white tea having 1.10% dry matter and extract of conventional black tea having 1.38% dry matter were used as controls. All samples were obtained from the same batch of fresh *Camellia*, which was collected at Charleston Tea Plantation, SC. These samples did not contain any additives.

Figure 2:
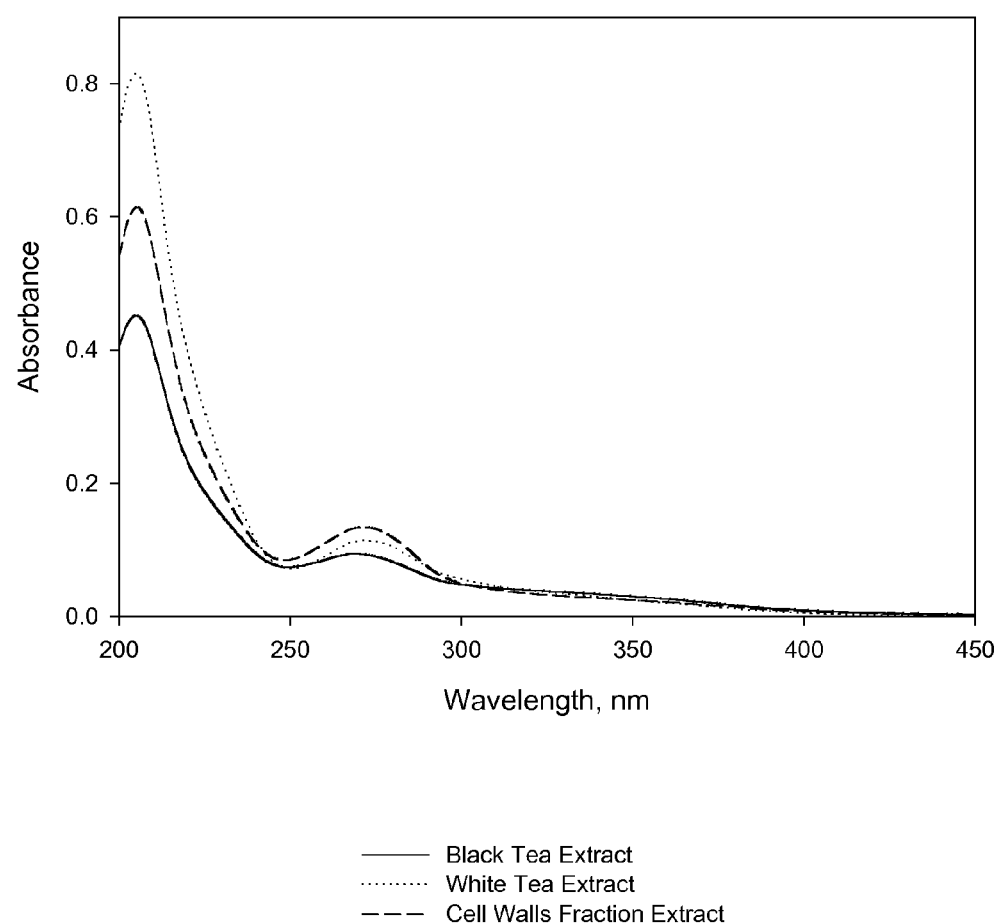
FIG. 2 is a graph showing the UV/VIS spectra of extracts of cell walls fraction and conventional teas (Dilution 1:1000).
Figure 3:
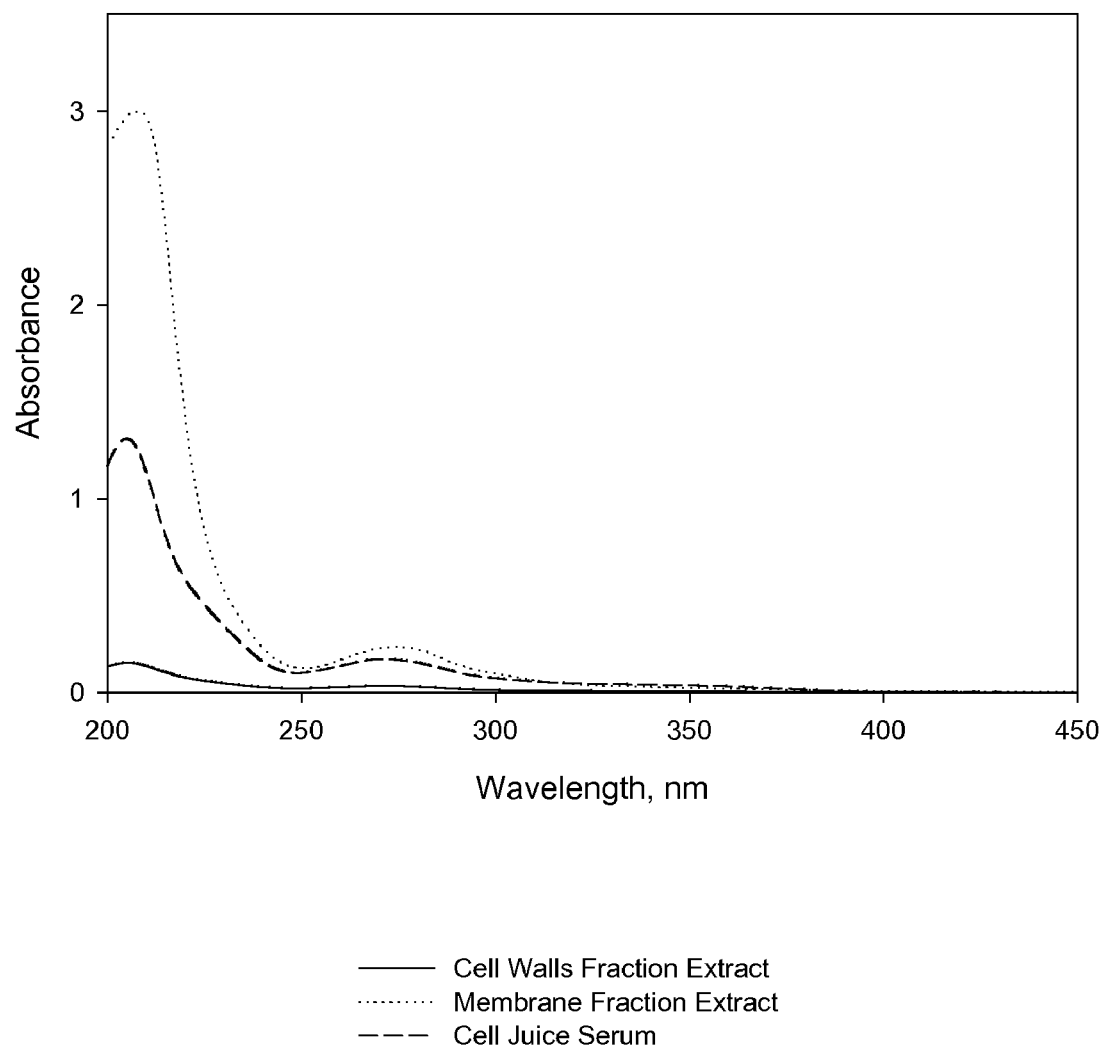
FIG. 3 is a graph showing the UV/VIS spectra of *Camellia* bioactive compositions (Dilution 1:4000).

Analyses. It was found that all *Camellia* samples have high UV absorbance values and thus they were diluted with distilled water. The UV-VIS spectra of diluted *Camellia* products are presented on FIGS. 2 and 3.

The spectra of all liquid samples have certain similarities. For example, positions of peaks are varied in relatively narrow ranges of $\lambda_{max1}$=269-274 nm and $\lambda_{max2}$=205-208 nm, which indicate the presence of aromatic rings and conjugated systems of σ–π bonds in all tested samples. However, the apex value of peaks, area under each peak and total area under integral spectral curves are different (Table 11), which suggest that tested samples have different compositions of optically active constituents.

TABLE 11

Parameters of UV/VIS Spectra of Camellia Products

| | Peak # 1 | | | | | Peak # 2 | | | | | Area under the Spectra Curve*, Abs · nm |
|---|---|---|---|---|---|---|---|---|---|---|---|
| | Start, nm | $\lambda_{max1}$, nm | End, nm | Height, Abs | Area % | Start, nm | $\lambda_{max2}$, nm | End, nm | Height, Abs | Area % | |
| White Tea Extract | 450 | 269 | 250 | 0.114 | 28.1 | 250 | 205 | 200 | 0.816 | 71.9 | 6.604 |
| Black Tea Extract | 450 | 272 | 250 | 0.094 | 37.3 | 250 | 205 | 200 | 0.452 | 62.7 | 4.616 |
| Cell Walls Fraction Extract | 450 | 272 | 248 | 0.134 | 35.8 | 248 | 205 | 200 | 0.614 | 64.2 | 5.727 |
| Membrane Fraction Extract | 450 | 274 | 251 | 0.944 | 16.2 | 251 | 208 | 200 | 11.98 | 83.8 | 80.133 |
| Cell Juice Serum | 450 | 271 | 249 | 0.692 | 26.3 | 249 | 205 | 200 | 5.228 | 73.7 | 39.599 |

*The Area under Spectra values were normalized based on dilution of the samples.

The comparison of areas under integral spectral curves obtained from 200 nm to 450 nm clearly demonstrates that membrane fraction extract (composition B) and cell juice serum (composition D) had the higher absorption values (Table 11). The ratio "Area under Spectra:Dry Matter" indicates that specific absorption value of the samples is increasing in the following sequence: black tea extract>white tea extract>cell walls fraction extract>cell juice serum>membrane fraction extract (Table 12).

429-40 (1990), which is hereby incorporated by reference in its entirety). Although absorption of tested liquid samples in the area 290-400 nm contributes only ~10% of total UV/VIS absorption, novel Camellia compositions have higher absorption in the above spectral area as well.

Thus the data related to the diluted solutions of Camellia samples provided initial estimation of UV protection potency of tested products, which was further evaluated using the Vitro-Skin® testing substrate (IMS Testing Group, Milford,

TABLE 12

Selected Spectral Characteristics of Camellia Products

| | Dry Matter % | Area under Spectra, Abs · nm | Ratio: Area under Spectra$^{(200-450\,nm)}$ / Dry Matter | Area under Spectra$^{(290-400\,nm)}$ Abs · nm | Ratio: Area under Spectra$^{(290-400\,nm)}$ / Dry Matter |
|---|---|---|---|---|---|
| White Tea Extract | 1.10 | 6.604 | 6.004 | 0.812 | 0.738 |
| Black Tea Extract | 1.38 | 4.616 | 3.345 | 0.854 | 0.619 |
| Cell Walls Fraction Extract | 0.84 | 5.727 | 6.818 | 0.776 | 0.924 |
| Membrane Fraction Extract | 6.83 | 80.133 | 11.733 | 4.304 | 0.630 |
| Cell Juice Serum | 5.69 | 39.599 | 6.959 | 4.320 | 0.759 |

Figure 4:
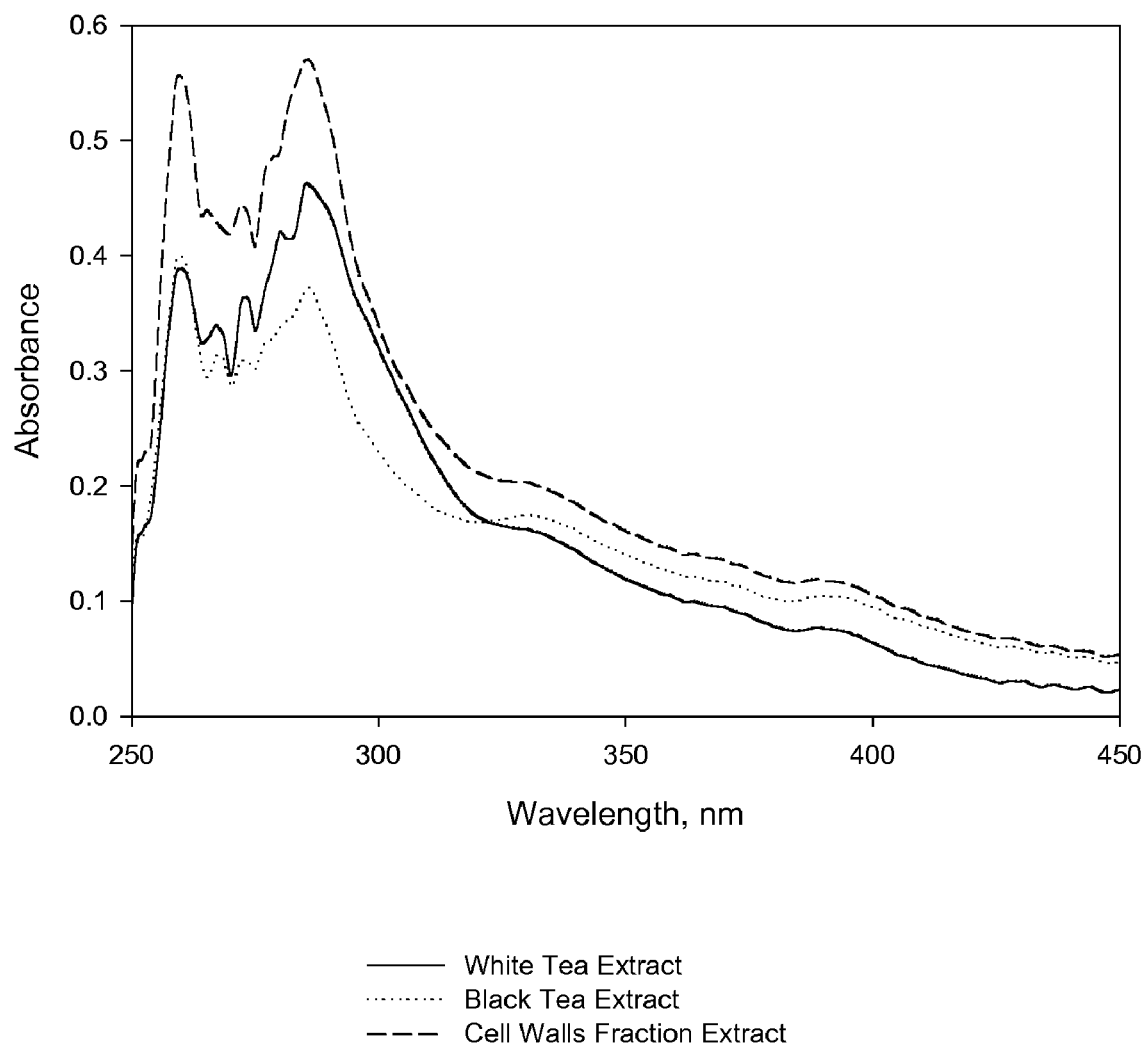
FIG. 4 is a graph showing the absorbance spectra of extracts of cell walls fraction and conventional teas applied on Vitro-Skin® testing substrate (IMS Testing Group, Milford, Conn.). Dry matter levels are equalized.
Figure 5:
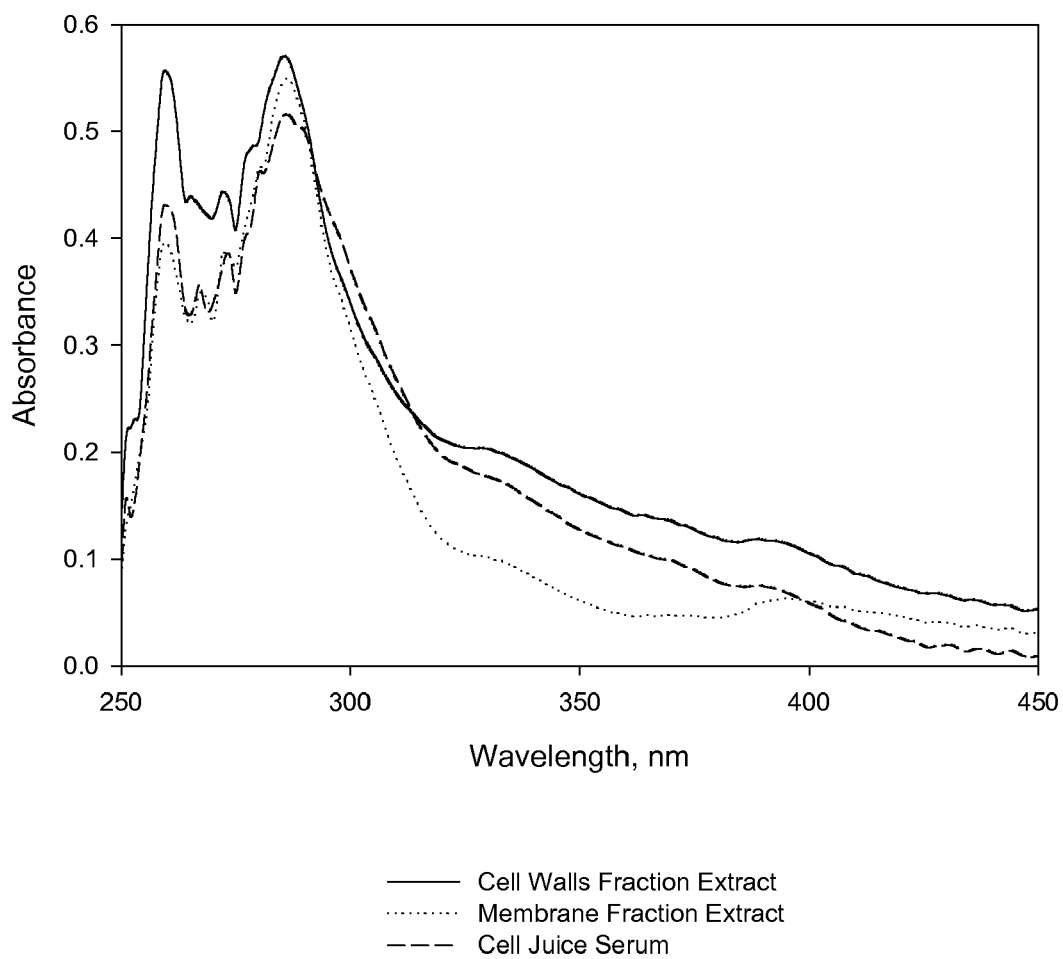
FIG. 5 is a graph showing the absorbance spectra of *Camellia* bioactive compositions applied on Vitro-Skin® testing substrate (IMS Testing Group, Milford, Conn.). Dry matter levels are equalized.
Figure 6:
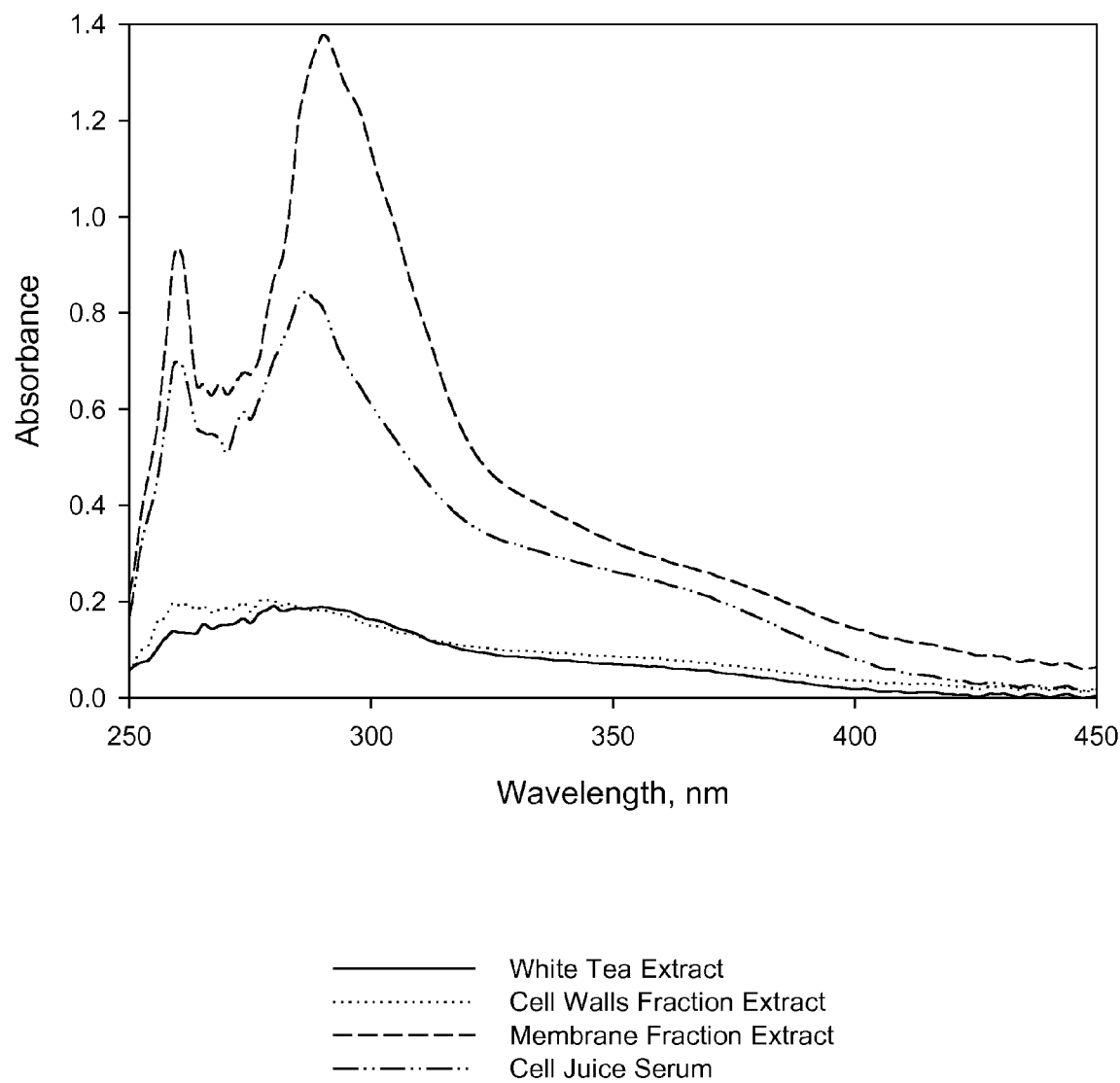
FIG. 6 is a graph showing the absorbance spectra of *Camellia* bioactive compositions and white tea extract applied on Vitro-Skin® testing substrate (IMS Testing Group, Milford, Conn.).

Based on the comparison of absorption values, novel bioactive compositions appear to be more effective protectors of the skin against sun damage than extracts of conventional white tea and black tea. It should be pointed out, that UV protection properties of Camellia products should be better estimated using absorption data related to the area from 290 nm to 400 nm because this particular part of spectra is responsible for UV induced damage of the skin (Sayre et al., "A Method for the Determination of UVA Protection for Normal Skin," Journal of American Academy of Dermatology 23:

Conn.). The results are presented in FIGS. 4-13. It was found that novel Camellia compositions and extracts of conventional white tea and black tea have different spectral characteristics even after they were applied on substrate in concentrations, which were equalized with respect to dry matter level (FIGS. 4 and 5).

The spectral of Camellia samples, which were applied on Vitro-Skin® testing substrate (IMS Testing Group, Milford, Conn.) included from four to two characteristics peaks, which have different apex values (Table 13).

TABLE 13

Parameters of Absorbance Spectra of Camellia Products Applied on Vitro-Skin ® Testing Substrate

| | Peak # 1 | | Peak # 2 | | Peak # 3 | | Peak # 4 | |
|---|---|---|---|---|---|---|---|---|
| | $\lambda_{max4}$ | Height, Abs | $\lambda_{max3}$ | Height, Abs | $\lambda_{max2}$ | Height, Abs | $\lambda_{max1}$ | Height, Abs |
| White Tea Extract | 260 | 0.389 | 286 | 0.461 | 330 | 0.163 | 392 | 0.076 |
| Black Tea Extract | 260 | 0.399 | 286 | 0.373 | 330 | 0.175 | 390 | 0.105 |

TABLE 13-continued

Parameters of Absorbance Spectra of *Camellia* Products Applied on Vitro-Skin ® Testing Substrate

| | Peak #1 | | Peak #2 | | Peak #3 | | Peak #4 | |
|---|---|---|---|---|---|---|---|---|
| | $\lambda_{max4}$ | Height, Abs | $\lambda_{max3}$ | Height, Abs | $\lambda_{max2}$ | Height, Abs | $\lambda_{max1}$ | Height, Abs |
| Cell Wall Fraction Extract | 260 | 0.555 | 286 | 0.569 | 330 | 0.203 | 389 | 0.118 |
| Membrane Fraction Extract | 260 | 0.394 | 286 | 0.549 | — | — | 394 | 0.059 |
| Cell Juice Serum | 260 | 0.431 | 286 | 0.517 | — | — | — | — |

It should be pointed out, that parameters of characteristic peaks of *Camellia* products in solutions (Table 11) were very different compared with characteristic of *Camellia* products, which were applied on Vitro-Skin® testing substrate (IMS Testing Group, Milford, Conn.) (Table 13). As control experiments show, the lower pH level (~5.5) on Vitro-Sin® surface can not be responsible for the above differences, which probably are the results of chemical interactions between *Camellia* products and ingredients used for preparation of Vitro-Skin® testing substrate (IMS Testing Group, Milford, Conn.) substrate. Thus, Vitro-Skin® testing substrate (IMS Testing Group, Milford, Conn.) contains both protein and lipid components which could chemically interact with *Camellia* phenolic constituents. It should be noted, that the shifts in spectral properties of tested products were observed for all bioactive compositions as well as for extracts of conventional teas.

Spectra of novel *Camellia* compositions and extracts of conventional *Camellia* products "as is" were also compared, taking into account the different dry matter contents of tested samples. The absorbance spectra of *Camellia* products applied on Vitro-Skin® testing substrate (IMS Testing Group, Milford, Conn.) in equal volumes are presented on FIG. 6.

Although there are some similarities between spectra of cell walls fraction extract and white tea extract, the first product has higher absorbance in the area 250-280 nm and in near UV area. It should be noted that higher absorbance does not correspond with dry matter level, which is higher in white tea extract (1.10%) compared with cell walls fraction extract (0.84%). It suggests that the compositions of these two samples are not identical and that cell walls fraction extract also has lower conductivity consisting of greater non-dissociated optically active ingredients responsible for high absorbance (see data presented in Table 3).

Additionally it was found that the spectra of membrane fraction extract (composition B) and cell juice serum (composition D) are different from spectra of cell walls fraction extract (composition A) and white tea extract. Thus, membrane fraction extract and cell juice serum spectra again indicate that these products have different composition than white tea extract and cell walls fraction extract. At the same time, the spectral data suggest that the compositions of membrane fraction extract and cell juice serum are not identical. For example, membrane fraction extract has three characteristic peaks at 260 nm, 286 nm and 394 nm. The cell juice serum spectra contain two peaks at 260 nm and 286 nm.

Comparison of these two spectra indicates that membrane fraction extract has approximately two times higher extinction then cell juice serum, although difference in dry matter levels is only ~1%. Thus, four tested *Camellia* products have significantly different compositions of constituents, which are optically active in the region 250-450 nm.

The data related to the quantitative comparison of *Camellia* products are presented in Table 14.

TABLE 14

Selected Characteristics of *Camellia* Products Applied of Vitro-Skin ® Testing Substrate

| | Area under Spectra$^{(250-450\ nm)}$ Abs · nm | Area under Spectra$^{(290-400\ nm)}$ Abs · nm | Area under Spectra$^{(290-400\ nm)}$/Area under Spectra$^{(250-450\ nm)}$ % |
|---|---|---|---|
| White Tea Extract | 15.577 | 9.312 | 59.78 |
| Cell Walls Fraction Extract | 18.571 | 10.422 | 56.12 |
| Membrane Fraction Extract | 89.148 | 53.803 | 60.35 |
| Cell Juice Serum | 60.861 | 35.161 | 57.77 |

Table 14 shows that absorption of the samples in the area 250-450 nm and in the area 290-400 nm is increasing in the following order: white tea extract>cell walls fraction extract>cell juice serum>membrane fraction extract. This sequence is completely in agreement with the sequence of specific absorption values of *Camellia* products tested in the diluted solutions (Table 12). The contribution of the absorbance in the 250-400 nm region to the absorbance of the spectra taken from 250 nm to 450 nm reached ~55-60% when tested samples were applied on Vitro-Skin® testing substrate (IMS Testing Group, Milford, Conn.).

Figure 7A:
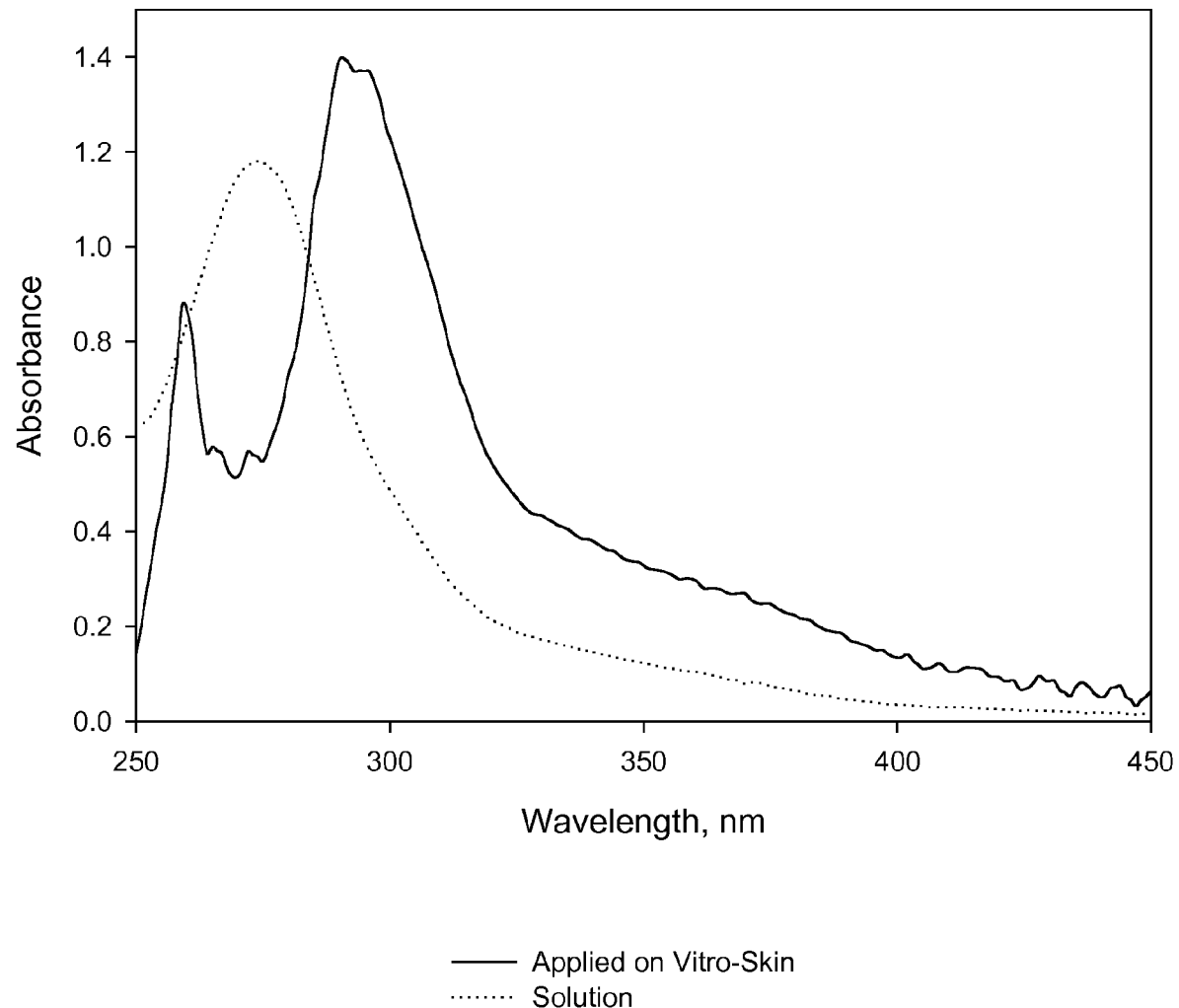
FIG. 7A is a graph showing the absorbance spectra of *Camellia* membrane fraction extract in diluted solution (1:200) and applied on Vitro-Skin® testing substrate (IMS Testing Group, Milford, Conn.).

It should be noted that the spectra of novel *Camellia* compositions in diluted solutions and after their application on Vitro-Skin® testing substrate (IMS Testing Group, Milford, Conn.) substrate are remarkably different. These differences are both quantitative and qualitative for membrane fraction extract and cell juice serum. Thus in the range from 250 nm to 450 nm membrane fraction extract in solution peaks at 274 nm. The same membrane fraction extract when applied on Vitro-Skin® testing substrate (IMS Testing Group, Milford, Conn.), did not show any characteristic peak at the above wavelength, but instead had two characteristic peaks at 260 nm and 286 nm (FIG. 7A).

Figure 7B:
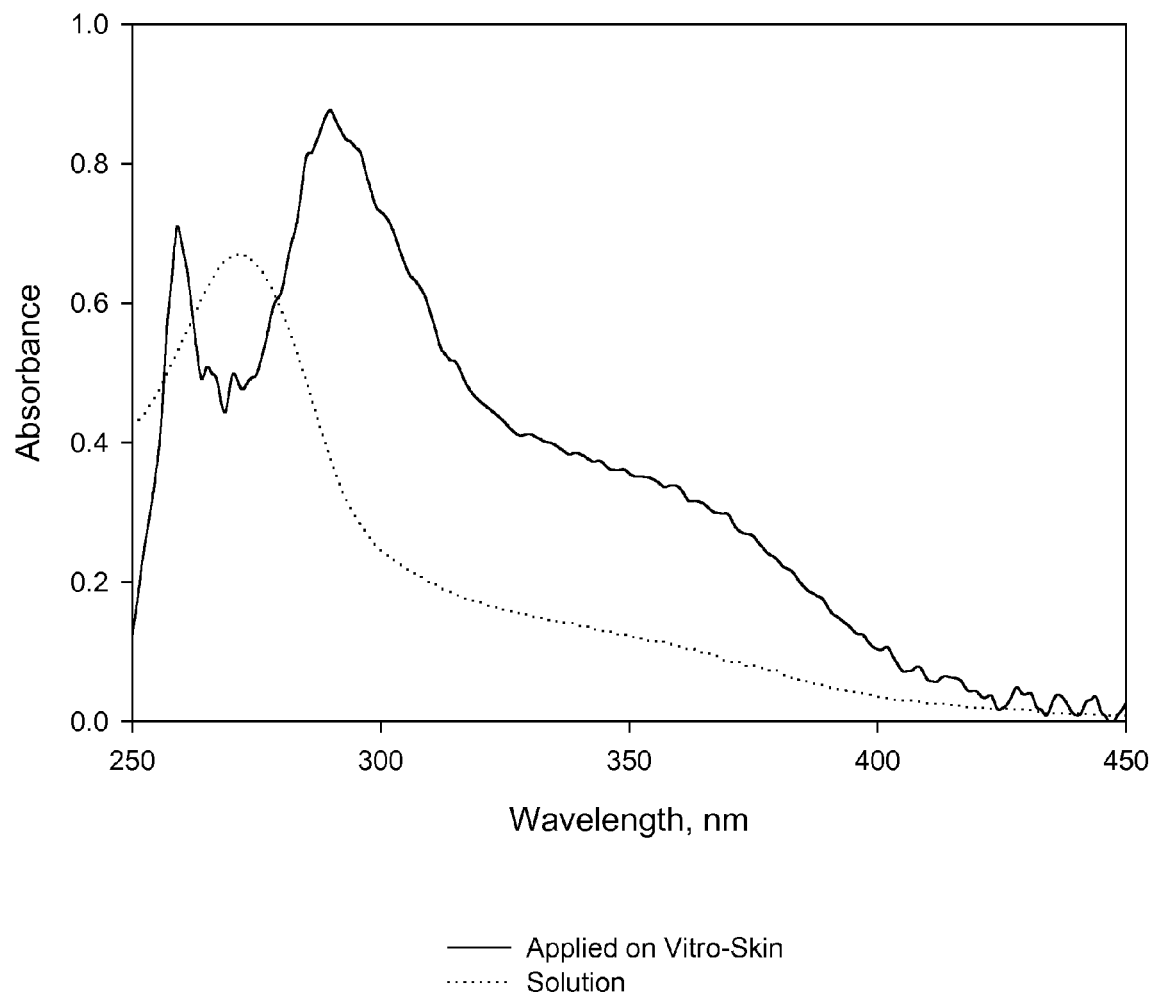
FIG. 7B is a graph showing the absorbance spectra of *Camellia* cell juice serum in diluted solution (1:200) and applied on Vitro-Skin® testing substrate (IMS Testing Group, Milford, Conn.).
Figure 8A:
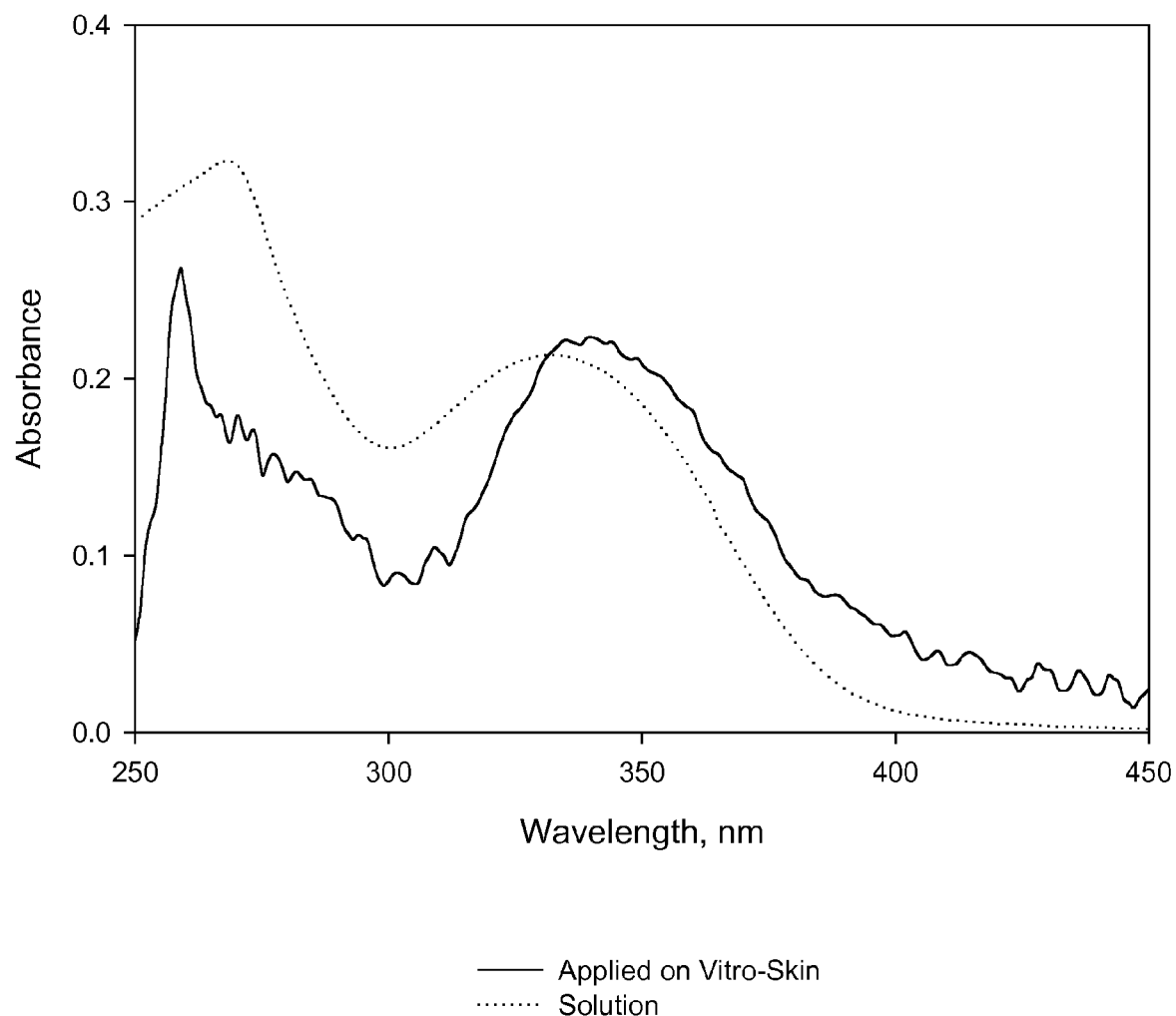
FIG. 8A is a graph showing the absorbance spectra of Barley (*Hordeum vulgare*) cell juice serum in diluted solution (1:200) and applied on Vitro-Skin® testing substrate (IMS Testing Group, Milford, Conn.).
Figure 8B:
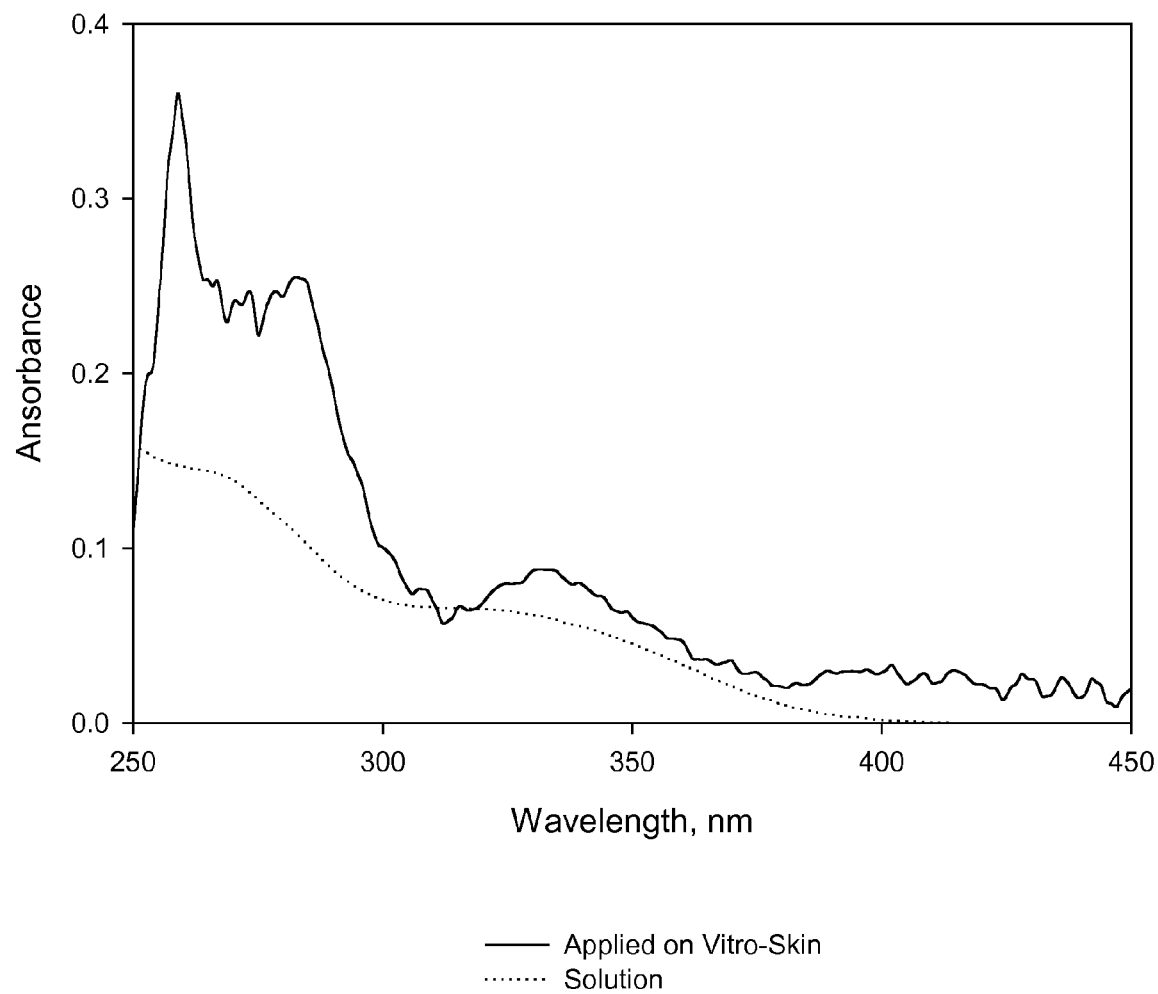
FIG. 8B is a graph showing the absorbance spectra of Sage (*Salvia officinalis*) cell juice serum in diluted solution (1:200) and applied on Vitro-Skin® testing substrate (IMS Testing Group, Milford, Conn.).

The similar pattern in spectral properties was observed for cell juice serum, although additional absorption at ~360 nm was identified in the sample applied on Vitro-Skin® testing substrate (IMS Testing Group, Milford, Conn.), but such phenomena was not registered in UV/VIS spectra of the same composition in the solution (FIG. 7B).

It should be pointed out that above differences between spectra may be the results of chemical interaction between novel Camellia compositions and surface of Vitro-Skin® testing substrate (IMS Testing Group, Milford, Conn.) having protein and lipid components, which mimic human skin. These interactions led to the drastic increase of the absorbance in the spectral region responsible for damaging effect of UV irradiation, i.e., novel Camellia compositions have significant UV protection potencies. Control experiments with Barley (Hordeum vulgare) (FIG. 8A) and Sage (Salvia officinalis) (FIG. 8B) cell juice serums shown that the differences in the spectra of the same samples in solution and after their application on Vitro-Skin® testing substrate (IMS Testing Group, Milford, Conn.) were not observed for plant sources other than Camellia. Thus, the spectral shift in Camellia products after application on Vitro-Skin® testing substrate (IMS Testing Group, Milford, Conn.) indicates the specific interactions having place only between novel Camellia products and substrate which mimics human skin.

Figure 9:
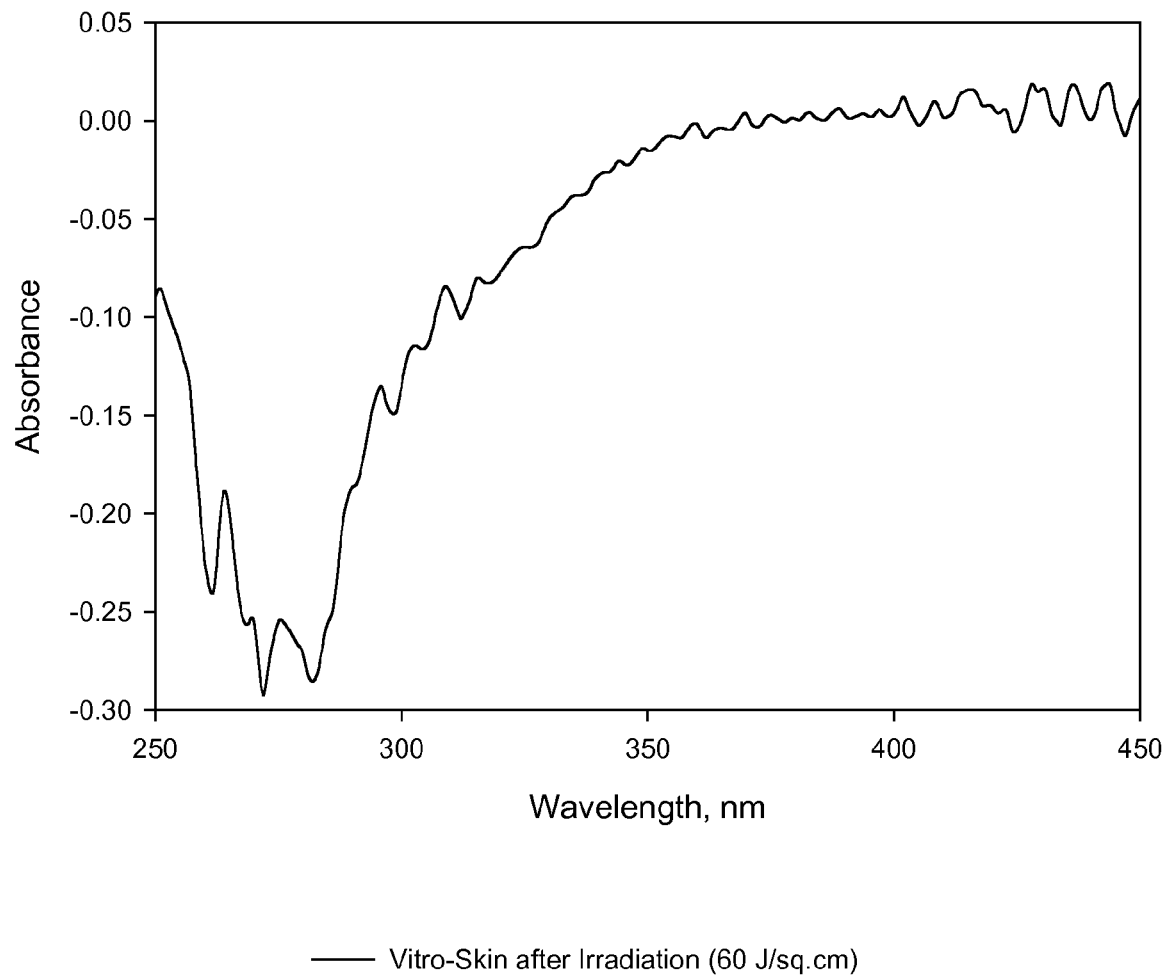
FIG. 9 is a graph showing the effect of broad spectrum UV irradiation on Vitro-Skin® testing substrate (IMS Testing Group, Milford, Conn.).
Figure 10:
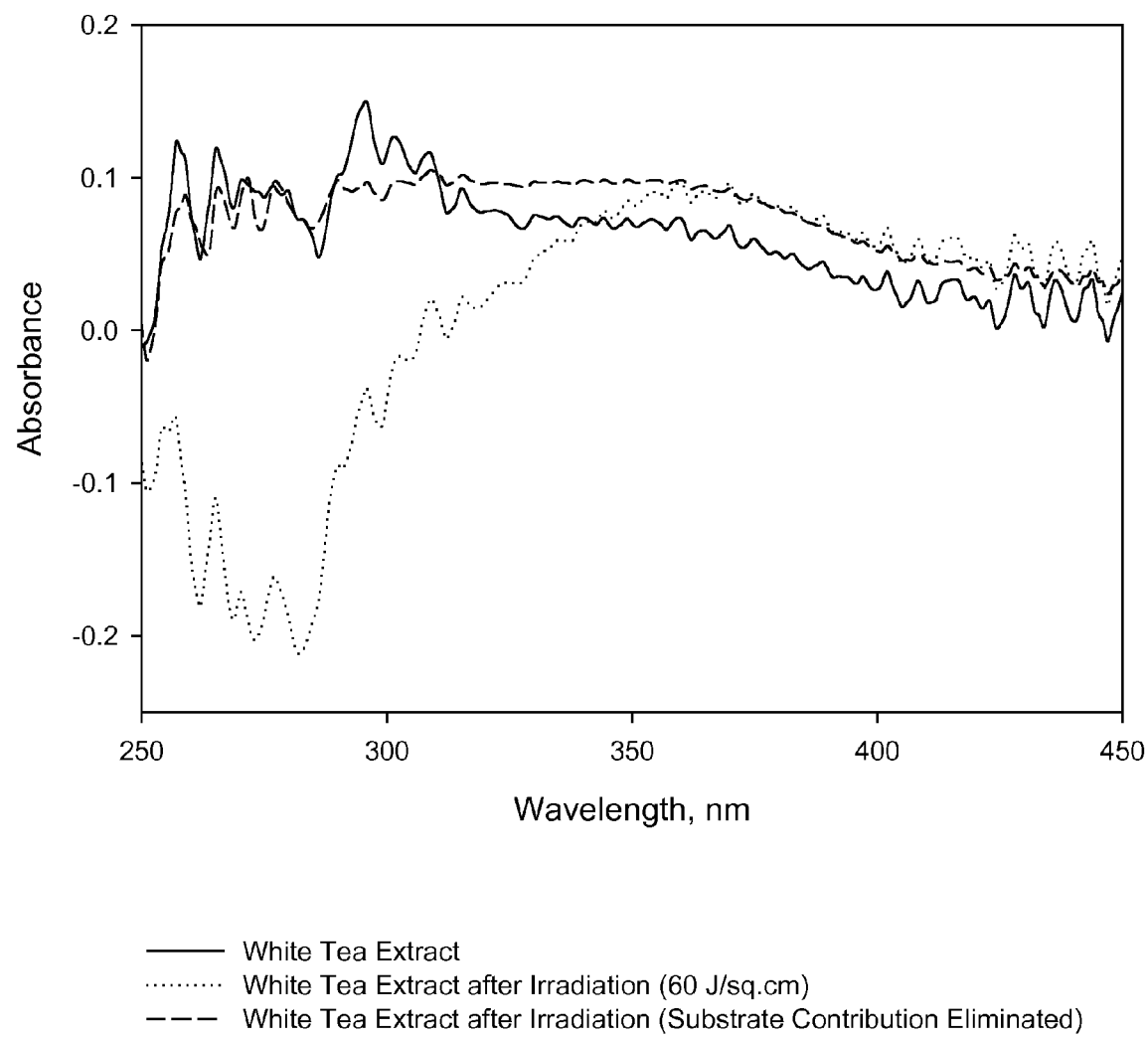
FIG. 10 is a graph showing the effect of broad spectrum UV irradiation on white tea extract applied on Vitro-Skin® testing substrate (IMS Testing Group, Milford, Conn.).
Figure 11:
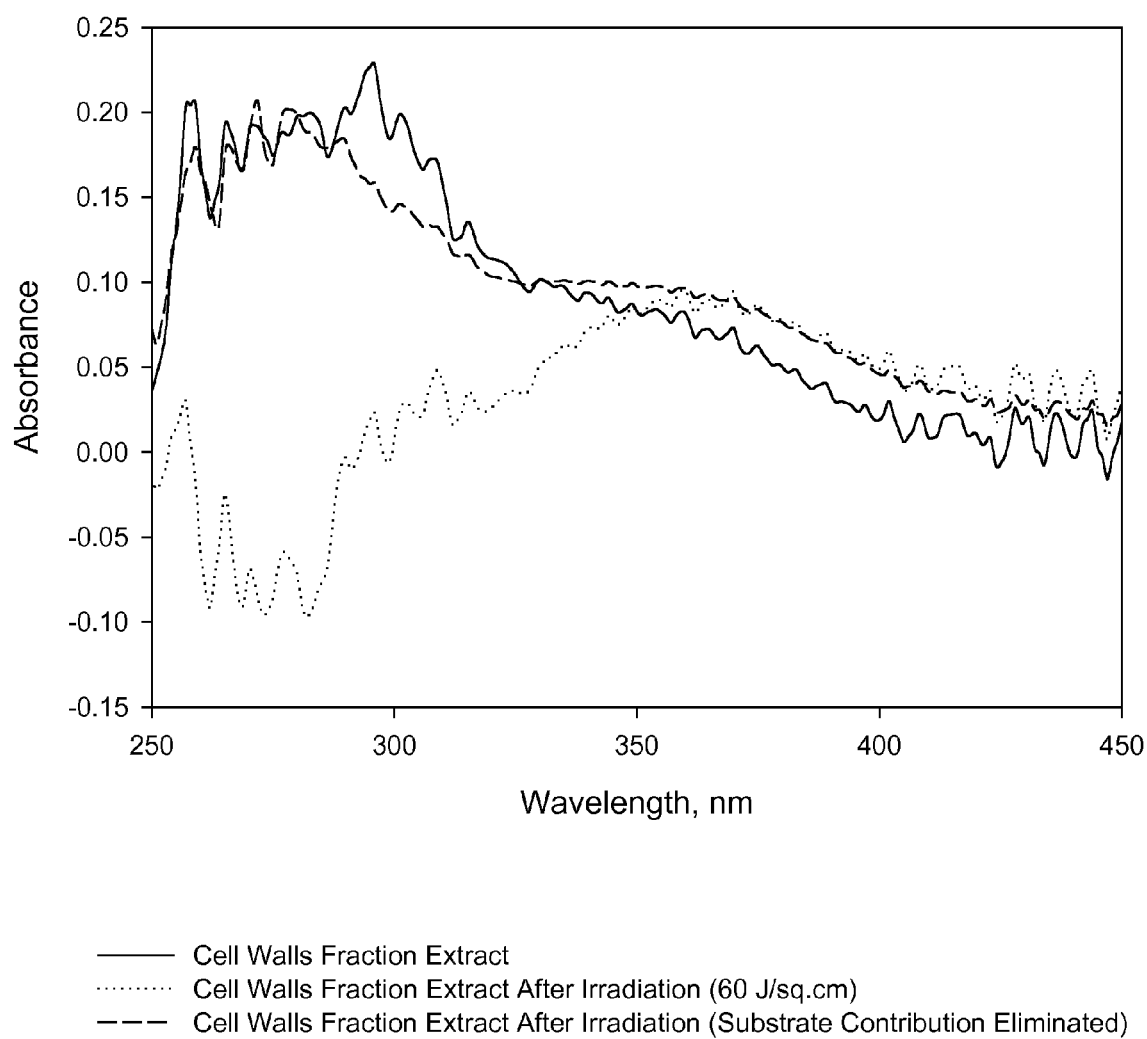
FIG. 11 is a graph showing the effect of broad spectrum UV irradiation on cell walls fraction extract applied on Vitro-Skin® testing substrate (IMS Testing Group, Milford, Conn.).

Control experiments with pre-hydrated substrate demonstrated that after irradiation the absorbance of Vitro-Skin® testing substrate (IMS Testing Group, Milford, Conn.) was significantly decreased especially in the range 260-330 nm (FIG. 9). This effect reflects relatively low photo-stability of non-protected substrate, which was irradiated by high dose of broad-spectrum solar light.

Irradiation of the substrate with applied white tea extract initiated changes in absorbance spectra (FIG. 10) which is analogous with the spectral changes of non-protected Vitro-Skin® testing substrate (IMS Testing Group, Milford, Conn.). When contribution of substrate was eliminated, the spectra of non-irradiated and irradiated sample indicated some similarities but did not demonstrate totally identical behavior. For example, the absorbance in the range 290-310 nm was decreased and wide peak at 360 nm started to form.

The irradiation of cell walls fraction extract (FIG. 11) led to similar changes in the absorbance spectra especially with respect to the curve obtained after elimination (subtraction) of substrate contribution.

Although compositions of white tea extract and cell walls fraction extract are not identical, the pattern of irradiation-induced modifications in their spectra is quite similar. It should be noted that both white tea extract and cell walls fraction extract are not capable of fully protecting the substrate against destructive action of irradiation and as result, the absorbance of Vitro-Skin® testing substrate (IMS Testing Group, Milford, Conn.) is decreased almost as much as at the condition when this substrate was not protected at all (FIG. 9). It is especially obvious in the range 250 nm-330 nm although at longer wavelengths some increase in the absorbance is observed.

Figure 12:
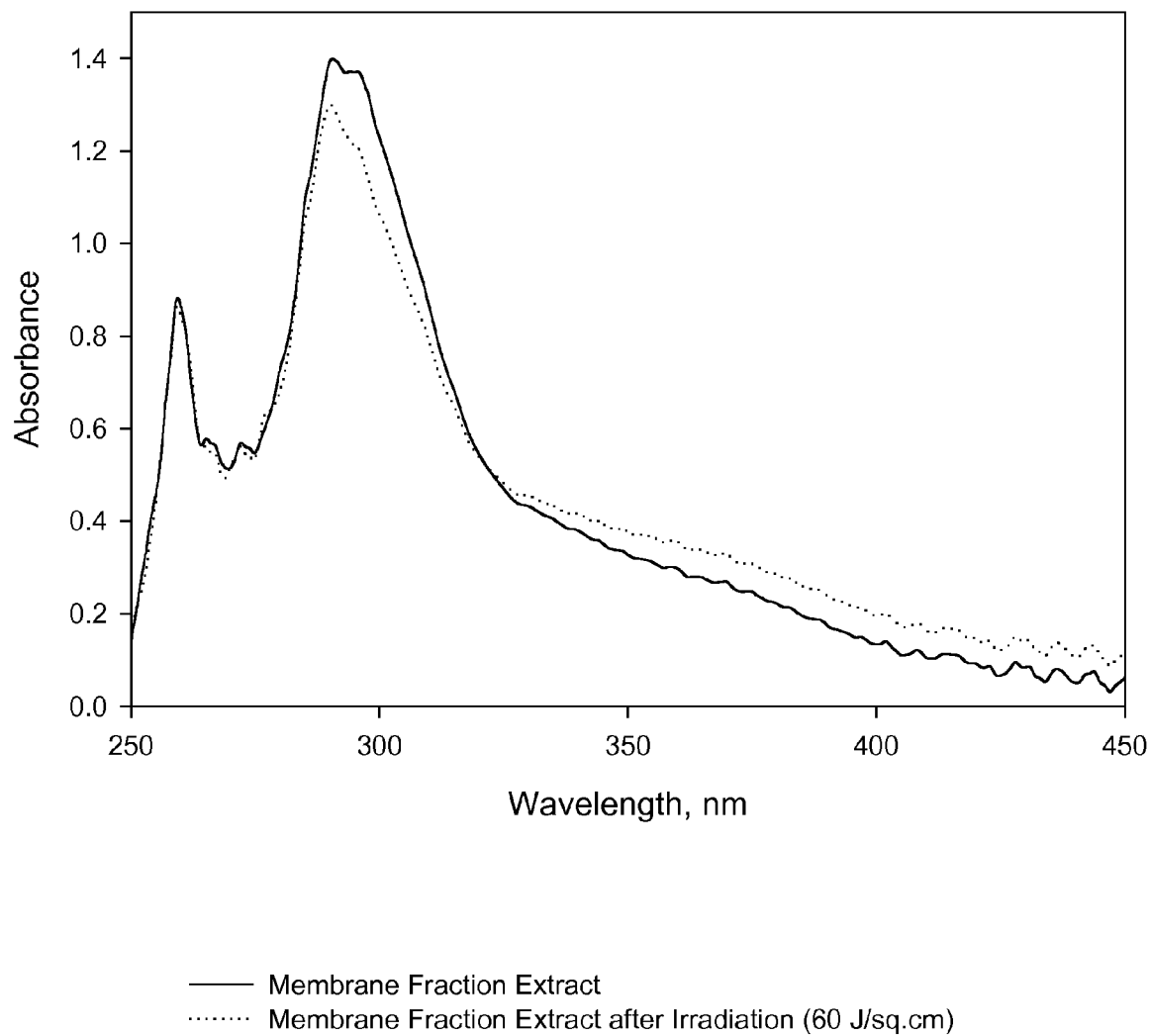
FIG. 12 is a graph showing the effect of broad spectrum UV radiation on *Camellia* membrane fraction extract applied on Vitro-Skin® testing substrate (IMS Testing Group, Milford, Conn.).

The irradiation of membrane fraction extract produced very different effect on its absorbance spectra (FIG. 12). For example, irradiation did not initiate any changes in spectral range 250-285 mm. As discussed, this particular range of spectra was very significantly impacted by the destruction of irradiated Vitro-Skin® testing substrate (IMS Testing Group, Milford, Conn.) and therefore comparison of the spectra suggest that the destruction of the substrate was completely prevented by the presence of membrane fraction extract on its surface.

However, certain changes in membrane fraction extract spectra were registered. For example, the absorbance was slightly decreased in the range 290-320 nm and it was accompanied with small increase of absorbance at longer wavelengths. It should be especially pointed out, that membrane fraction extract was proven to be very effective in the range of spectra where nucleic acids and aromatic amino acids have characteristic peaks at 260 nm and 280 nm subsequently. Thus, effect of membrane fraction extract allows the use of this product as a prospective UV protective ingredient for topical applications.

Figure 13:
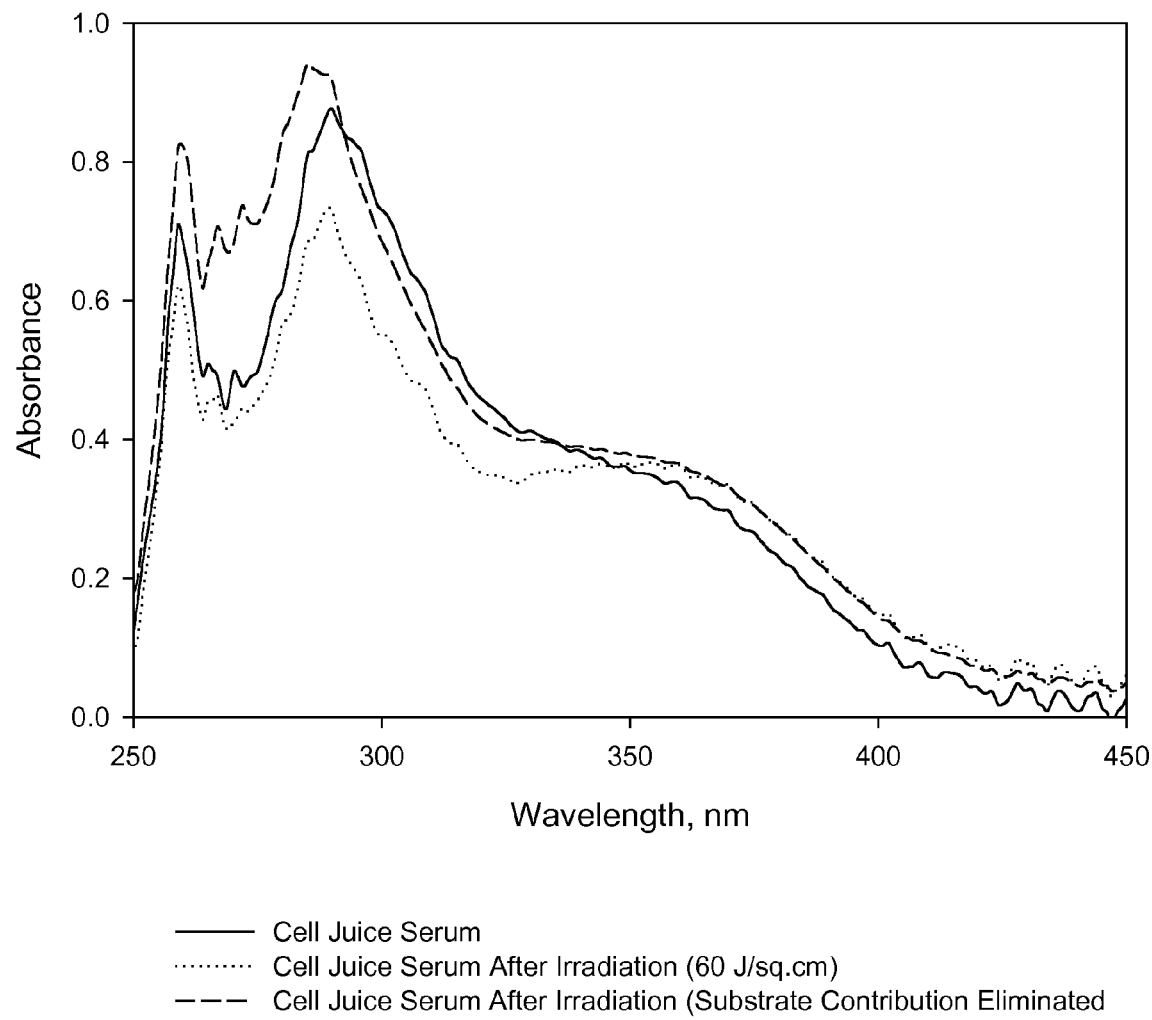
FIG. 13 is a graph showing the effect of broad spectrum UV radiation on *Camellia* cell juice serum applied on Vitro-Skin® testing substrate (IMS Testing Group, Milford, Conn.).
Figure 14:
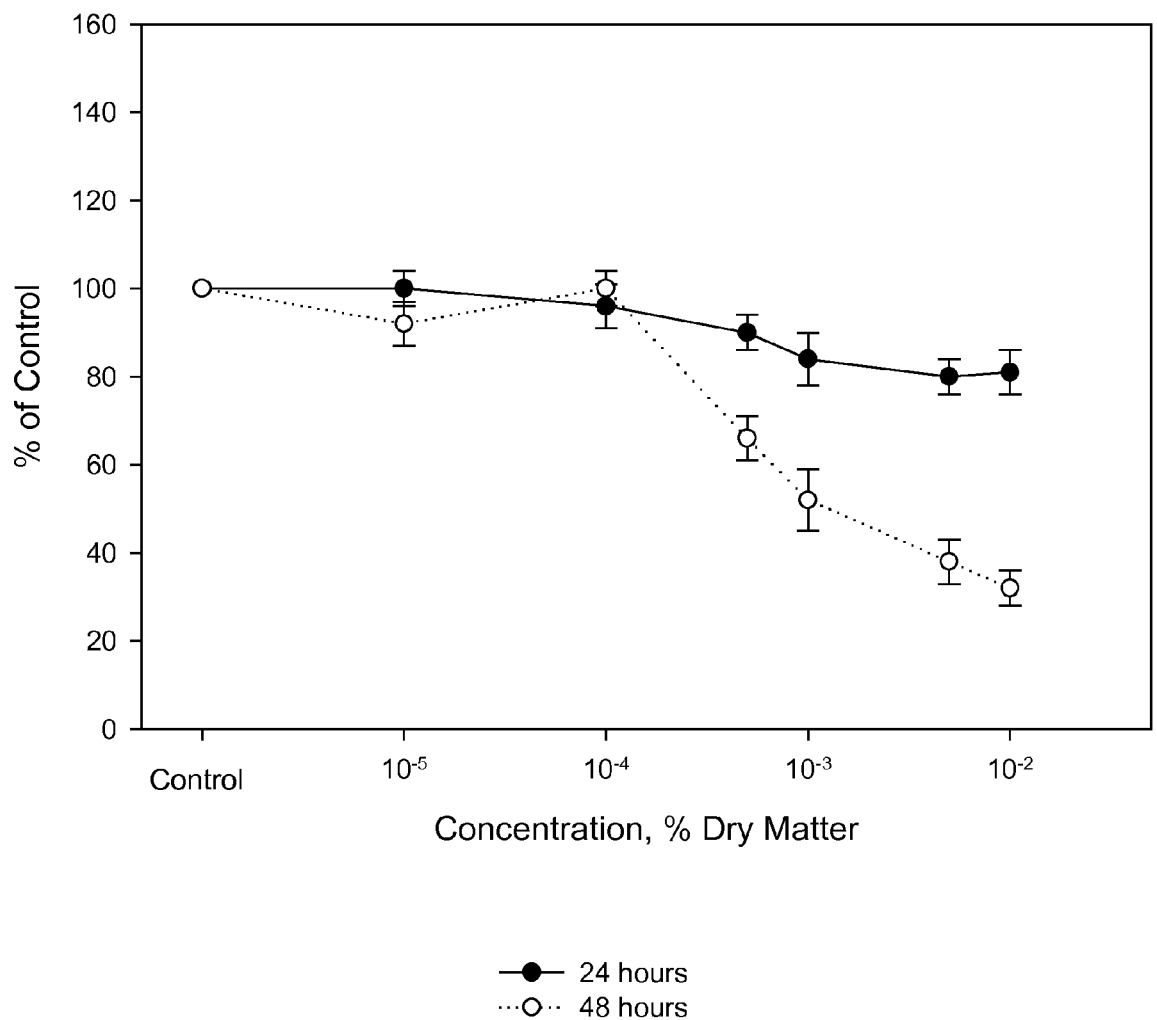
FIG. 14 is a graph showing the effect of white tea extract on MDA-MB-435S cells cultivated for 24 hours and 48 hours.
Figure 15:
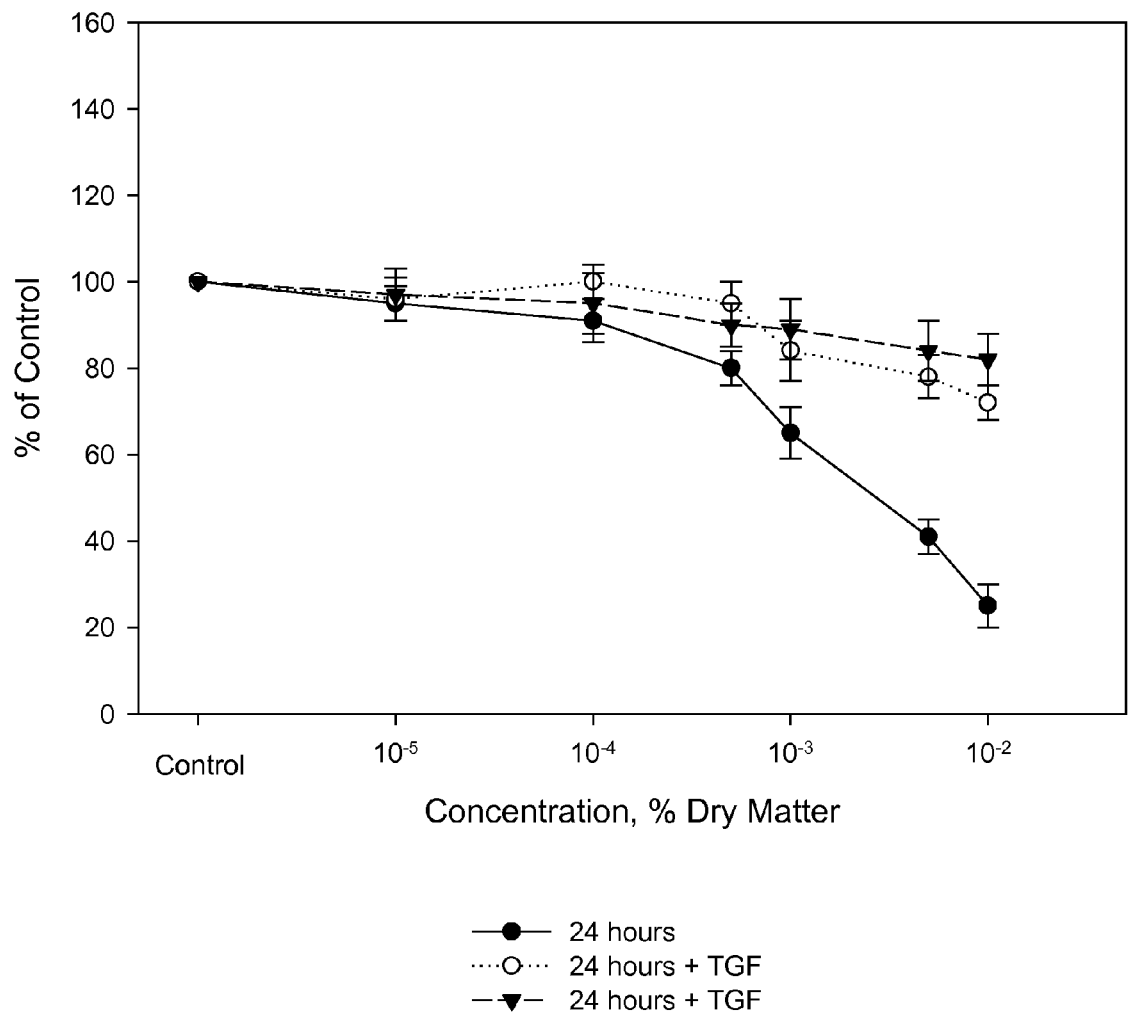
FIG. 15 is a graph showing the effect of white tea extract on MCF-7 cells cultivated for 24 hours (control) and for 24 hours and 48 hours in the presence of 5 ng/ml TGF-β.
Figure 16:
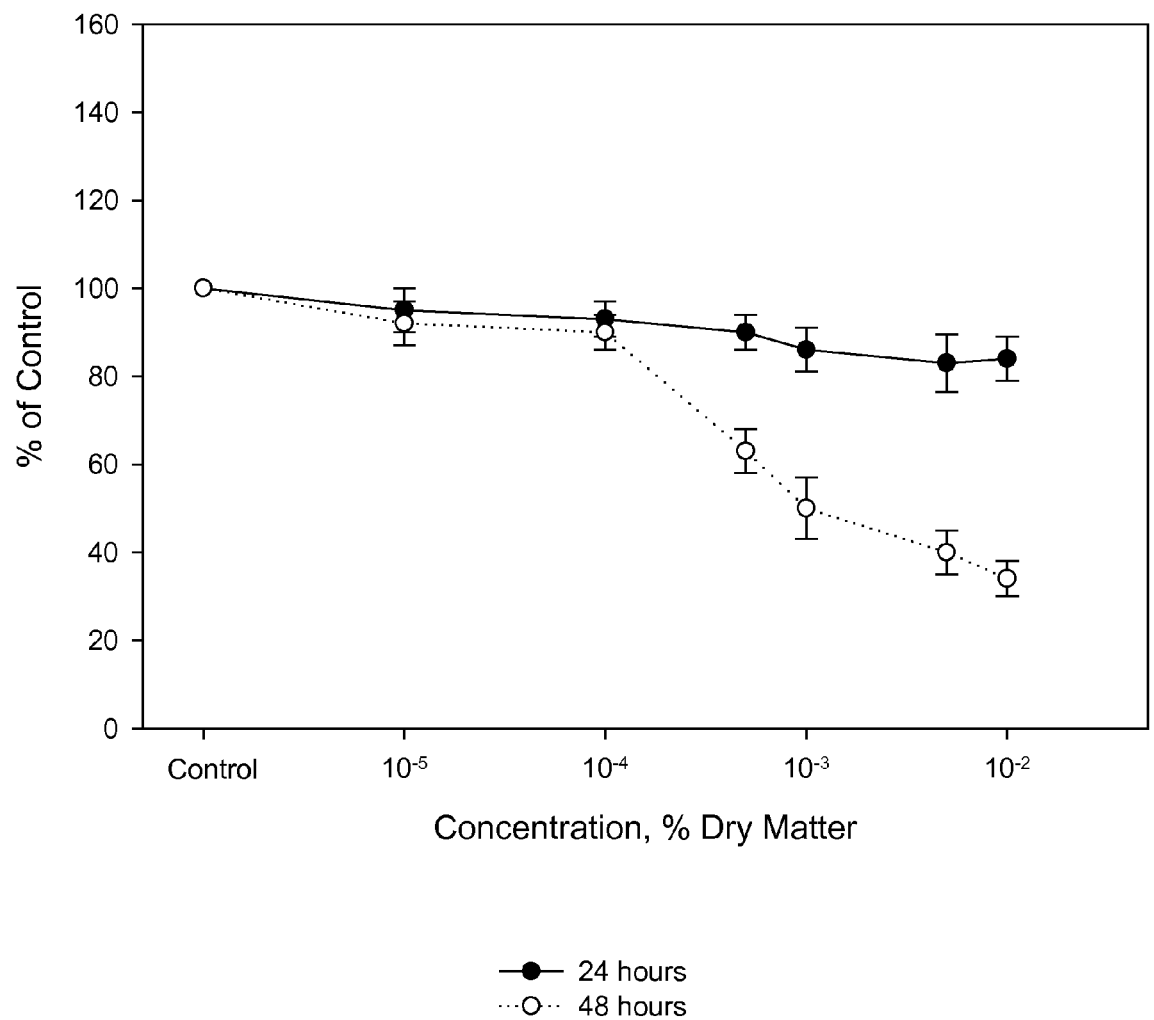
FIG. 16 is a graph showing the effect of cell walls fraction extract on MDA-MB-435S cells cultivated for 24 hours and 48 hours.
Figure 17:
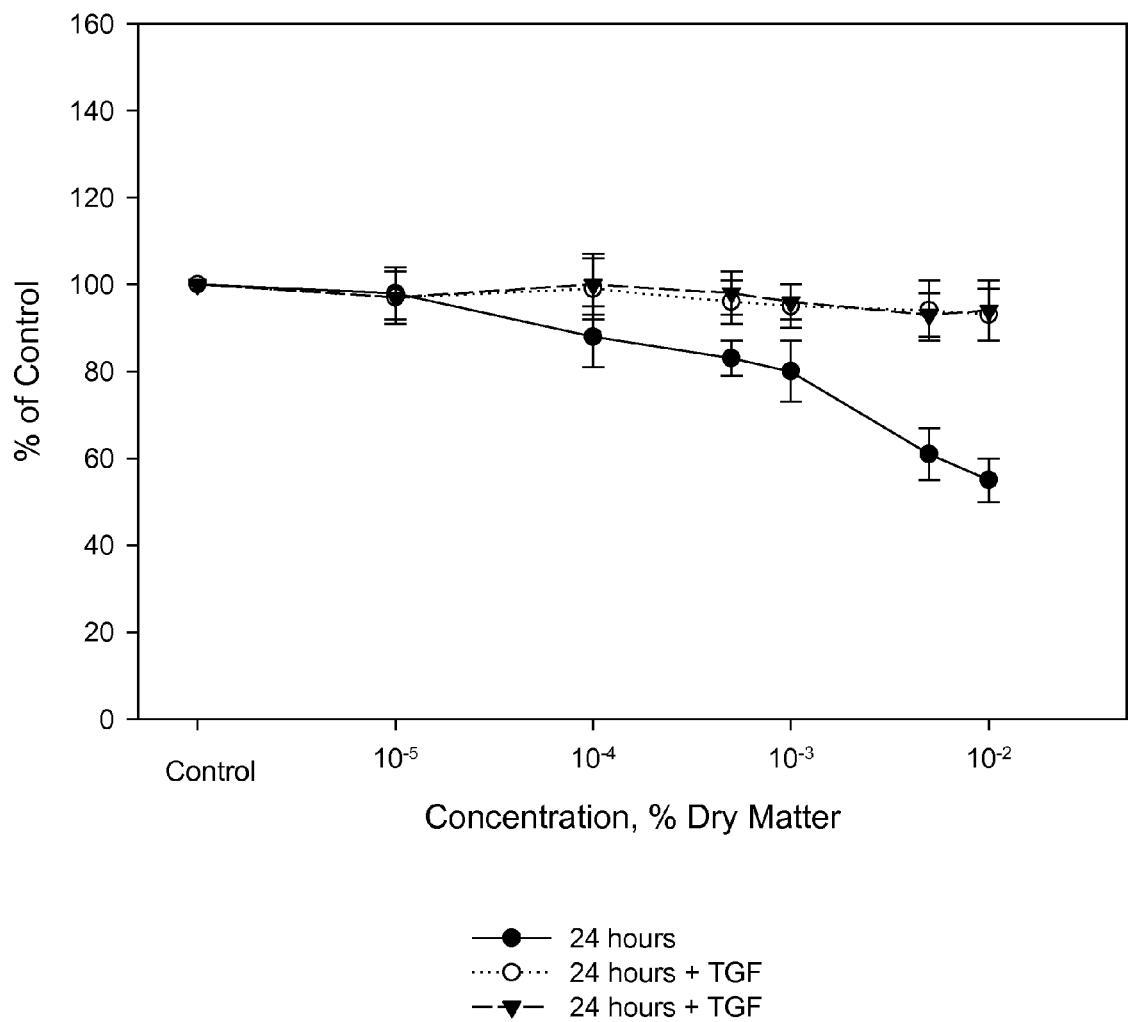
FIG. 17 is a graph showing the effect of cell walls fraction extract on MCF-7 cells cultivated for 24 hours (control) and for 24 hours and 48 hours in the presence of 5 ng/ml TGF-β.
Figure 18:
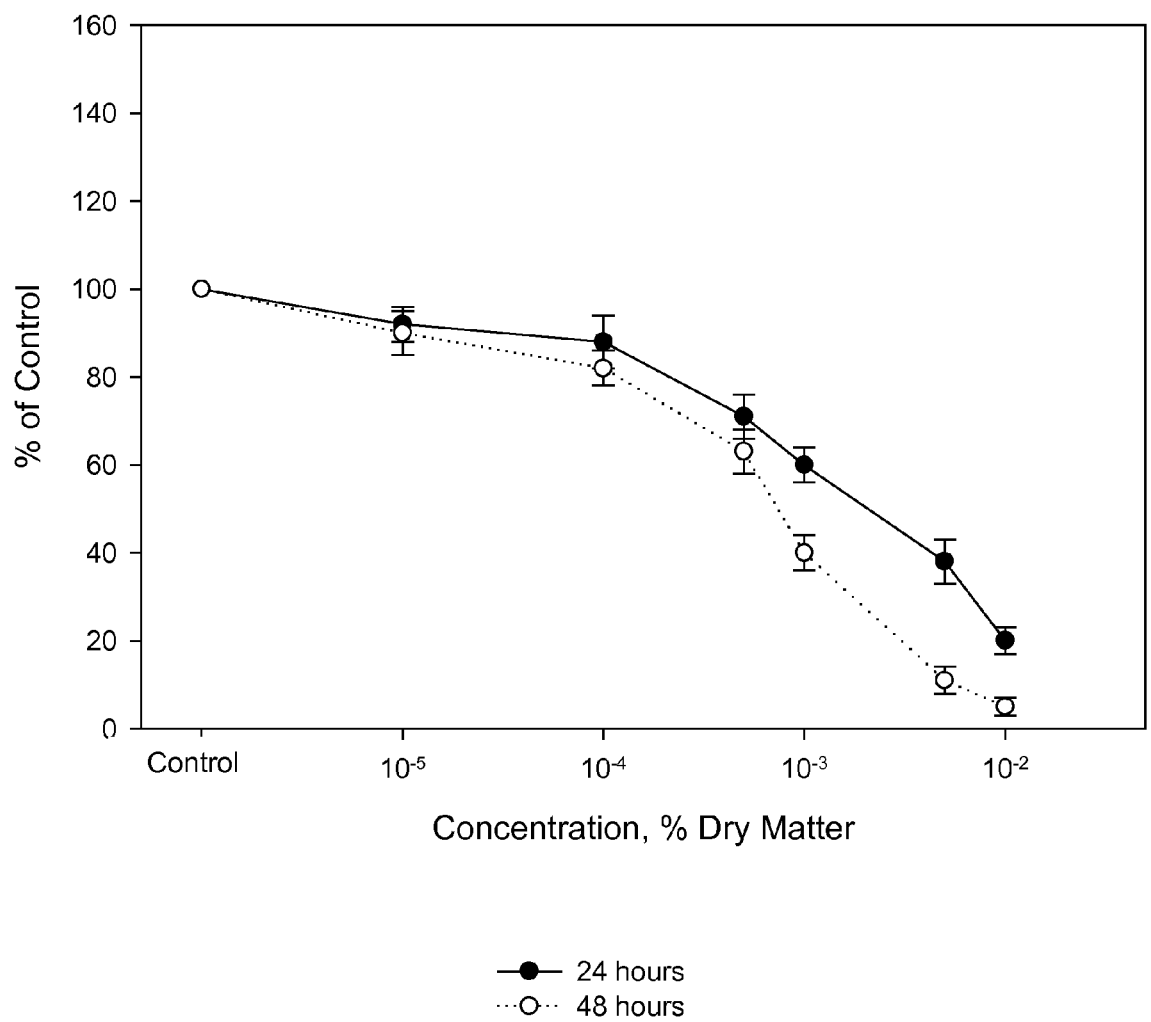
FIG. 18 is a graph showing the effect of membrane fraction extract on MDA-MB-435S cells cultivated for 24 hours and 48 hours.
Figure 19:
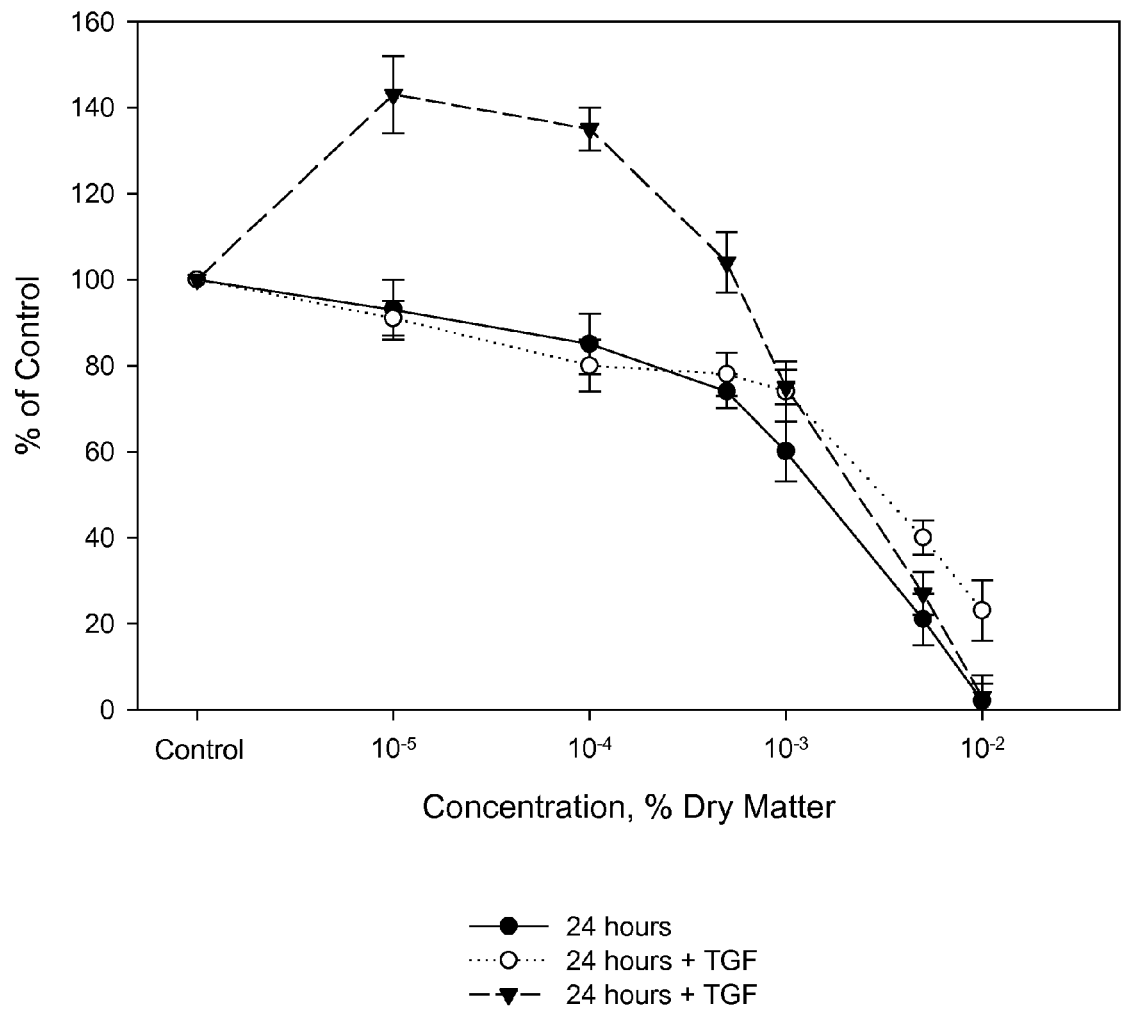
FIG. 19 is a graph showing the effect of membrane fraction extract on MCF-7 cells cultivated for 24 hours (control) and for 24 hours and 48 hours in the presence of 5 ng/ml TGF-β.
Figure 20:
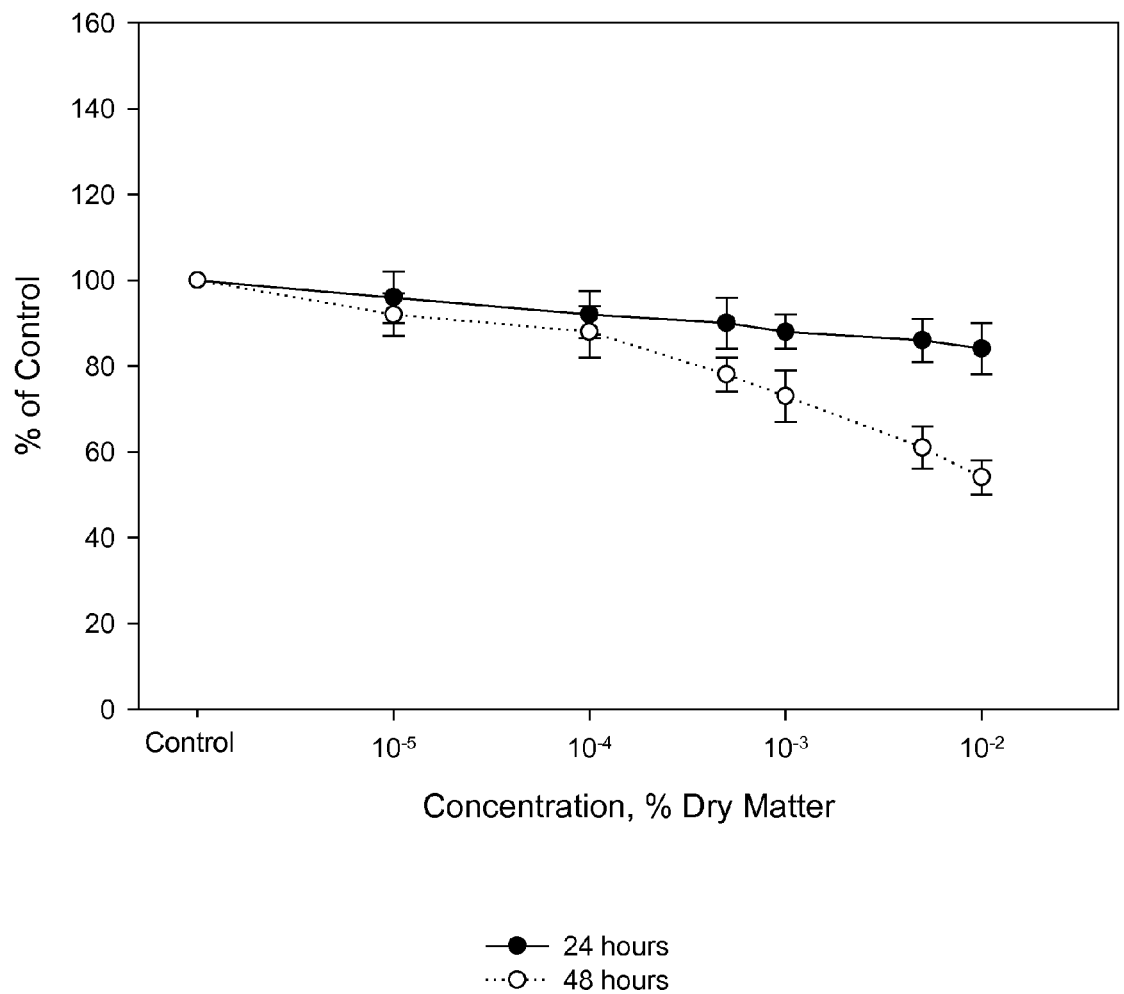
FIG. 20 is a graph showing the effect of cell juice serum on MDA-MB-435S cells cultivated for 24 hours and 48 hours.
Figure 21:
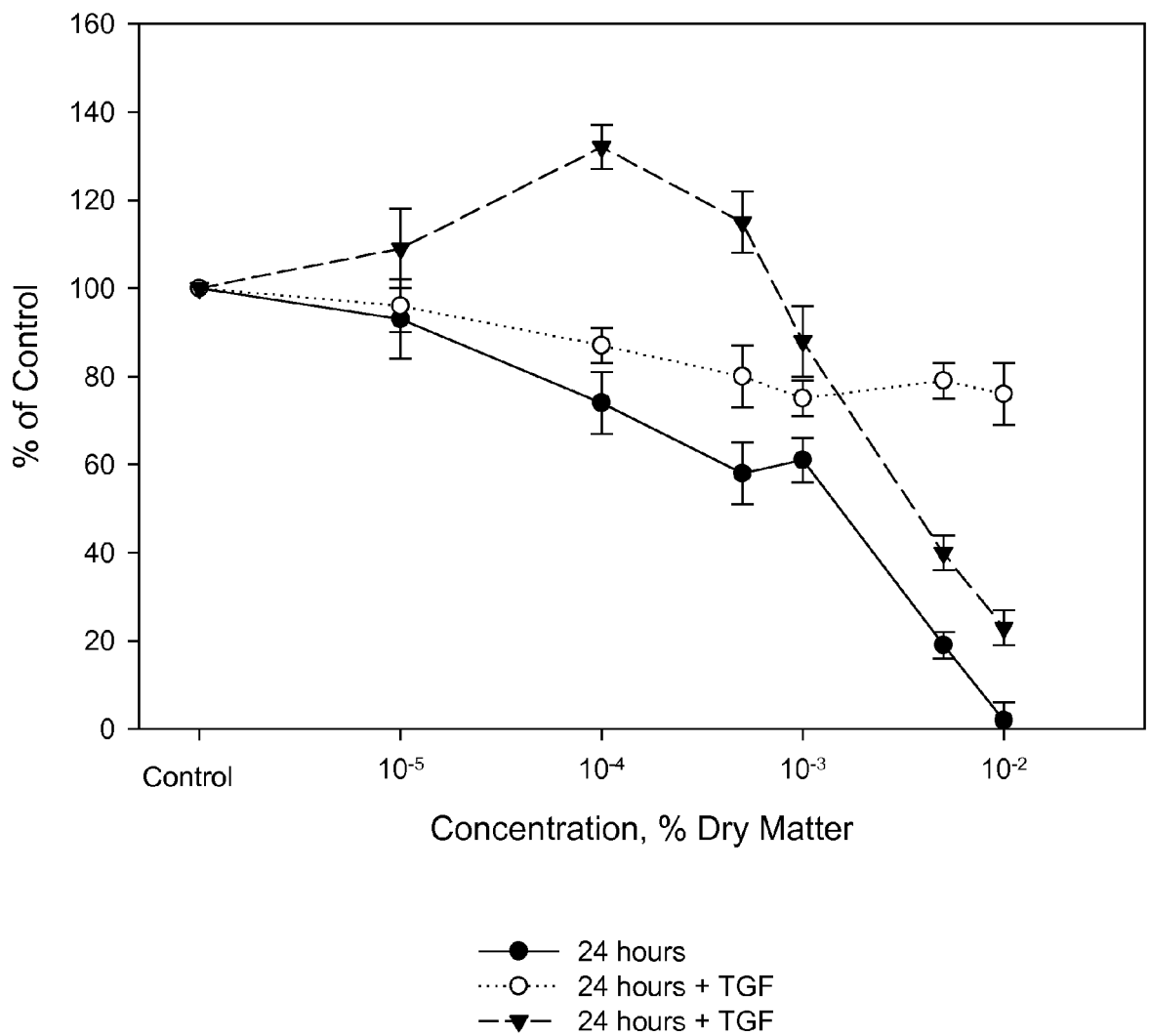
FIG. 21 is a graph showing the effect of cell juice serum on MCF-7 cells cultivated for 24 hours (control) and for 24 hours and 48 hours in the presence of 5 ng/ml TGF-β.
Figure 22:
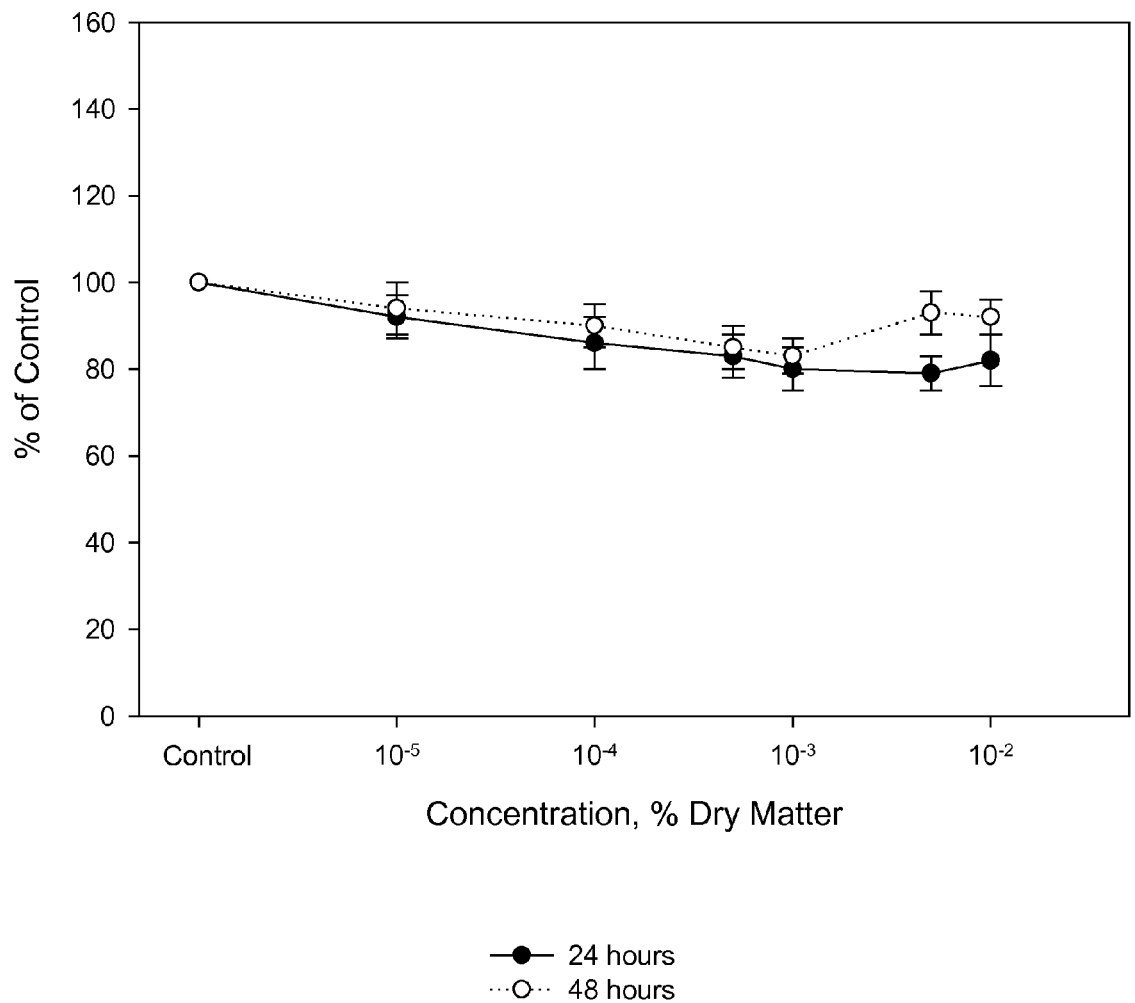
FIG. 22 is a graph showing the effect of white tea extract on Mono Mac 6 cells cultivated for 24 and 48 hours.
Figure 23:
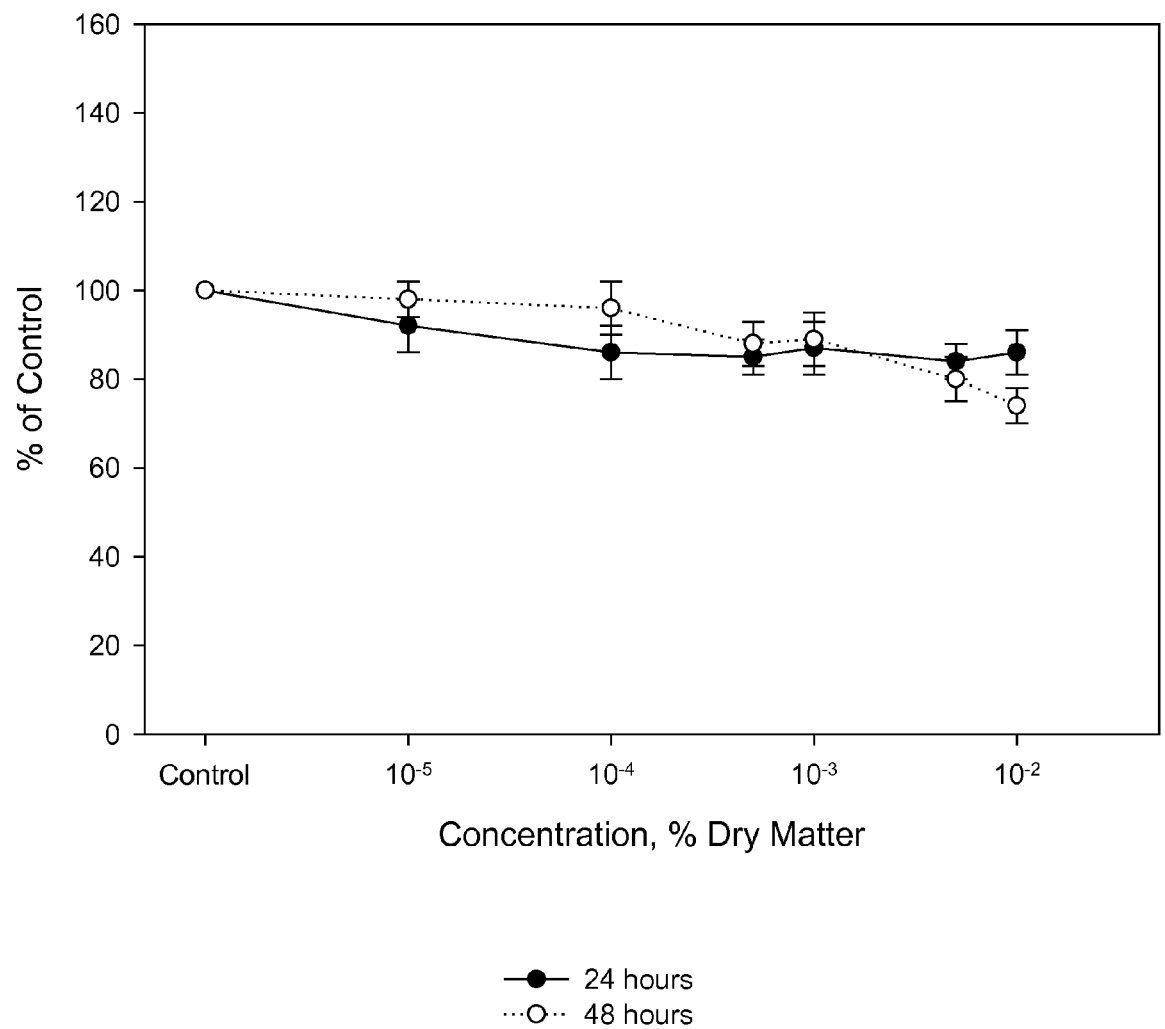
FIG. 23 is a graph showing the effect of white tea extract on Mono Mac 6 cells cultivated for 24 hours and 48 hours in the presence of 10 nM PMA.
Figure 24:
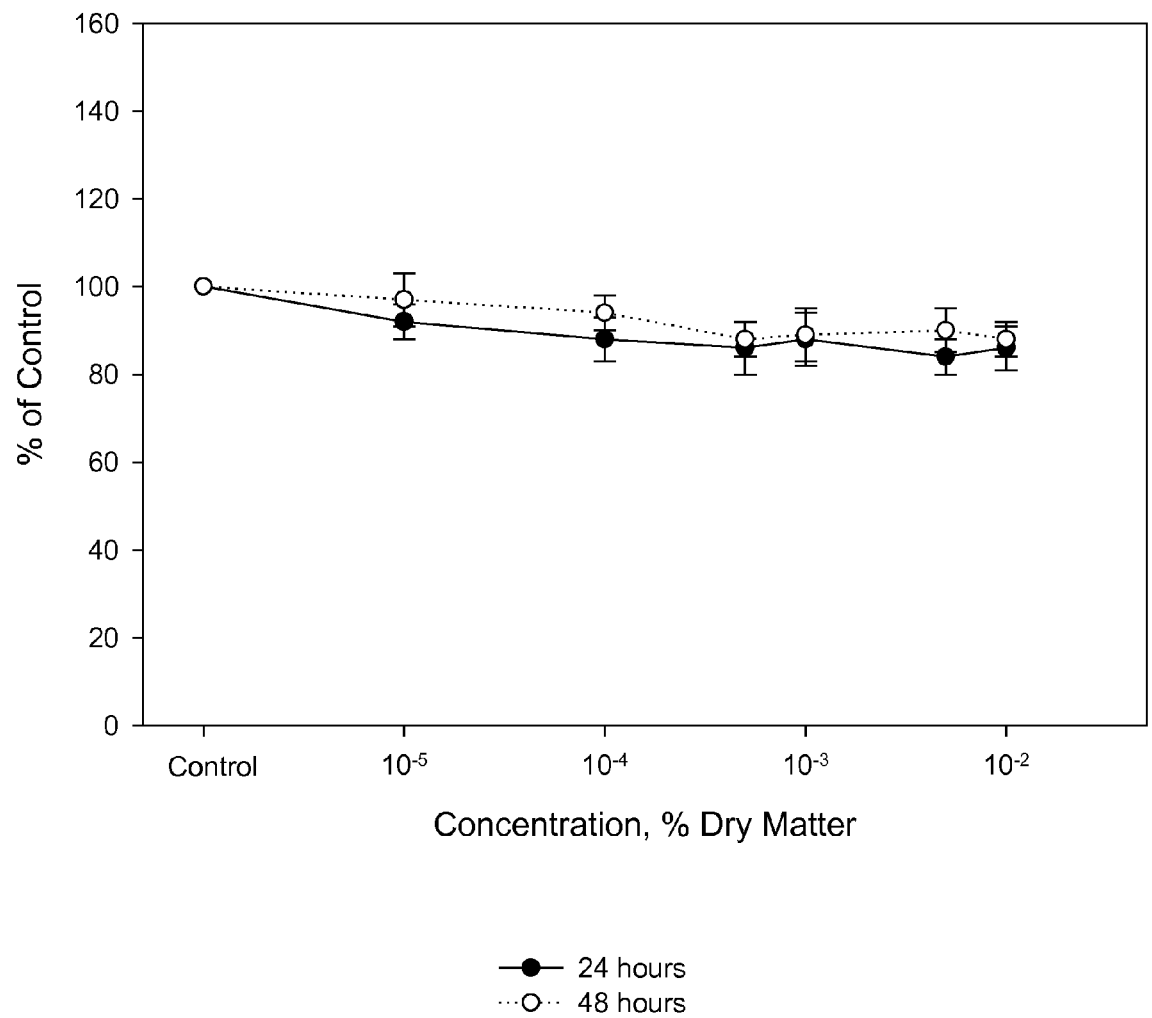
FIG. 24 is a graph showing the effect of cell walls fraction extract on Mono Mac 6 cells cultivated for 24 hours and 48 hours.
Figure 25:
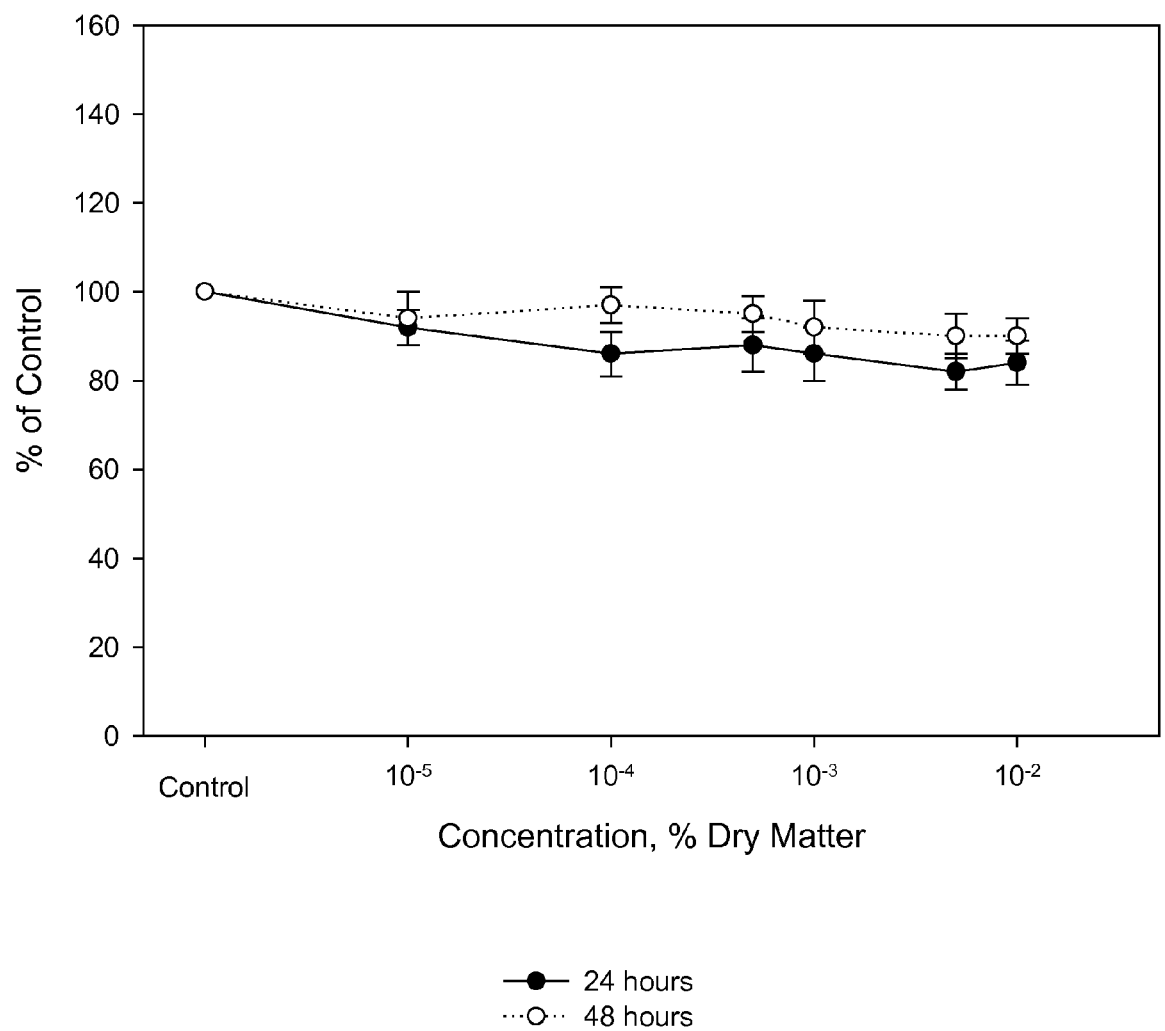
FIG. 25 is a graph showing the effect of cell walls fraction extract on Mono Mac 6 cells cultivated for 24 hours and 48 hours in the presence of 10 nM PMA.
Figure 26:
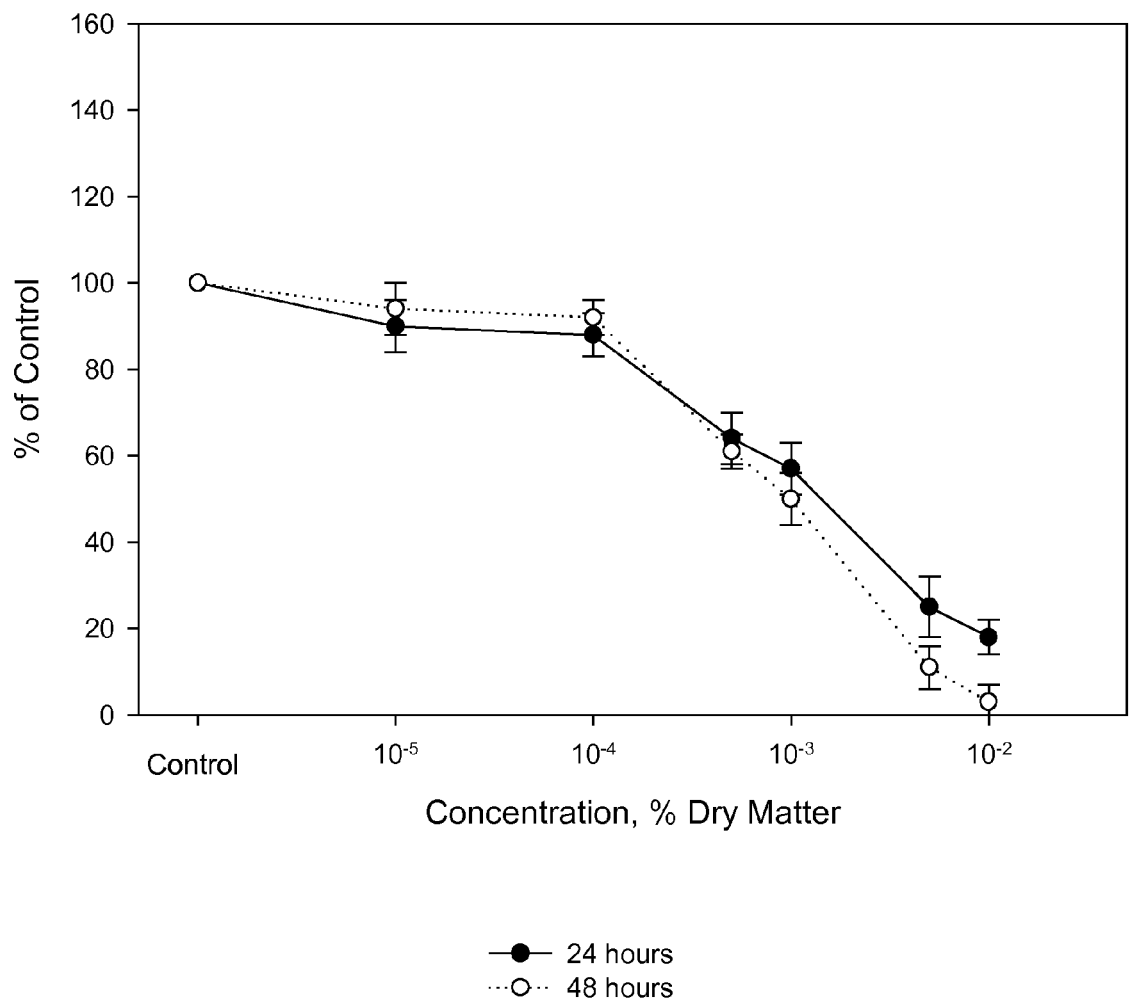
FIG. 26 is a graph showing the effect of membrane fraction extract on Mono Mac 6 cells cultivated for 24 hours and 48 hours.
Figure 27:
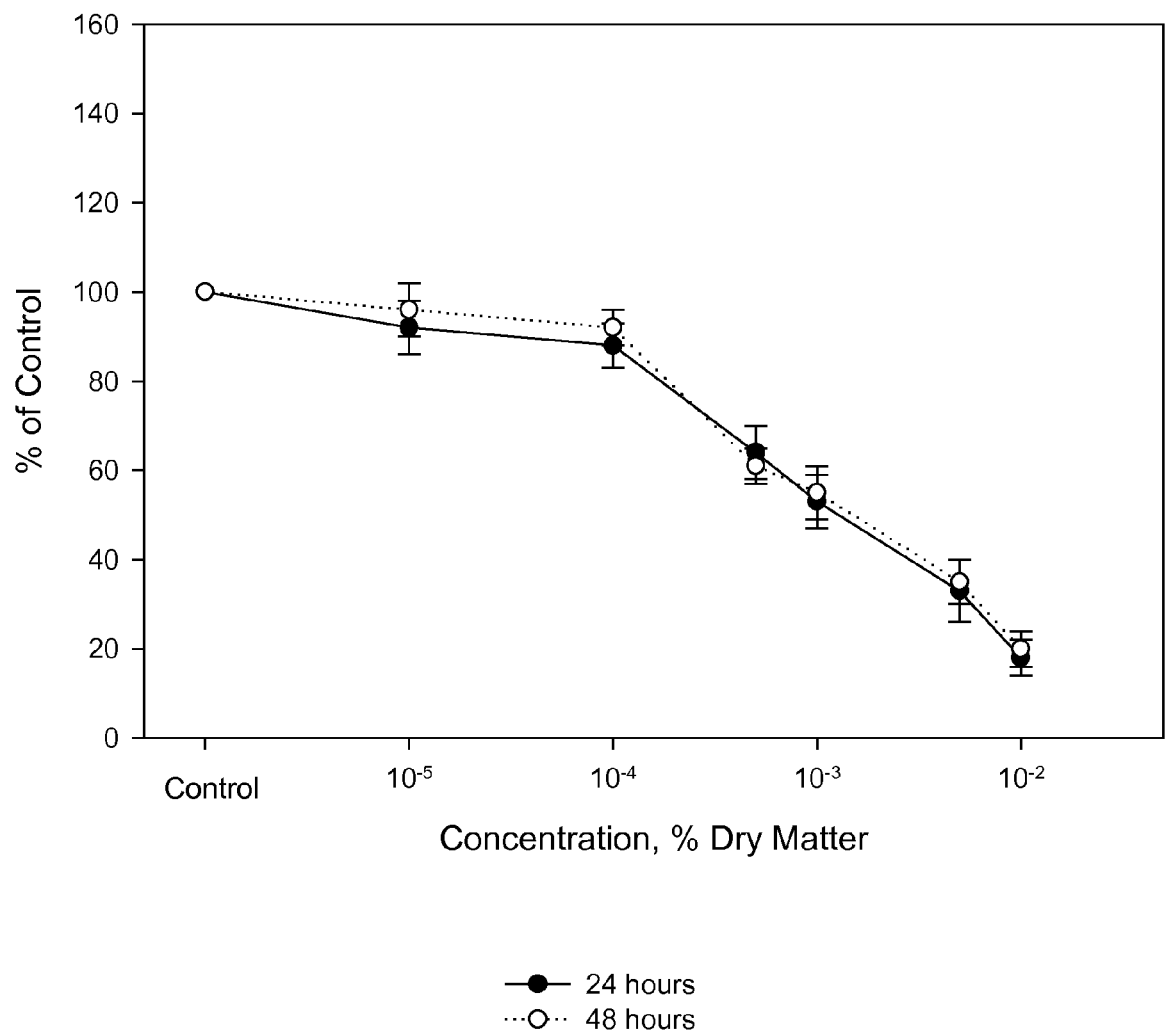
FIG. 27 is a graph showing the effect of membrane fraction extract on Mono Mac 6 cells cultivated for 24 hours and 48 hours in the presence of 10 nM PMA.
Figure 28:
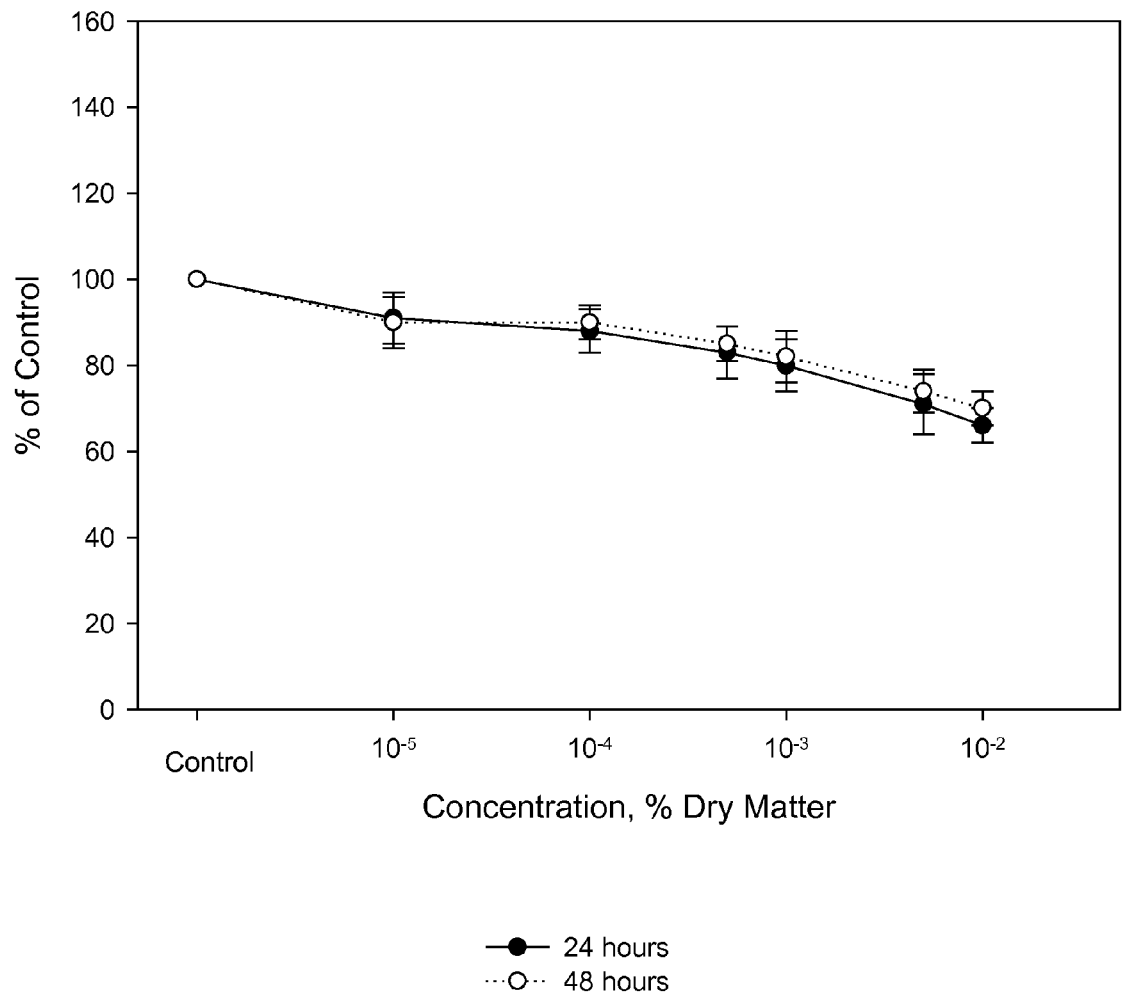
FIG. 28 is a graph showing the effect of cell juice serum on Mono Mac 6 cells cultivated for 24 hours and 48 hours.
Figure 29:
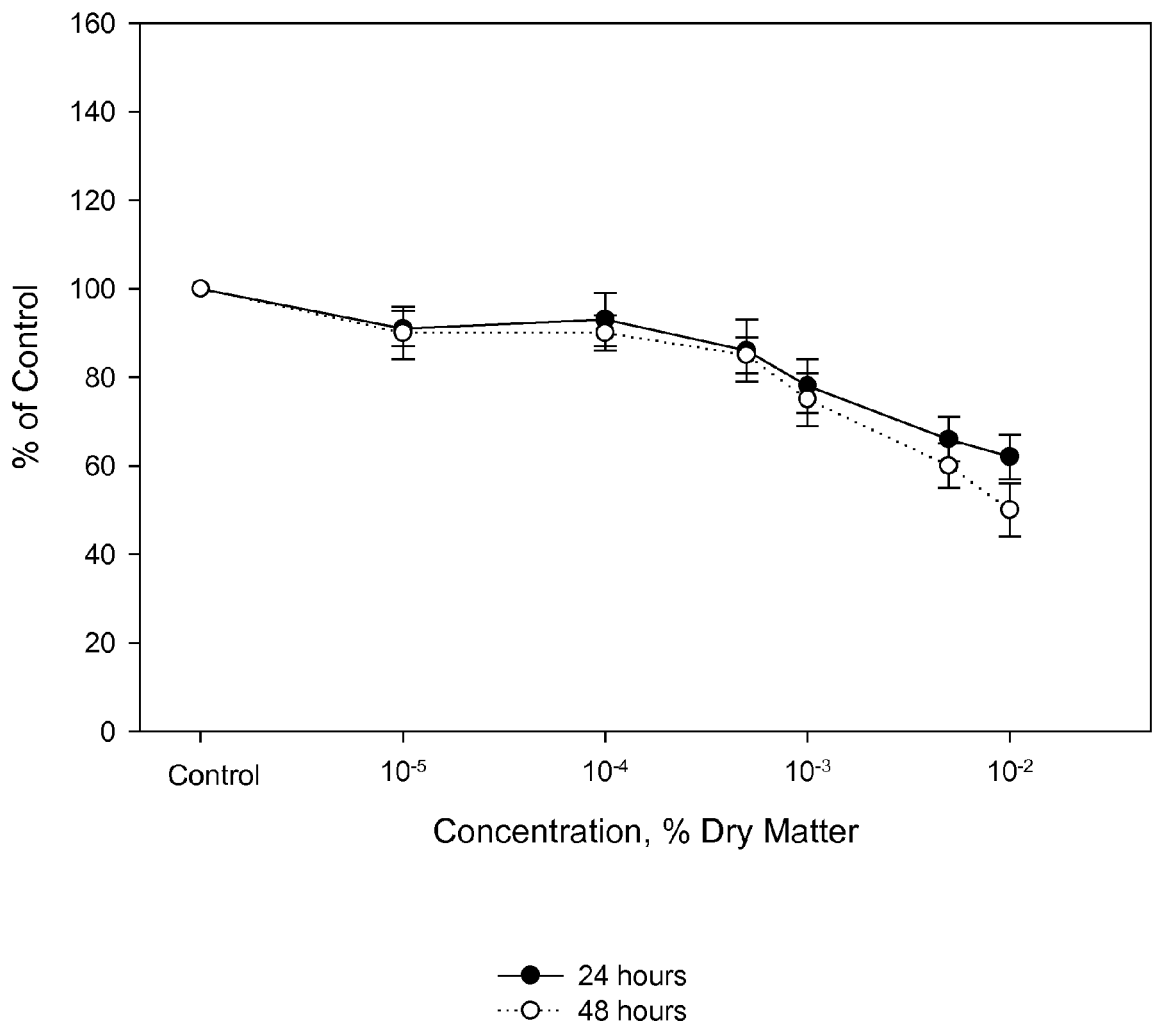
FIG. 29 is a graph showing the effect of cell juice serum on Mono Mac 6 cells cultivated for 24 hours and 48 hours in the presence of 10 nM PMA.
Figure 30:
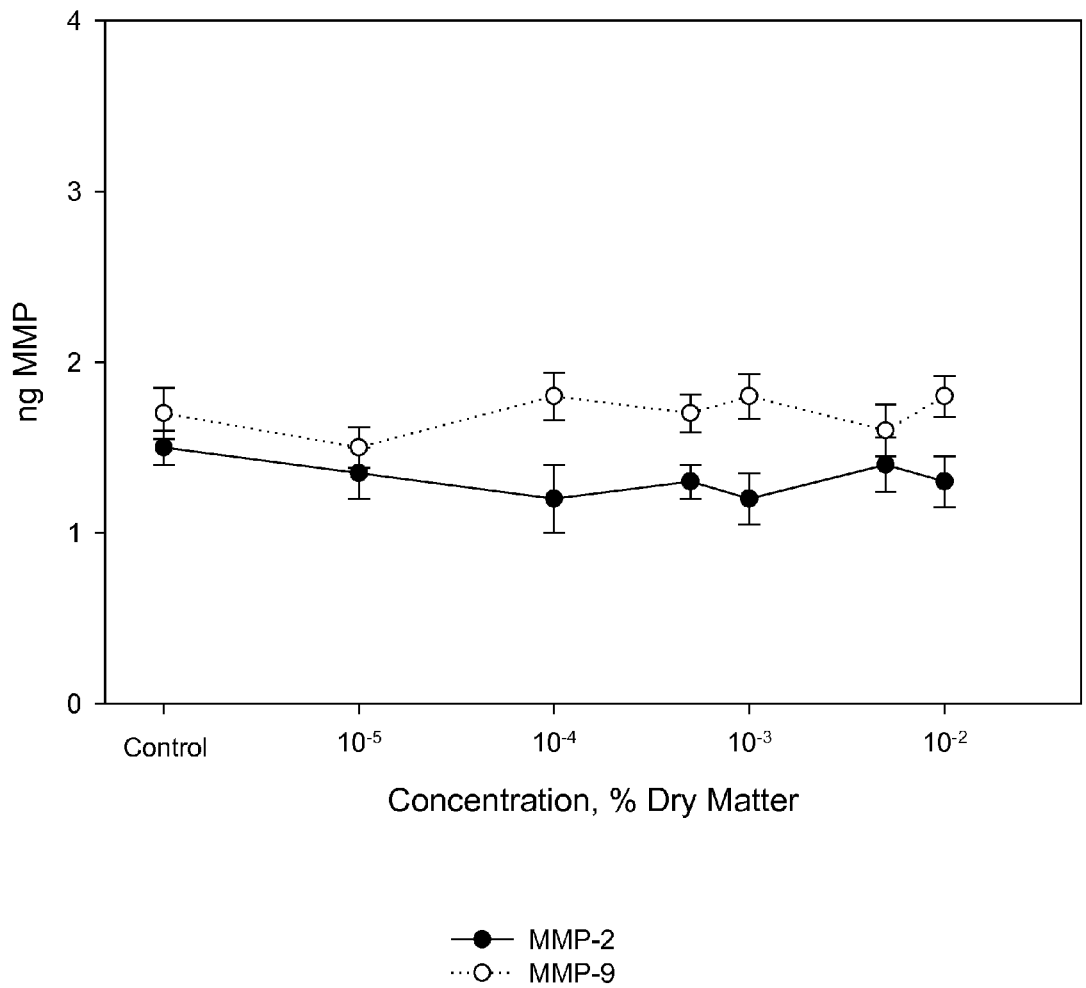
FIG. 30 is a graph showing the effect of white tea extract on level of MMPs secreted by PMA stimulated Mono Mac 6 cells.
Figure 31:
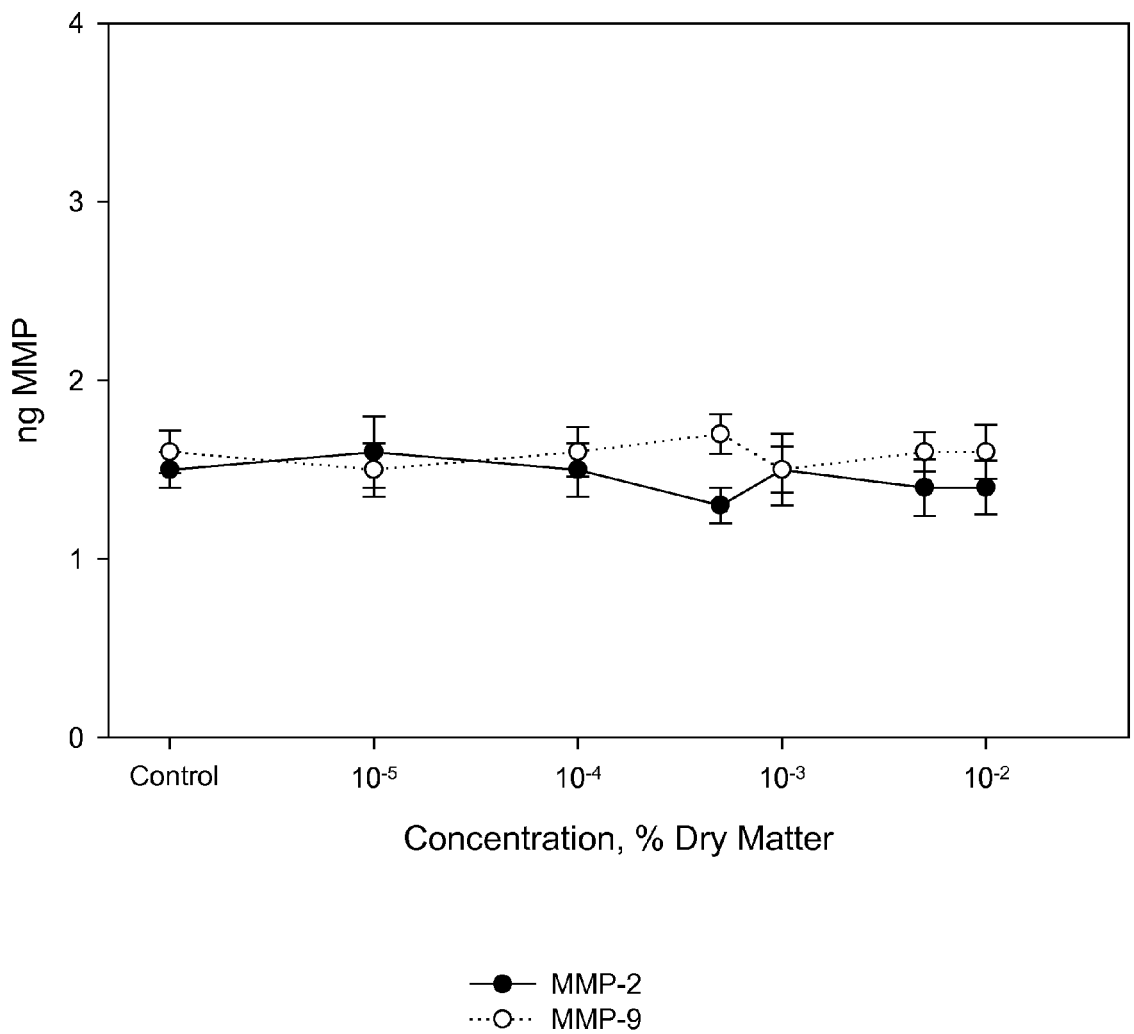
FIG. 31 is a graph showing the effect of cell walls fraction extract on level of MMPs secreted by PMA stimulated Mono Mac 6 cells.
Figure 32:
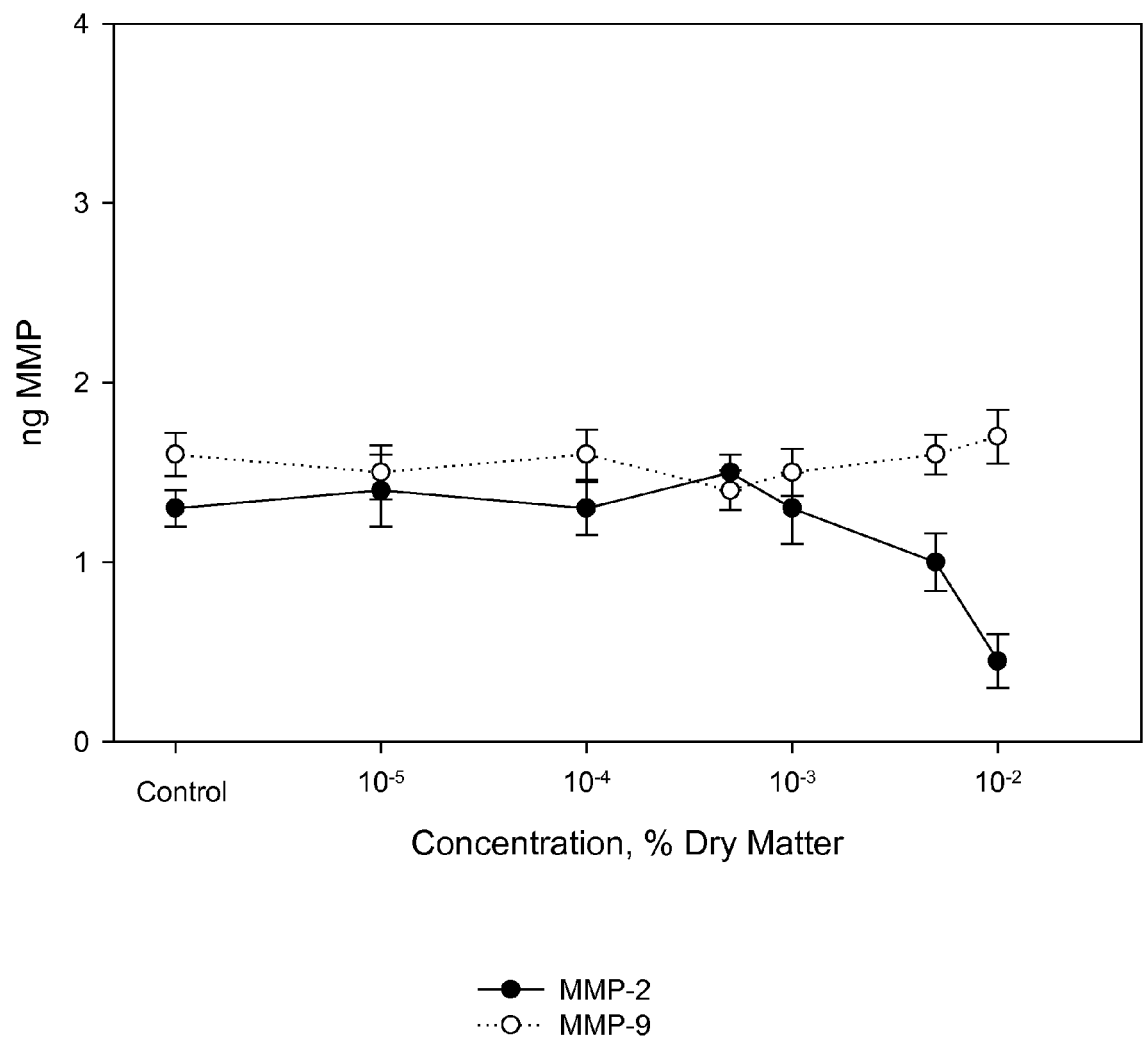
FIG. 32 is a graph showing the effect of membrane fraction extract on level of MMPs secreted by PMA stimulated Mono Mac 6 cells.
Figure 33:
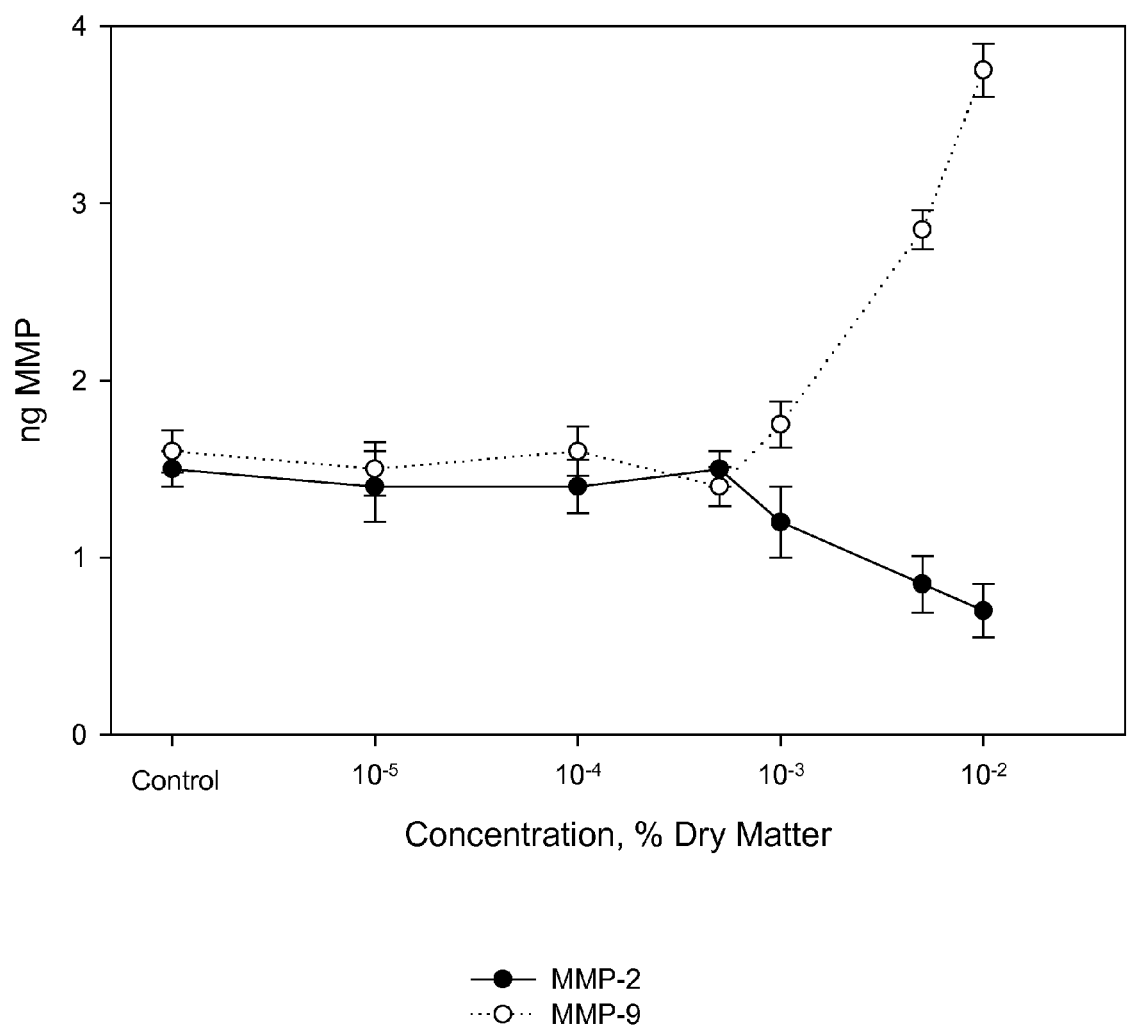
FIG. 33 is a graph showing the effect of cell juice serum on level of MMPs secreted by PMA stimulated Mono Mac 6 cells.
Figure 34:
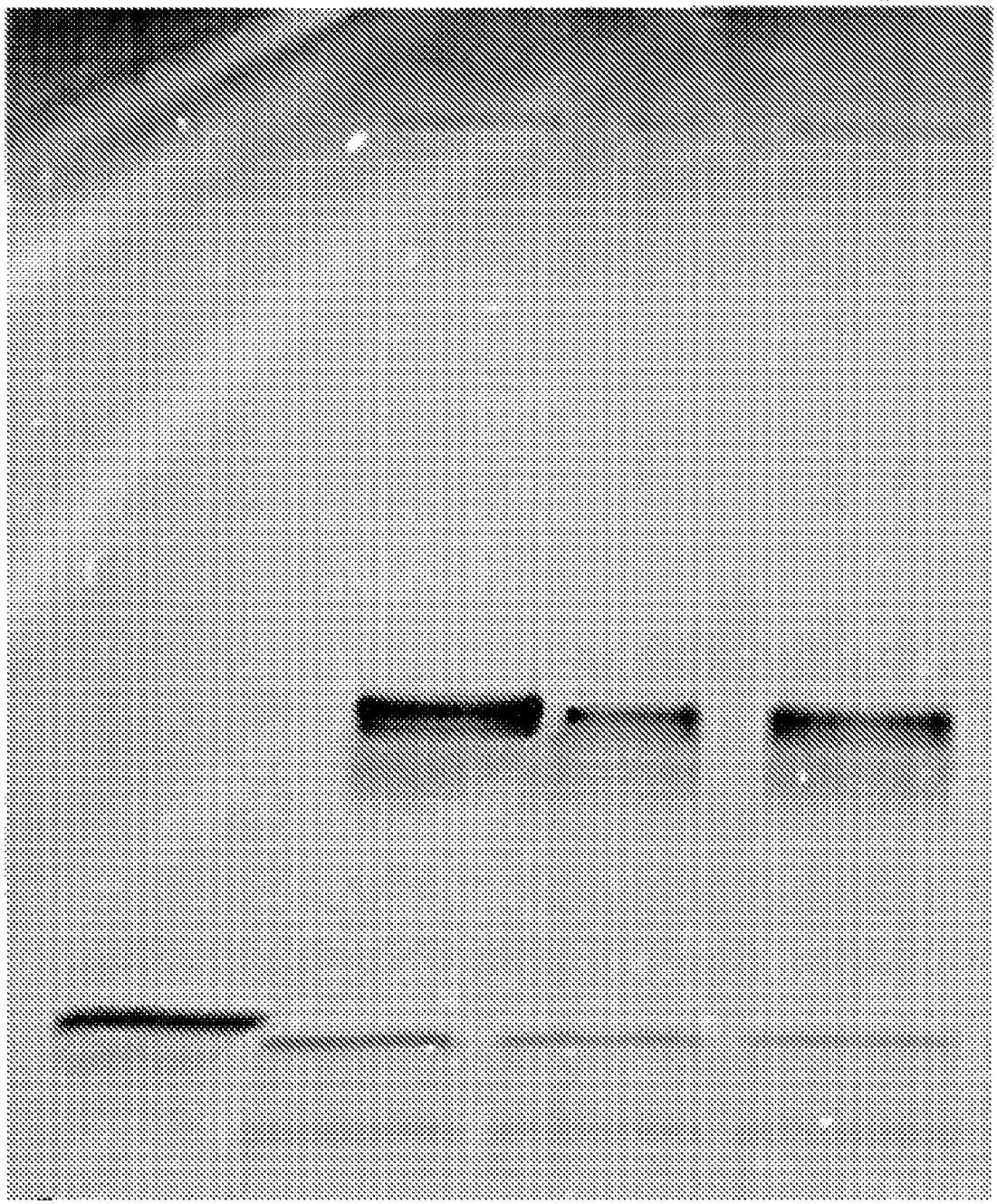
FIG. 34 is a gelatin zymogram of culture media collected after 48 hours exposure of Mono Mac 6 cells to white tea extract, along with culture media collected from cells cultured in the absence (U) or presence (S) of 10 nM PMA, but in the absence of the *Camellia* compositions.
Figure 35:
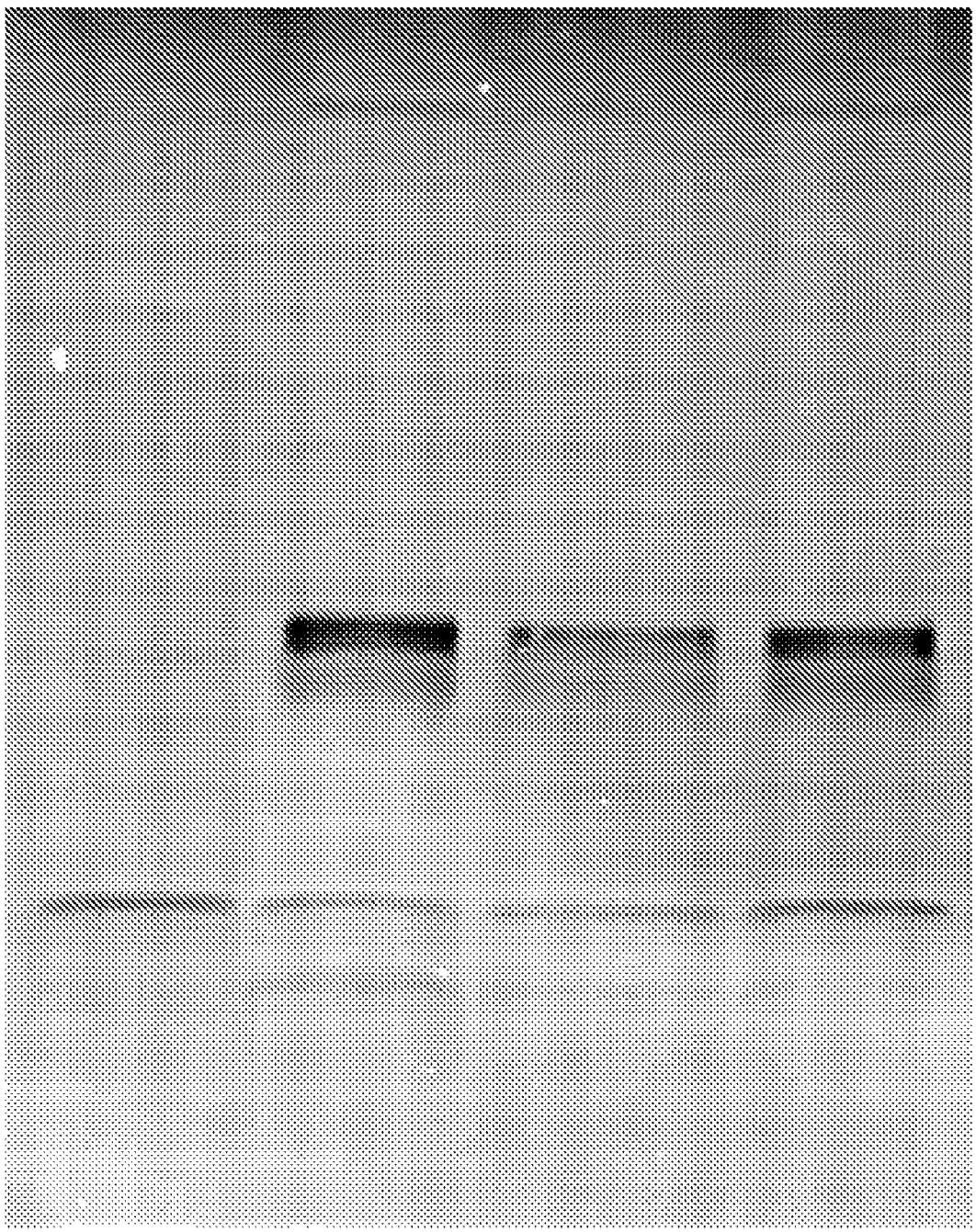
FIG. 35 is a gelatin zymogram of culture media collected after 48 hours exposure of Mono Mac 6 cells to cell walls fraction extract, along with culture media collected from cells cultured in the absence (U) or presence (S) of 10 nM PMA, but in the absence of the *Camellia* compositions.
Figure 36:
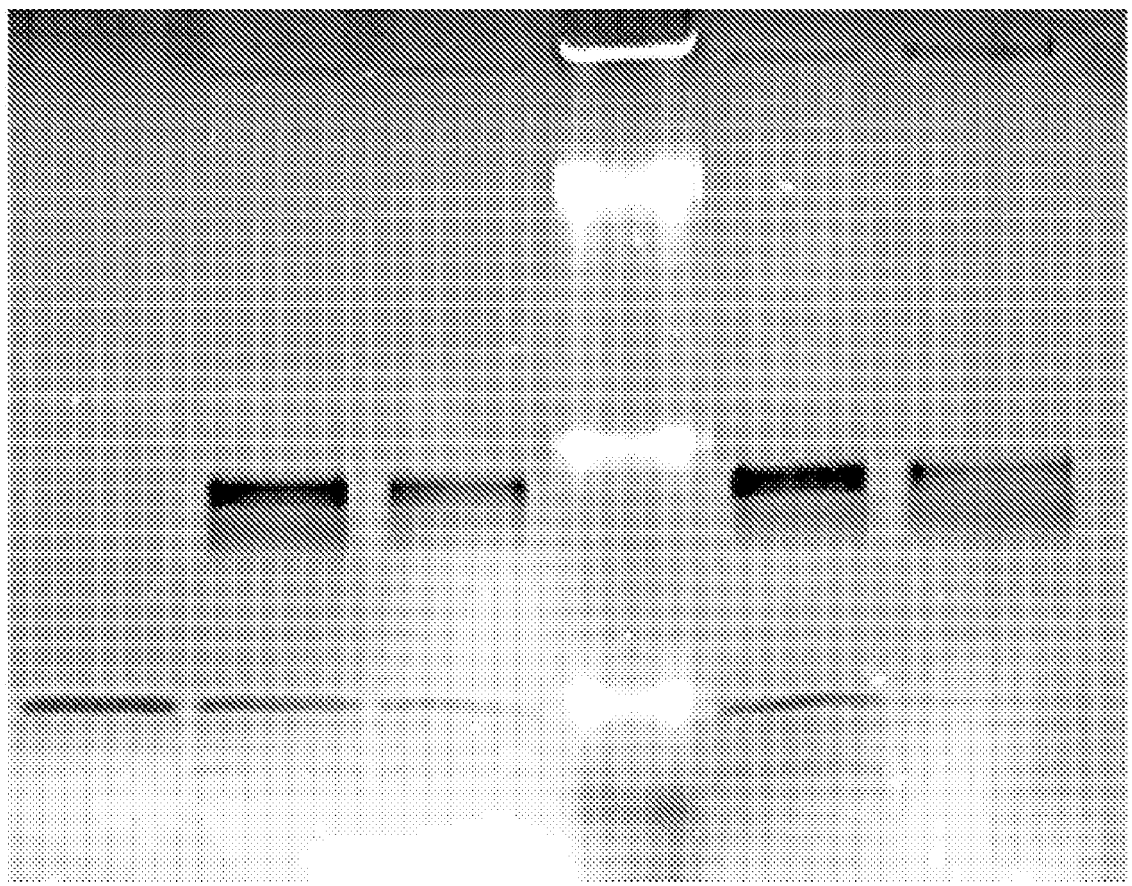
FIG. 36 is a gelatin zymogram of culture media collected after 48 hours exposure of Mono Mac 6 cells to membrane fraction extract, along with culture media collected from cells cultured in the absence (U) or presence (S) of 10 nM PMA, but in the absence of the *Camellia* compositions.
Figure 37:
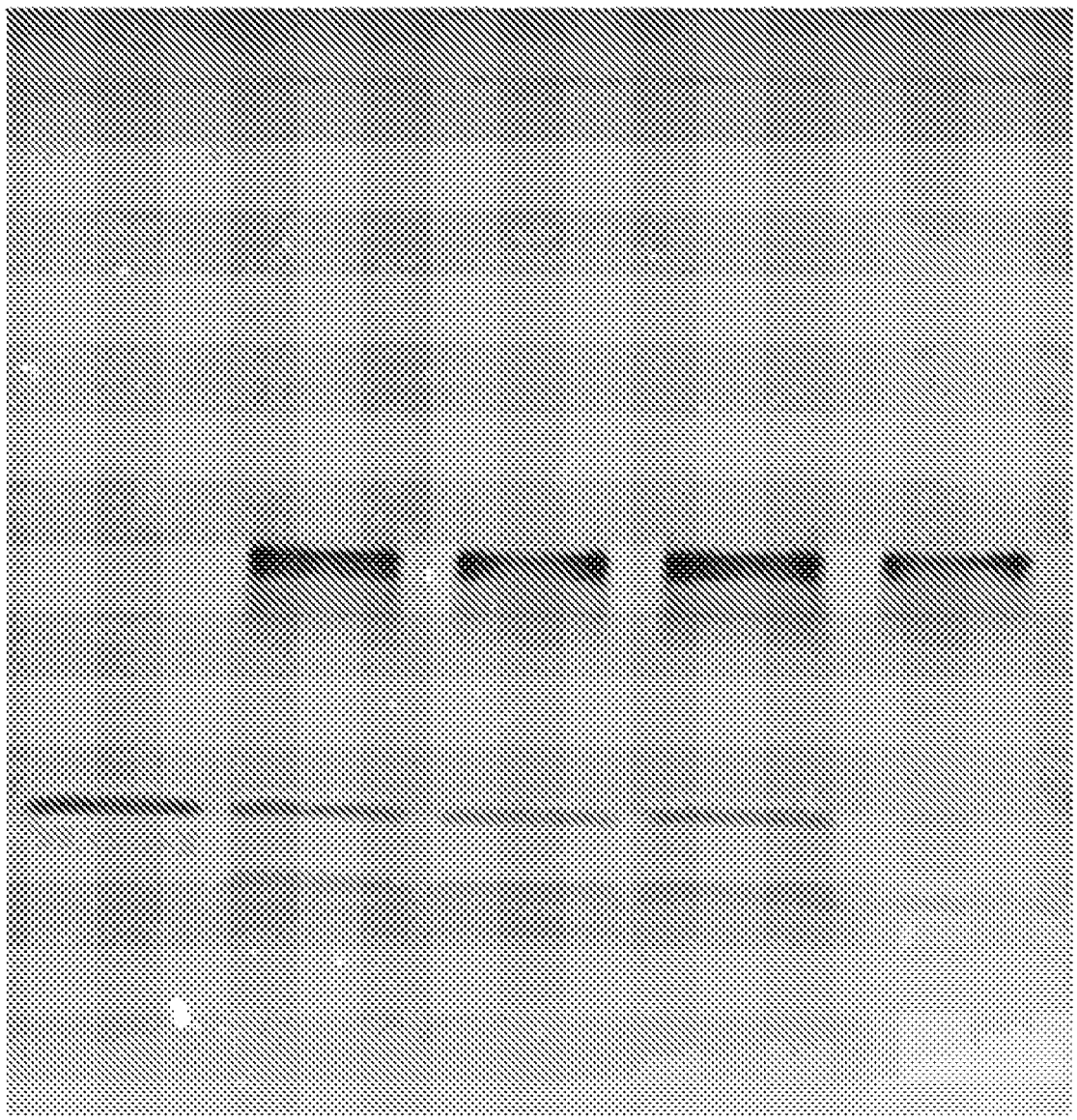
FIG. 37 is a gelatin zymogram of culture media collected after 48 hours exposure of Mono Mac 6 cells to cell juice serum, along with culture media collected from cells cultured in the absence (U) or presence (S) of 10 nM PMA, but in the absence of the *Camellia* compositions.

After irradiation the serum fraction was demonstrating certain changes in its absorbance spectra (FIG. 13).

Generally, these changes can be described as slight decrease of the absorption in the range 250-340 nm and slight increase of the absorption in the range 340-450 nm. It should be noted, that elimination of the possible contribution provided by photo-destruction of Vitro-Skin® testing substrate (IMS Testing Group, Milford, Conn.) (see red curve on spectra above the initial spectra of non-irradiated serum fraction) clearly indicated that substrate was effectively preserved by the application of serum fraction on its surface.

Observations and Conclusions. The above results clearly show that the best of conventional Camellia products—white tea extract—provides relatively weak protection against the destructive action of UV irradiation. The cell walls fraction extract demonstrated properties similar to white tea extract, but membrane fraction extract and cell juice serum have much more potent UV protective properties.

The UV protection properties of Camellia products were found to be increasing in the following sequence: white tea extract=cell walls fraction extract>cell juice serum>membrane fraction extract.

It should be noted, that spectral properties of Camellia products and pattern of the changes of these properties after UV irradiation provide strong evidence that compositions of constituents in white tea extract (control), cell walls fraction extract, membrane fraction extract and cell juice serum all differ and display unique activities. This is of particular interest in the case of novel Camellia compositions where the UV activity described above cannot be attributed to polyphenols as it is with white tea extracts.

Example 10

Comparative Evaluation of Camellia Products: An Overview

Examples 10 through 19 describe methods, results, and analyses relating to experiments conducted to evaluate the range of biological activities related to the modulation of cell functions by the bioactive compositions from Camellia sinensis of the present invention. The primary objective was to evaluate the range of biological activities of products obtained from the methods of the present invention and compare these with activities of the best product obtained by conventional (traditional) tea technology—white tea extract, which was explored as a positive control and compared with the following bioactive compositions of the present invention: (1) cell walls fraction extract of fresh leaves (composition A, as referenced herein); (2) membrane fraction extract (composition B, as referenced herein); and (3) cell juice serum (composition D, as referenced herein).

The tests were conducted to evaluate the effect of these Camellia bioactive compositions on growth patterns of three human cell lines: a myeloid line with characteristics of monocytic leukemia cells (Mono Mac 6) and two breast cancer lines with characteristics of early stages of the malignancy in vivo (MCF-7) and a more highly invasive, metastatic and estrogen insensitive line with characteristics of advanced cancer (MDA-MB-435S).

It was found that conventional white tea extract demonstrated a certain inhibitory effect on metabolic activity of some tumor cells. However, the extent of such inhibition was not significant for all types of tested cells and even when such inhibition was detected, it was generally not complete but rather minimal or modest. The cell walls fraction extract demonstrated properties similar to properties to those of white tea extract.

It is noteworthy that both of the cell juice derivatives: membrane fraction extract and cell juice serum, were much more potent inhibitors of metabolic functions of all tested cell lines which were cultured in the presence and absence of different stimuli. For example, membrane fraction extract clearly demonstrated greater inhibition potency and its effect could be reliably measured at a dose of 0.001%. The cell juice serum demonstrated a complex response: stimulation at a lower dose and inhibition at a high dose.

It should be noted that rather than inducing necrotic cytolysis, membrane fraction extract and cell juice serum appear to initiate a pathway of programmed, or apoptotic cell death in the tumor cells. The experimental data indicate that this pathway is attributed to loss of mitochondrial function and may require 24 to 48 hours of exposure to be detected.

As a consequence of exposure to bioactive compositions, the metabolic function of all tested tumor cell lines: MCF-7, a model of early stage human breast cancer, MDA-MB-435S, a model of advanced breast cancer, and Mono Mac 6, a model of monocytic leukemia, was inhibited, most effectively by the membrane fraction extract and, less potently and more selectively, by the cell juice serum. Remarkably, the white tea extract and cell walls fraction extract were proven to be inactive or much less potent than the above compositions B and D. This trend was clearly proven for the cells tested under different conditions: MCF-7 cells in the absence and in the presence of transforming growth factor, MDA-MB-435S cells and both stimulated and non-stimulated monocytic Mono Mac 6 cells.

These results provide strong evidence of the ability of the method of the present invention to drastically increase the potency of *Camellia* plants and produce very impressive novel products demonstrating activities, which were not identified for even the best product of conventional tea technology.

Effects of the *Camellia* fractions of the present invention on cell-mediated proteolytic activities have implications for inflammatory tissue injury as well as tumor invasion and metastasis. Thus, breast cancer cells and leukemia cells clearly can be suggested as prospective targets for the bioactive compositions of the present invention, most notably, the membrane fraction extract. It should be noted that it was previously shown that the colon carcinoma-derived cell line COLO 205 releases significant levels of MMP-2, which is then activated by a trypsin-like enzyme also secreted by the cells. This is also one of potential targets for the *Camellia* fractions of the present invention, based on results with Mono Mac 6 cells.

From these studies it has been concluded that the present invention's bioactive compositions isolated from fresh *Camellia* have activities result in impressive modulation of key cell functions. The effects that have been observed could have valuable applications ranging from personal care products to nutraceuticals and potentially pharmaceuticals.

It should also be noted that the present invention's very potent bioactive compositions are not single purified components, but rather isolated complexes of constituents. Further fractionation of membrane fraction extract (composition B) and cell juice serum (composition D) could yield extremely potent ingredients for the growing market of natural pharmaceuticals.

Example 11

Comparative Evaluation of *Camellia* Products: Tested Compositions

The following bioactive compositions were used in the experiments described in Examples 10 through 19:
(1) Positive Control: White tea extract which was prepared according to the procedure described in Examples 1 and 4.
(2) Composition A: A cell walls fraction extract of fresh leaves of *Camellia* which was prepared according to procedure described in Examples 1 and 4.
(3) Composition B: A membrane fraction extract obtained from freshly processed leaves of *Camellia* and prepared according to procedure described in Examples 1 and 4.
(4) Composition D: Cell juice serum of freshly processed leaves of *Camellia* and prepared according to the procedure described in Examples 1 and 4.

The above products were obtained from the same lot of fresh *Camellia* to prepare the conventional white tea extract and three "parallel" products of the present invention (compositions A, B and D).

There are a number of reports in the literature, which suggest that extracts of *Camellia* leaves have a range of biological activities, primarily attributed to the significant concentrations of polyphenolic tannins that form during the curing process. These polyphenols, as well as lower molecular weight precursors to the polymeric tannins such as epigallocatechin-3-O-gallate (EGCG), have been reported to display potent antioxidant activities. There is a growing number of publications suggesting not only antioxidant, but also anti-angiogenic, anti-bacterial, anti-neoplastic, anti-inflammatory, anti-mutagenic, anti-septic, and detoxifying properties of teas prepared from dried leaves of *Camellia*. Not all of the above properties have been proven to confer statistically significant benefits. Only some of them have been confirmed in comprehensive studies using multiple testing systems.

As past reference, it should be pointed out that, from past experience with bioactive compositions isolated from a number of fresh plant sources other than *Camellia* using the present invention's technology, such compositions were proven to be much more potent than conventional products isolated from the same dried plants using a number of parameters as was previously described in the U.S. Patent Application Publication No. 2003/0175235, which is hereby incorporated by reference in its entirety). For example, in other types of plants (*Medicago sativa, Hordeum vulgare, Lavandula angustifolia, Calendula officinalis* and *Salvia officinalis*), several impressive biological activities of compositions prepared using the method of the present invention have been identified and evaluated, including high anti-elastase and anti-gelatinase B (MMP-9) activities, novel modulation of the neutrophil respiratory burst, and significant superoxide scavenging activity towards reactive oxygen species. Other than scavenging activity, these activities are not likely to be ascribed to mixtures of polyphenols alone.

Thus, it was especially interesting to explore a more comprehensive approach to compare the range of activities, which could be detected in the *Camellia* compositions of the present invention with the activities present in an extract obtained from the same dried plant using conventional (traditional) *Camellia* technology. Accordingly, modulation of functions in living mammalian cells by the cell walls fraction extract (composition A), membrane fraction extract (composition B) and cell juice serum (composition D) prepared from freshly collected leaves of *Camellia* have been assayed. These compositions have been compared to extract of conventional white tea prepared from dried *Camellia* leaves.

It should be noted that, according to multiple studies of conventional *Camellia* products, the white tea extract demonstrated higher specific activities and therefore a preparation of this sort was selected as a representative positive reference control for comparison with the novel *Camellia* products of the present invention.

Example 12

Comparative Evaluation of *Camellia* Products: Rationale for Selection of Cell Lines As a test system for modulation of cell functions, two human breast carcinoma-derived lines were used as models of neoplastic cells (MCF-7 and MDA-MB-435S), and a human monocytoid line (Mono Mac 6) was used as a model of inflammatory cells. The above cell lines are described in Example 21.

MCF-7 is considered a model of early or less de-differentiated breast cancer. The line still retains estrogen sensitivity and has a relatively low invasive phenotype; its capacity to metastasize in immunodeficient animal models is quite modest. In previous studies, the MCF-7 cell line has been shown to display a characteristic response to Transforming Growth Factor-$\beta$(TGF-$\beta$): after culture for 24 hours in the presence of TGF-$\beta$, the cells secrete increased levels of the Matrix Metallo Proteinase (MMP) family of proteolytic enzymes and the pro-angiogenic factor Vascular Endothelial Growth Factor (VEGF), two different markers of enhanced invasiveness and metastatic potential. This response to TGF-$\beta$ is a mark of tumors and some tumor cell lines, in contrast to growth arrest, which is induced in normal cells by the growth factor. To evaluate the bioactive compositions of the present invention, MCF-7 cells cultured in the absence and presence of TGF-$\beta$ were used as targets.

The MDA-MB-435S line is more highly invasive, metastatic and estrogen insensitive. This human carcinoma-derived cell line also shows some sensitivity to TGF-$\beta$, but even in the absence of the growth factor, it spontaneously releases higher levels of MMPs and VEGF than MCF-7, consistent with its use as a model of more advanced cancer. In present evaluation the effects of bioactive compositions on MDA-MB-435S cells cultured only in the absence of TGF-$\beta$ were examined.

The human monocytoid line, Mono Mac 6, expresses a number of biomarkers consistent with those of resting monocytes or macrophages, and responds like human monocytes and macrophages to pro-inflammatory activating stimuli such as Phorbol Myristate Acetate (PMA). The effects of bioactive compositions on Mono Mac 6 cells cultured in the absence and presence of PMA were examined, to serve as models of resting and activated monocytes/macrophages.

Thus, the selected combination of the cell lines described above provides a reliable foundation for evaluations of anti-tumor and anti-inflammatory potencies of *Camellia* bioactive compositions. Parallel testing of selected cell lines with a number of functional probes provides the opportunity to draw more valuable conclusions concerning the activities of products and their mechanism of action-than investigation of the responses of a single test target or targets having similar sensitivities or similar responses to certain stimuli.

Example 13

Comparative Evaluation of *Camellia* Bioactive Compositions: Rationale for Selection of Assays Initial evaluations were based on two viability assays and a probe of cell functions (see Example 20, "Method 8").

The first assay measures levels of the cytosolic enzyme, lactic dehydrogenase, which is liberated into the extracellular culture medium only when the cells lyse. Such loss of cell membrane integrity is traditionally considered to be a sign of necrotic cell death and reflects the cytotoxicity pattern.

The second assay measures mitochondrial dehydrogenase activity as reflected by the reduction of a tetrazolium salt to its colored formazan. When the MTS reagent (a tetrazolium salt) is applied to living cells, it is converted to an intensely colored compound (formazan). Loss of mitochondrial dehydrogenase activity can also be associated with cell death, but is typically a marker for the early steps in a programmed cell death, or apoptotic, pathway in which cell membrane integrity is generally retained well after the nucleus has condensed and the mitochondria have ceased to function.

The leakage of lactic dehydrogenase indicates complete loss of viability associated with cytolysis, while decreased reduction of tetrazolium salts indicates loss of mitochondrial activity, but not necessarily irrevocable loss of cell membrane integrity or viability.

As an additional probe of cell functions, the effects of the *Camellia* bioactive compositions on levels of proteinases secreted by the Mono Mac 6 line have been examined (see Example 20, "Method 9"). In previous studies with this cell line, it was observed that, after incubation with PMA, Mono Mac 6 cells secrete two so-called gelatinolytic matrix metalloproteinases, MMP-2 (gelatinase A) and MMP-9 (gelatinase B). These MMPs are also secreted by a number of tumors and by their surrounding stroma, and are implicated in inflammatory tissue injury as well as tumor invasion and metastasis. It was also previously shown that some agents under development as anti-inflammatory and anti-tumor drugs (the agents that have been investigated are known to diminish inflammatory tissue destruction as well as invasion and metastasis of tumor cell lines) appear to reduce the levels of the MMPs produced by cells in addition to any direct inhibition of MMP proteolytic activity. The objective in these studies was to evaluate the possibility that the *Camellia* bioactive compositions of the present invention might have a similar capacity to diminish levels of MMPs released by activated Mono Mac 6 cells.

Thus, the selected assays will allow one to reliably evaluate a broad spectrum of metabolic processes and effectively obtain important data, which might reveal mechanisms of action triggered by certain *Camellia* bioactive compositions.

Example 14

Comparative Evaluation of *Camellia* Products: Effects of *Camellia* Bioactive Compositions on Breast Tumor Cell Lines Throughout these studies, mitochondrial function was measured solely through assays of reduction of the tetrazolium salt MTS to its formazan. It should be noted that some intrinsic capacity of higher concentrations of the *Camellia* compositions of the present invention have been observed to reduce MTS directly in the absence of any viable cells, and in all the results reported here, such background formation of formazan in the absence of cells has been subtracted from the levels of reductase activity observed in the presence of the cells.

FIGS. 14 through 21 illustrate the magnitude of the reductase activity of MCF-7 cells, cultured in the absence and presence of 5 ng/ml TGF-β, and MDA-MB-435S cells, cultured only in the absence of TGF-β, at 24 hours and 48 hours after the addition of various doses of each of the four *Camellia* compositions, ranging from 0.01% or 0.02% (w/v, final concentration in the culture medium, based on dry weight of the solids in the *Camellia* compositions) to 0.0001%.

Example 15

Comparative Evaluation of *Camellia* Bioactive Compositions: MCF-7 Cells

In the absence of TGF-β, the highest tested concentration (0.01%) of the composition A and white tea extract (positive control) had a marked effect on MTS reduction by MCF-7 cells. At that concentration there was significant but incomplete inhibition of reductase activity (~50-70% inhibition) after 24 hours of exposure to the *Camellia* composition A. The similar inhibition of reductase activity was detected after 24 hours of exposure to white tea extract.

In contrast, the two *Camellia* bioactive compositions (membrane fraction extract and cell juice serum) prepared from *Camellia* cell juice were more potent inhibitors of reductase activity in MCF-7 cells in the absence of TGF-β. The membrane fraction extract (composition B) resembled white tea extract in dose dependence, except for somewhat greater potency, producing virtually complete inhibition at 0.01%, the highest dose tested. The cell juice serum (composition D) also produced virtually complete inhibition at 0.01%, but at the lower dose of 0.0025%, there was some evidence of stimulation of reductase activity. Lower doses of composition D were without significant effect.

When MCF-7 cells were cultured in the presence of the growth factor TGF-β, their sensitivity to the *Camellia* compositions was significantly altered. After 24 hours or 48 hours of exposure to the cell walls fraction extract and white tea extract, there was no evidence of either a stimulatory or an inhibitory effect on reductase activity at any dose, except for a modest inhibition of less than 20% at the highest dose (0.01%) of white tea extract.

In contrast, exposure of TGF-β-treated MCF-7 cells for 24 hours to the membrane fraction extract at a dose of 0.02% resulted in 70% inhibition of reductase activity, and after 48 hours, reductase activity was virtually completely abated. More modest inhibition could be detected at lower doses of membrane fraction extract after 24 hours, but after 48 hours, a marked activation of reductase activity was detected. The same activation of reductase activity by low doses of the cell juice serum as well as marked inhibition at the highest dose (0.02%) was detected after 48 hours of exposure, but this composition had only minimal effect on reductase activity in TGF-β-treated MCF-7 cells after the more limited exposure of 24 hours, regardless of dose.

In evaluation, there was no detection of significant release of lactic dehydrogenase into the culture medium of MCF-7 cells exposed for 24 hours to even the highest doses of any of the *Camellia* compositions. It would appear that, the loss of mitochondrial function in these cells is not accompanied by a necrotic lysis of the cells. If the cells are in fact dying during the first 48 hours of exposure, it is more likely that a programmed cell death, or apoptotic, pathway has been initiated. This conclusion is supported by light microscopic observations, which reveal that there is some rounding of the cells, but no formation of debris or membrane fragments during the course of the exposures.

Thus, inhibition of mitochondrial function appears to be a predominant mode of action of all tested *Camellia* products, which did not demonstrate cytotoxity or necrosis as indicated by levels of released lactic dehydrogehase.

Example 16

Comparative Evaluation of *Camellia* Bioactive Compositions: MDA-MB-435S Cells

The pattern of response of MDA-MB-435S cells to the *Camellia* compositions was similar to that of MCF-7 cells in that the most potent compositions were composition B and D, with the membrane fraction extract (composition B) showing somewhat greater potency than the cell juice serum (composition D). Only the membrane fraction extract produced marked inhibition of reductase activity after only 24 hours of exposure Inhibition reached −70% of control reductase values at the highest dose of 0.01%, but a modest inhibition of −10% could be reliably detected at even the lowest dose of remarkable concentration −0.0001%. The other tested compositions had only modest inhibitory effects at 24 hours of exposure, and only at the higher doses tested.

After 48 hours of exposure, reductase activity was inhibited in a dose-dependent fashion in the presence of each of the compositions, but the potency at the highest dose of the compositions did not reach near 100% inhibition, except for the membrane fraction extract. This composition inhibited reductase activity by −50% at 0.001% after 48 hours. The white tea extract and cell walls fraction extract also had significant inhibitory activity against MDA-MB-435S cells after 48 hours of exposure, which was actually greater than that of the cell juice serum. No doses of any of the preparations induced activation of reductase activity in this cell line, regardless of duration of exposure.

It should be noted that any impact on highly invasive, metastatic and estrogen insensitive line MDA-MB-435S is rare to observe after only 24 hours. Thus, the effect of composition B after 24 and 48 hours is rather remarkable and indicates that this preparation has significant activity.

Example 17

Comparative Evaluation of *Camellia* Bioactive Compositions: Effects of *Camellia* Compositions on Monocytoid Cells Mitochondrial Dehydrogenase Activity: Certain of the trends revealed by the preliminary studies on the breast tumor cell lines have proved to be consistent with the response of Mono Mac 6 cells to the four tested *Camellia* compositions. The membrane fraction extract (composition B) and cell juice serum (composition D) were more potent inhibitors of MTS reductase activity in this inflammatory cell line than the cell walls fraction extract (composition A) and white tea extract (positive control), and the membrane fraction extract (composition B) clearly had the greatest inhibitory potency. The effects on MTS reductase in cells which were left unstimulated and those which were stimulated with 10 nM PMA were examined, and reductase activity after 24 and 48 hours of exposure to the *Camellia* compositions was evaluated. The effects of these compositions on MTS reductase activity in Mono Mac 6 cells are shown in FIGS. 22 through 33.

The white tea extract showed a weak but dose-dependent inhibition of reductase activity after 48 hours of exposure to PMA-stimulated cells; there was no significant loss of reductase activity regardless of the dose or length of exposure in the absence of PMA, nor was there any effect of any dose after 24 hours of exposure to PMA-treated cells. The cell walls fraction extract had no effect on Mono Mac 6 cells regardless of dose or time of exposure and regardless of whether the cells were unstimulated or stimulated with PMA.

The cell juice serum of fresh *Camellia* leaves inhibited unstimulated Mono Mac 6 cell reductase activity modestly in a dose dependent fashion after 24 or 48 hours of exposure. The maximum inhibition at the highest dose of 0.01% (w/v, final concentration in the culture medium, based on dry weight of solids in the starting preparation) was only ~20-30% of the control activity. Inhibition of PMA-stimulated cells reached 50% of control activity but only at the highest dose of composition D (0.01%), and only after 48 hours of exposure.

The membrane fraction extract of freshly harvested *Camellia* (composition B) proved to be the most potent of the tested preparations in inhibiting Mono Mac 6 cell reductase activity as it had toward the breast tumor cell lines. Effects of PMA stimulation or duration of exposure to the composition had little effect on inhibition, which was dose-dependent in the presence or absence of PMA and was roughly the same after 24 hour or 48 hour exposure. Reductase activity was inhibited by ~70% in the presence of PMA and by ~80-90% in the absence of PMA at the highest dose of 0.02%, but lower levels of inhibition (~15%) could be reliably measured at a dose of 0.001%. Measurements of release of cytosolic enzymes have not been undertaken to confirm that the loss of reductase activity is not associated with necrotic cytolysis, but no evidence of membrane fragmentation could be seen by light microscopic examination of Mono Mac 6 cells exposed to any of the bioactive compositions at 0.02% for 48 hours. Moreover, as shown below, the cells appear still capable of secreting at least one MMP under conditions in which reduction of MTS is markedly diminished.

These results suggest that in these cells, as well as the breast tumor cell lines, the loss of reductase activity is associated with a relatively selective loss of mitochondrial function and can reflect initiation of a pathway of programmed cell death or apoptosis.

Secretion of MMPs. Two different assays have been used to measure the levels of two gelatinases, MMP-2 (gelatinase A) and MMP-9 (gelatinase B), released by Mono Mac 6 cells. These MMPs have been implicated in inflammatory tissue damage as well as tumor invasion and metastasis. Employed enzyme-linked immunosorbent assays (ELISAs) for MMP-2 and MMP-9 were first used to estimate total levels of the two enzymes in the culture medium of Mono Mac 6 cells cultured for 48 hours in the presence of 10 nM PMA and different doses of the three *Camellia* bioactive compositions and positive control.

This cell line secretes only MMP-2 when it is unstimulated, but secretes both MMP-2 and MMP-9 when it is activated. (Levels of MMPs released after 24 hours are usually too low to be reliably detected).

The results of the ELISA measurements are shown in FIGS. 34 through 37. As was observed for the effects of cell walls fraction extract and white tea extract on MTS reduction by Mono Mac 6 cells, there was no significant change in levels of secreted MMP-2 or MMP-9 at any dose of these extracts. At the highest dose (0.01% w/v) of the membrane fraction extract and cell juice serum, the levels of MMP-2 were observed to be diminished, with the membrane fraction extract exhibiting the greatest potency at this dose. It should be noted, that an apparent slight stimulation of MMP-2 release was observed at the next highest doses of composition B (0.001%) and composition D (0.002%). This stimulation is reminiscent of the stimulation of MTS reductase activity in TGF-$\beta$ treated MCF-7 cells at similar doses of these compositions.

The dose-dependent diminution of MMP-2 levels detected by ELISA was not paralleled by the effects of membrane fraction extract and cell juice serum on MMP-9 levels. These levels were increased (apparently markedly so by cell juice serum) at the highest doses, but were unchanged at the lower doses tested. The detection of unchanged or increased levels of MMP-9 secreted by Mono Mac 6 cells exposed for 48 hours to doses of *Camellia* preparations which produced significant inhibition of MTS reductase activity after only 24 hours, is further evidence that the loss of mitochondrial function in Mono Mac 6 cells exposed to the membrane fraction extract or cell juice serum of *Camellia* does not reflect necrotic cytolysis, in which case MMP secretion would have abruptly ceased.

As further evidence of the effects of the *Camellia* compositions on MMP secretion by Mono Mac 6 cells, the technique of gelatin zymography was used to examine the culture media collected as described above for the ELISA measurements. In this method, the culture media are first subjected to electrophoresis in gelatin-impregnated polyacrylamide gels in the presence of Sodium Dodecyl Sulfate (SDS-PAGE) to separate the proteins on the basis of molecular weight. The SDS is then washed out of the gels to allow at least a portion of any enzymes present to renature and the gels are incubated in a medium, which maximizes MMP activity. MMPs dissolve the gelatin wherever they may be present. After visualizing the undigested gelatin in the bulk of the gels with a protein stain, the gels are scanned, with the MMPs appearing as clear zones against the stained background. Negative images have been presented here, so that the MMPs appear as dark zones against a light background.

It should be noted that MMPs are secreted by most cells as inactive precursors, which are then activated extracellularly. However, because of the denaturing and renaturing sequence employed in zymography, even the so-called inactive proforms of the MMPs acquire gelatinolytic activity and produce clear zones. FIGS. 34 through 37 illustrate the negative images of gelatin zymograms of culture media collected after 48 hour exposure of Mono Mac 6 cells to the different *Camellia* bioactive compositions, along with culture medium collected from cells cultured in the absence (U) or presence (S) of 10 nM PMA but in the absence of *Camellia* compositions.

The effects of composition A and positive control were evaluated only for the lowest dose (0.0001%, "10") and the highest dose (0.01%, "hi") of the preparations, whereas the effects of compositions B and D were also evaluated at the intermediate dose of 0.001% ("med"). It is apparent from the four panels that Mono Mac 6 cells release only MMP-2 (~67 kD) in the absence of PMA, and this enzyme is found predominantly in the pro-form. Treatment with 10 nM PMA results in induction of MMP-9 secretion (~0.92 kD), as well as further proteolytic activities which convert significant levels of the pro-forms of the two MMPs to their slightly lower molecular weight active forms.

Consistent with the ELISA results, exposure of PMA-stimulated Mono Mac 6 cells to cell walls fraction extract and white tea extract had no detectable effect on the levels of either the pro- or active forms of either of the two MMPs visualized by gelatin zymography. In contrast, exposure to the highest dose of compositions B and D resulted in marked diminution of the levels of MMP-2 visualized by gelatin zymography, but no apparent change in the levels of MMP-9.

The appearance of both pro- and active forms of MMP-9, as well as the faint, but recognizable, band corresponding to the active form of MMP-2 seen in the media collected from cells treated with the highest dose of compositions B and D, suggests that the effects of these compositions are primarily on modulation of release of MMP-2 and do not involve additional effects on the MMP activation mechanisms in these cultured cells.

Example 18

Comparative Evaluation of *Camellia* Bioactive Compositions: Summary of Results

The experimental data indicate that *Camellia* bioactive compositions trigger a dose-dependent loss of MTS reductase activity, which is generally attributed to loss of mitochondrial function. This inhibition may require as long as 48 hours of exposure to be detected and at least for the first 24 hours, there is no measurable release of cytosolic enzymes, suggesting that rather than inducing necrotic cytolysis, the bioactive compositions initiate a pathway of programmed, or apoptotic, cell death in the tumor cells.

The differences in the time- and dose-dependence of the response of MCF-7 cells and MDA-MB-435S cells, and the effects of TGF-β treatment of the MCF-7 cells, all point to a somewhat increased resistance of the more invasive and metastatic phenotypes to white tea extract, cell walls fraction extract, and to some degree, cell juice serum, as evidenced by the relatively modest loss of reductase activity within the first 24 hours of exposure. However, the trend of greater potency of the membrane fraction extract is evidenced by its capacity to inhibit MTS reductase activity in TGF-β-treated MCF-7 cells, as well as MDA-MB-435S cells within 24 hours.

The effects of tested *Camellia* bioactive compositions on the Mono Mac 6 cell line, a model of human monocytes/macrophages, have certain similarities to the effects observed on breast tumor cell lines. Based on the absence of lactic dehydrogenase in the culture medium of the breast tumor cell lines and the presence of normal to increased levels of secreted MMP-9 in the culture medium of Mono Mac 6 cells, it has been concluded that these compositions do not induce necrotic cytolysis, even at the highest dose tested (0.01% w/v).

However, the two bioactive compositions (membrane fraction extract and cell juice serum) induce a dose-dependent inhibition of mitochondrial reductase activity, which reflect initiation of an apoptotic pathway of programmed cell death in Mono Mac 6 cells. Furthermore, exposure of these inflammatory cells to the membrane fraction extract and cell juice serum results in selective diminution in the levels of the gelatinolytic enzyme, MMP-2 (gelatinase A). The gelatin zymography indicates that mechanisms of "pro-form" or zymogen activation are unaffected by the *Camellia* bioactive compositions, so it is highly unlikely that the diminished levels MMP-2 in the medium reflect enhanced proteolytic destruction.

Thus, the metabolic activity of all tested cell lines (i.e., a model of early stage human breast cancer, a model of advanced breast cancer cells, and a model of monocytic leukemia) was effectively inhibited by the membrane fraction extract (composition B) and, in most of cases, the cell juice serum (composition D). Remarkably, the extract of cell walls tea (Composition A) and white tea extract (positive control) were proven to be inactive or much less potent than the above compositions B and D.

This trend was clearly proven for all tested MCF-7 human cancer cells in the absence and in the presence of transforming growth factor, for MDA-MB-435S advanced human breast cancer cells, and for stimulated and non-stimulated monocytoid Mono Mac 6 cells. The data related to the summary of testing and evaluation of bioactive *Camellia* compositions are presented in Table 15.

TABLE 15

Summary of Testing and Evaluation of Bioactive *Camellia* Compositions

| Cell Line and Model | Stimuli | Time of Cultivation | White Tea Extract (Positive Control) | Extract of Cell Walls Fraction (Composition A) | Extract of Membrane Fraction (Composition B) | Cell Juice Serum (Composition D) |
|---|---|---|---|---|---|---|
| Human Cancer Cells MDA-MB-435S Advanced Breast Cancer | | 24 hours | Modest Inhibition | Modest Inhibition | Strong Inhibition | Modest Inhibition |
| | | 48 hours | Significant but Incomplete Inhibition | Significant but Incomplete Inhibition | Complete Inhibition | Significant but Incomplete Inhibition |
| Human Cancer Cells MCF-7 Early Breast Cancer | | 24 hours | Significant but Incomplete Inhibition | Significant but Incomplete Inhibition | Complete Inhibition | Complete Inhibition |
| | TGF-β | 24 hours | Modest Inhibition | No Effect | Significant but Incomplete Inhibition | Complete Inhibition |
| | | 48 hours | Modest Inhibition | No Effect | Stimulation at Lower Dose and Complete Inhibition at High Dose | Stimulation at Lower Dose and Significant but Incomplete Inhibition at High Dose |
| Human Leukemia Cells Mono Mac 6 | | 24 hours | Modest Inhibition | Modest Inhibition | Complete Inhibition | Pronounced Inhibition |
| | | 48 hours | No Effect | No Effect | Significant but Incomplete Inhibition | Pronounced Inhibition |

TABLE 15-continued

Summary of Testing and Evaluation of Bioactive Camellia Compositions

| Cell Line and Model | Stimuli | Time of Cultivation | White Tea Extract (Positive Control) | Extract of Cell Walls Fraction (Composition A) | Extract of Membrane Fraction (Composition B) | Cell Juice Serum (Composition D) |
|---|---|---|---|---|---|---|
| Inflammation | PMA | 24 hours | No Effect | Modest Inhibition | Significant but Incomplete Inhibition | Significant but Incomplete Inhibition |
|  |  | 48 hours | Modest Inhibition | No Effect | Significant but Incomplete Inhibition | Significant but Incomplete Inhibition |

Table 15 shows that abilities of Camellia preparation to modulate cell functions in a dose-dependent manner is increasing in the following order: white tea extract=cell walls fraction extract>cell juice serum>membrane fraction extract. The experimental data suggests that, novel bioactive Camellia compositions prepared by processing of fresh plant tissue into cell juice derived membrane fraction extract (composition B) and cell juice serum (composition D) do not trigger any outright necrotic toxicity towards the cells.

Therefore, the technology of the present invention displays the ability to drastically increase the potency of Camellia bioactive compositions and to produce very impressive novel products demonstrating activities on viable human cells which were not demonstrable in the best products (for example, white tea extract) produced by conventional Camellia technology.

Example 19

Comparative Evaluation of Camellia Bioactive Compositions Implications for Future Studies Effects of the Camellia bioactive compositions of the present invention on cell-mediated proteolytic activities have implications for inflammatory tissue injury as well as tumor invasion and metastasis. Thus, breast cancer cells and monocytic leukemia cells clearly can be suggested as prospective targets for the Camellia bioactive compositions of the present invention, most notably, composition B (membrane fraction extract). It was previously shown that the colon carcinoma-derived cell line COLO 205 releases significant levels of MMP-2, which is then activated by a trypsin-like enzyme also secreted by the cells. This type of tumor cell is one of a number of potential targets for the Camellia bioactive compositions of the present invention, based on results with Mono Mac 6 cells.

From these studies, one can be confident that the bioactive compositions isolated from fresh Camellia of the present invention have significant activities, which result in impressive modulation of key cell functions. The effects that have been observed have valuable applications ranging from personal care products to nutraceuticals and potentially pharmaceuticals.

Example 20

Protocols Used for Determining Certain Characteristics of Bioactive Compositions The following are various methods used for determining certain characteristics of Bioactive Compositions. These methods are referenced throughout the above Examples. References below to the "tested products" or the "test samples" refer to Bioactive Compositions.

Method 1: Method for Determination of Solid Content. The procedure for determination of solid content included evaporation of the tested bioactive composition in the water bath at 100° C. until complete evaporation of water, oven storage of the sample at 105° C. for 3 hours, cooling to room temperature, and immediate determination of the weight of the container with solid matter.

Method 2: Method for Determination of Non-Volatile Residue. The procedure for determination of non-volatile residue included oven storage of the tested bioactive composition at 105° C. for 5 hours, cooling, and immediate determination of the weight of the container with solid matter.

Method 3: Method for Determination of L*a*b* Values. The procedure for determination of L*a*b* values utilized Hunter Labscan fixed geometry colorimeter with measuring geometry of 0°/45°. Standard illuminant $D_{65}$ with viewing window facing upward was used. The container with tested bioactive composition was placed on viewing window and measured through the bottom. The following CIELAB equations were used:

$$C^* = (a^{*2} + b^{*2})^{1/2}$$

$$DE^* = [(DL)^2 + (Da^*)^2 + (Db^*)^2]^{1/2}$$

$$DH = [(DE^*)^2 - (DL^*)^2 - (DC^*)^2]^{1/2}.$$

Method 4: Method for Determination of Total Carotenoids Content and Lutein Content. The tested bioactive compositions were extracted with acetone. After homogenization and vacuum filtration, all extracts were saponified with 30% potassium hydroxide in methanol. The carotenoids were successively extracted from bioactive compositions with petroleum ether. After additional treatment and re-solubilization in ethanol, all samples were measured at 446 nm.

In order to determine the lutein content, an additional dried sample from each sample extraction was used for high performance liquid chromatography ("HPLC") analysis. The dried sample was re-solubilized in MTBE and methanol. The reverse phase HPLC system with (250×4.60 mm I.D.) 5 μm $C_{18}$ column ("Vydac") was used. The identity of lutein was conformed by the co-chromatography of an authentic standard. The molar absorptivity coefficient for lutein in ethanol is 144,800 $cm^{-1}$ $mol^{-1}$.

Method 5: Method for Determination of Elastase Inhibitory Activity. The elastase inhibitory activity of tested bioactive compositions was determined using the assay, which employs neutrophil elastase (a purified enzyme preparation produced by "Elastin Products") and synthetic peptide soluble substrate Methoxysuccinyl-Ala-Ala-Pro-Val-p-Nitroanilide produced by "Sigma". Enzymatic cleavage of the substrate results in generation of increasing yellow color over time (405 nm); the rate of color generation is diminished by increasing concentrations of tested bioactive compositions containing inhibitory activity. Analysis of the concentration dependence of inhibition permits quantitation of the potency of the inhibitory activity, expressed as that concentration of dry matter within each tested bioactive required to achieve 50% inhibition ($IC_{50}$), but also provides information relating to the mode of inhibition.

For the determination of $IC_{50}$, the concentration of elastase was 2.5 µg/ml and concentration of substrate was 150 µM. For the determination of $K_i$, the concentrations of substrate were 100 µM and 200 µM.

Method 6: Method for Determination of Gelatinase B (MMP-9) Inhibitory Activity. The commercially distributed assay (MMP-9 Activity ELISA produced by "Amersham Pharmacia"), which captures Gelatinase B specifically onto multiwell microplates by immune recognition, was used after other proteinases were washed away. The enzymatic activity was detected at 405 nm by hydrolysis of a low molecular weight synthetic substrate for Gelatinase B: APMA. Analysis of the concentration dependence of inhibition was used to determine the potency of tested bioactive composition dry matter.

Method 7: Method for Determination of Superoxide Scavenging Activity. The enzymatic system, which uses xanthine oxidase (a purified enzyme preparation produced by "Sigma"), was used to generate superoxide anions in high yield and in a controlled fashion. The conversion of xanthine to hydroxanthine by this enzyme generates amounts of superoxide anions and reduction of ferricytochrome c to ferrocytochrome c was used as a sensitive measure of superoxide levels. The measurements of ferrocytochrome c level (550 nm), when tested bioactive compositions were added to the reaction system, allow for determination of their superoxide scavenging activity. The final concentrations per well were for cytochrome c 75 µM, xanthine 425 µm/L, and xanthine oxidase 10 mU/ml.

Method 8: Method for Determination of In Vitro Toxicity and Apoptosis. CellTiter 96 $AQ_{ueous}$ One Solution Cell Proliferation Assay and CytoTox 96 Non-radioactive Cytotoxicity Assay and subsequent protocols were explored (both assays produced by Promega Corporation, Madison, Wis.).

The first assay is a colorimetric method for determining the number of viable cells which explores a tetrazolium compound (3-(4,5-dimethylthianzol-2-yl)-5-(3-carboxymethoxyphenyl)-2-(4-sulfophenyl)-2H-tetrazolium, inner salt; MTS and a electron coupling reagent (phenazine methosulfate; PMS). MTS is bioreduced by cells into a soluble in tissue culture medium formazan product that has an absorbance maximum at 490 nm. The conversion of MTS into aqueous, soluble formazan is accomplished by dehydrogenase enzymes found in metabolically active cells and the quantity of formazan product is directly proportional to the number of living cells in culture.

The second assay quantitatively measures lactate dehydrogenase (LDH), a stable cytosolic enzyme that is released upon cell lysis. Released LDH in cell culture supernatant is measured with a 30-minute coupled enzymatic assay, which results in the conversation of a tetrazolium salt (INT) into a red formazan product. The amount of color formed is proportional to the number of lysed cells.

Method 9: Method for Determination of Level of Enzymes Secreted by Stimulated Cells. After incubartion with PMA, Mono Mac 6 cells secrete two gelatinolytic matrix metalloproteinases, MMP-2 (gelatinase A) and MMP-9 (gelatinase B). The levels of these enzymes in the presence of tested bioactive compositions were determined by two-dimensional sodium dodecyl sulphate polyacrylamide gel electrophoresis.

Example 21

Cell Lines Used for Testing Certain Bioactive Characteristics of the *Camellia* Products The cell line MDA-MB-435S which is considered a model of advanced breast cancer was obtained from American Type Culture Collection (ATCC Number HTB-129). This cell line was cultivated at 37° C. in the following ATCC medium: Leibovitz's L-15 medium with 2 mM L-glutamine supplemented with 0.01 mg/ml insulin, 90%; fetal bovine serum, 10%.

The cell line MCF-7 which is considered a model of early or less de-differentiated breast cancer was obtained from ATCC (Number HTB-22) was cultivated at 37° C. in the following ATCC medium: Minimum essential medium (Eagle) with 2 mM L-glutamine and Earle's BSS adjusted to contain 1.5 g/L sodium bicarbonate, 0.1 mM non-essential amino acids and 1 mM sodium pyruvate and supplemented with 0.01 mg/ml bovine insulin, 90%; fetal bovine serum, 10%.

The cell line MonoMac6 (MM6, obtained from the German Collection of Microorganisms and Cell Cultures) which closely resembles a differentiated human monocyte (Ziegler-Heitbrock et al., "Establishement of a Human Cell Line (Mono Mac 6) with Characteristics of Mature Monocytes," *International Journal of Cancer* 41:456-461 (1988), which is hereby incorporated by reference in its entirety). Cells were maintained in RPMI 1640, supplemented with 2 mM L-glutamine, 100 U/ml penicillin, 100 µg/ml streptomycin, 1 mM sodium pyruvate, 10% FCS, nonessential amino acids, 9 µg/ml insulin, and 1 mM oxalacetic acid. For assay conditions, 0.2% glucose was also added.

Example 22

Catechin Analyses of the *Camellia* Products

The cell walls fraction extract, the membrane fraction extract, and the cell juice serum of the present invention were analyzed for content of various catechins. A white tea sample was used as a control. The following catechins were assayed: (−)-epigallocatechin; (+)-catechin; (−)-epicatechin; (−)-epigallocatechin gallate; (−)-gallocatechin gallate; and (−)-epicatechin gallate.

Figure 38:
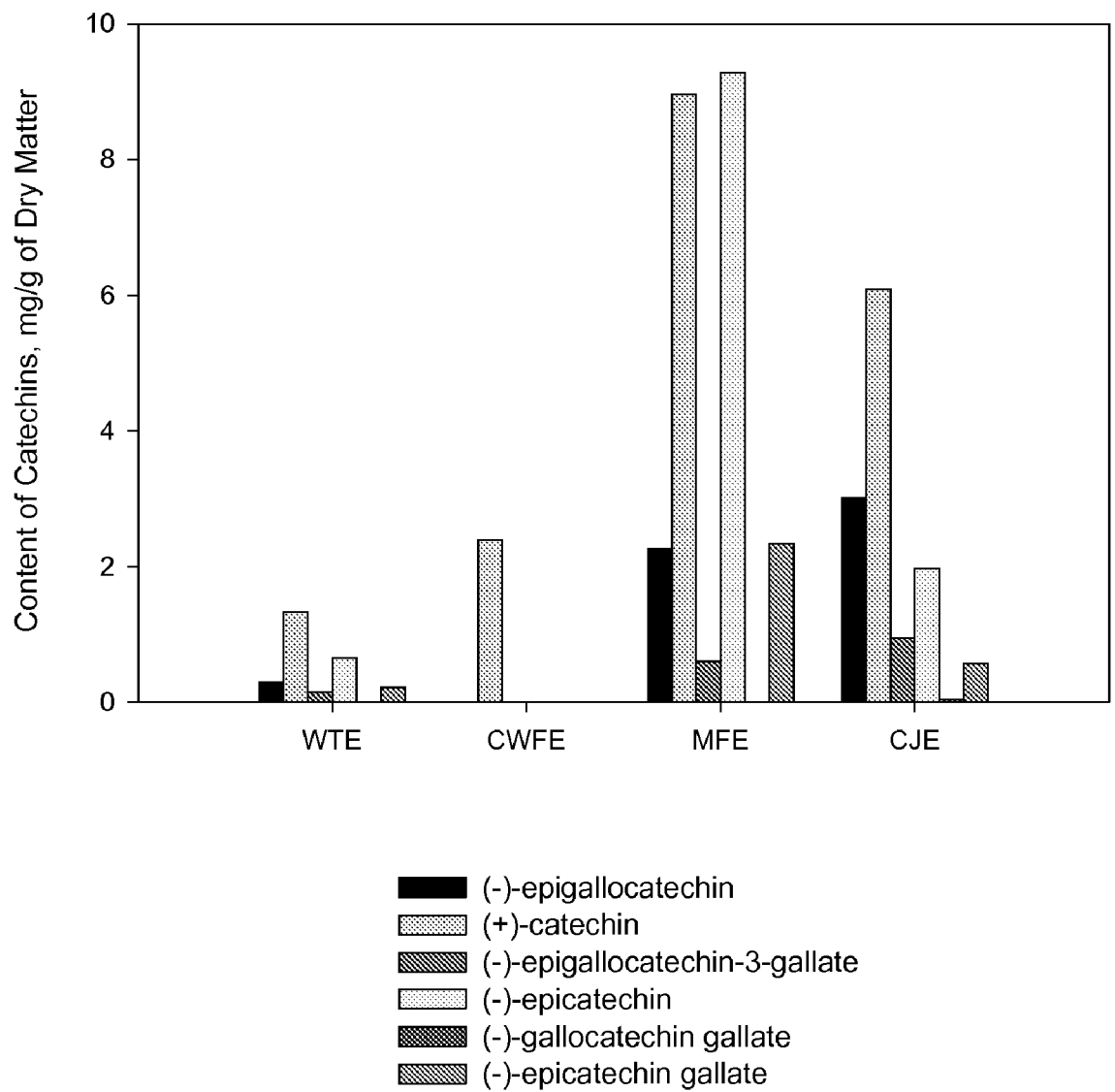
FIG. 38 is a bar graph comparing the content of various catechins in the white tea extract ("WTE") and in the cell walls fraction extract ("CWFE"), the membrane fraction extract ("MFE"), and the cell juice serum ("CJS") of the present invention.

The samples were extracted using 0.1% $H_3PO_4$ and sonication for about 15 minutes. After centrifugation, the extract was injected on HPLC. C-18 reverse phase column was used as the stationary phase. 0.1% phosphoric acid and acetonitrile were used as the mobile phases. The detection was at 280 nm. The calculation is based on comparing areas of each catechin listed with its pure standard. The results are shown in FIG. 38 and Table 16 (below).

TABLE 16

Catechin Content of Bioactive *Camellia* Compositions

| Sample | Chemical Analyzed | Average mg/g based on 100% dry matter | Average mg/g based on product as is |
|---|---|---|---|
| White Tea Extract | (−)-epigallocatechin | 0.3 | 0.0033 |
| | (+)-catechin | 1.33 | 0.0146 |
| | (−)-epicatechin | 0.15 | 0.0017 |
| | (−)-epigallocatechin gallate | 0.65 | 0.0071 |
| | (−)-gallocatechin gallate | 0.003 | 0.0000 |
| | (−)-epicatechin gallate | 0.212 | 0.0023 |

TABLE 16-continued

Catechin Content of Bioactive *Camellia* Compositions

| Sample | Chemical Analyzed | Average mg/g based on 100% dry matter | Average mg/g based on product as is |
|---|---|---|---|
| Cell Walls Fraction Extract | (−)-epigallocatechin | 0.00 | 0.0000 |
| | (+)-catechin | 2.39 | 0.0201 |
| | (−)-epicatechin | 0.01 | 0.0001 |
| | (−)-epigallocatechin gallate | 0.01 | 0.0001 |
| | (−)-gallocatechin gallate | 0.00 | 0.0000 |
| | (−)-epicatechin gallate | 0.006 | 0.0001 |
| Membrane Fraction Extract | (−)-epigallocatechin | 2.27 | 0.1552 |
| | (+)-catechin | 8.96 | 0.6121 |
| | (−)-epicatechin | 0.60 | 0.0409 |
| | (−)-epigallocatechin gallate | 9.28 | 0.6340 |
| | (−)-gallocatechin gallate | 0.01 | 0.0006 |
| | (−)-epicatechin gallate | 2.33 | 0.1589 |
| Cell Juice Serum | (−)-epigallocatechin | 3.01 | 0.1714 |
| | (+)-catechin | 6.09 | 0.3465 |
| | (−)-epicatechin | 0.95 | 0.0539 |
| | (−)-epigallocatechin gallate | 1.97 | 0.1120 |
| | (−)-gallocatechin gallate | 0.04 | 0.0024 |
| | (−)-epicatechin gallate | 0.57 | 0.0325 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A bioactive composition comprising an isolated bioactive fraction, wherein said isolated bioactive fraction is produced by a process comprising:
   (i) providing fresh biomass of a *Camellia sinensis* plant, wherein said fresh biomass comprises fresh *Camellia sinensis* plant biomass that has not undergone conventional tea processing;
   (ii) separating the fresh biomass of the *Camellia sinensis* plant into cell juice and a cell walls component, wherein said separating comprises grinding, macerating, and pressing the fresh biomass to separate the fresh biomass into the cell juice and the cell walls component;
   (iii) treating the cell juice under conditions effective to yield a bioactive fraction, said conditions comprising subjecting the cell juice to microwave treatment to induce coagulation, thereby yielding a coagulated membrane fraction and a non-coagulated portion of the cell juice, wherein said bioactive fraction is the coagulated membrane fraction; and
   (iv) isolating said bioactive fraction from the treated cell juice.

2. The bioactive composition according to claim 1 further comprising a stabilizing agent.

3. The bioactive composition according to claim 2, wherein said stabilizing agent is selected from the group consisting of an emulsifier, a preservative, an antioxidant, a polymer matrix, and mixtures thereof.

4. A bioactive topical formulation suitable for topical application to a mammal, said bioactive topical formulation comprising:
   a topically effective amount of the bioactive composition according to claim 1 and
   a topically acceptable carrier.

5. The bioactive topical formulation according to claim 4, wherein the topically acceptable carrier is selected from the group consisting of a hydrophilic cream base, a hydrophilic lotion base, a hydrophilic surfactant base, a hydrophilic gel base, a hydrophilic solution base, a hydrophobic cream base, a hydrophobic lotion base, a hydrophobic surfactant base, a hydrophobic gel base, and a hydrophobic solution base.

6. The bioactive topical formulation according to claim 4, wherein the bioactive composition is present in an amount ranging from between about 0.001 percent and about 90 percent of the total weight of the bioactive topical formulation.

7. A bioactive composition comprising an isolated bioactive fraction, wherein said isolated bioactive fraction is produced by a process comprising:
   (i) providing fresh biomass of a *Camellia sinensis* plant, wherein said fresh biomass comprises fresh *Camellia sinensis* plant biomass that has not undergone conventional tea processing;
   (ii) separating the fresh biomass of the *Camellia sinensis* plant into cell juice and a cell walls component, wherein said separating comprises grinding, macerating, and pressing the fresh biomass to separate the fresh biomass into the cell juice and the cell walls component;
   (iii) treating the cell juice under conditions effective to yield a bioactive fraction, said conditions comprising subjecting the cell juice to microwave treatment to induce coagulation, thereby yielding a coagulated membrane fraction and a non-coagulated portion of the cell juice, separating the coagulated membrane fraction from the non-coagulated portion of the cell juice, thereby yielding a coagulated membrane fraction; and
   (iv) extracting the membrane fraction with dimethyl sulfoxide, thereby yielding a membrane fraction extract, wherein the bioactive fraction is the membrane fraction extract; and
   wherein said membrane fraction extract has a catechin content profile comprising:
      between about 1.7 and about 3.3 milligrams of (−)-epigallocatechin per gram of dry matter of the membrane fraction extract,
      between about 6.1 and about 10.2 milligrams of (+)-catechin per gram of dry matter of the membrane fraction extract,
      between about 0.3 and about 1.1 milligrams of (−)-epicatechin per gram of dry matter of the membrane fraction extract,
      between about 6.2 and about 12.5 milligrams of (−)-epigallocatechin gallate per gram of dry matter of the membrane fraction extract,
      between about 0.007 and about 0.03 milligrams of (−)-gallocatechin gallate per gram of dry matter of the membrane fraction extract, and
      between about 1.3 and about 3.3 milligrams of (−)-epicatechin gallate per gram of dry matter of the membrane fraction extract.

8. The bioactive composition according to claim 7, further comprising a stabilizing agent.

9. The bioactive composition according to claim 8, wherein the said stabilizing agent is selected from the group consisting of an emulsifier, a preservative, an antioxidant, a polymer matrix, and mixtures thereof.

10. A bioactive topical formulation suitable for topical application to a mammal, said bioactive topical formulation comprising:

a topically effective amount of the bioactive composition according to claim 7 and a topically acceptable carrier.

11. The bioactive topical formulation according to claim 10, wherein the topically acceptable carrier is selected from the group consisting of a hydrophilic cream base, a hydrophilic lotion base, a hydrophilic surfactant base, a hydrophilic gel base, a hydrophilic solution base, a hydrophobic cream base, a hydrophobic lotion base, a hydrophobic surfactant base, a hydrophobic gel base, and a hydrophobic solution base.

12. The bioactive topical formulation according to claim 10, wherein the bioactive composition is present in an amount ranging from between about 0.001 percent and about 90 percent of the total weight of the bioactive topical formulation.

* * * * *